United States Patent
Sahoo et al.

(10) Patent No.: US 6,200,998 B1
(45) Date of Patent: *Mar. 13, 2001

(54) ARYLTHIAZOLIDINEDIONE DERIVITIVES

(75) Inventors: Soumya P. Sahoo, Old Bridge, NJ (US); Wei Han, West Chester, PA (US); Richard L. Tolman, Los Altos, CA (US); Jeffrey Bergman, Tenafly, NJ (US); Conrad Santini, Warren, NJ (US); Ranjit Desai, Franklin Park, NJ (US); Victoria K. Lombardo, Belle Mead, NJ (US); Julia K. Boueres, Franklin Park, NJ (US); Dominick F. Gratale, Edison, NJ (US)

(73) Assignee: Merck & Co., Inc., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/448,847

(22) Filed: Nov. 23, 1999

Related U.S. Application Data

(62) Division of application No. 09/213,542, filed on Dec. 17, 1998, now Pat. No. 6,008,237
(60) Provisional application No. 60/105,238, filed on Oct. 22, 1998, and provisional application No. 60/068,271, filed on Dec. 19, 1997.

(51) Int. Cl.[7] ................................................. A01K 31/425
(52) U.S. Cl. ........................................... 514/369; 514/376
(58) Field of Search ............................. 548/183; 514/364, 514/376

(56) References Cited

U.S. PATENT DOCUMENTS 5,342,850  8/1994  Ohnota et al. .
5,801,173  9/1998  Lohray et al. .

FOREIGN PATENT DOCUMENTS

| 09012575 | 1/1997 | (JP) . |
|---|---|---|
| WO 91/05538 | 5/1991 | (WO) . |
| WO 95/35108 | 12/1995 | (WO) . |
| WO 97/22600 | 6/1997 | (WO) . |
| WO 97/27847 | 8/1997 | (WO) . |
| WO 97/27857 | 8/1997 | (WO) . |
| WO 97/28115 | 8/1997 | (WO) . |
| WO 97/28137 | 8/1997 | (WO) . |
| WO 97/28149 | 8/1997 | (WO) . |

OTHER PUBLICATIONS

J. Med. Chem. 1994, vol. 37, pp. 3977–3985 (Cantello, et al).

Current Pham. Design, 1996, vol. 2, pp. 85–102 (Hulin, et al.).

Chem. Pharm. Bull. 30(10) pp. 3601–3616 (1982) Sohda, et al.

J. Med. Chem. 1996, vol. 39, pp. 665–668 Willson, et al.

Chem. Pharm. Bull 30(10) pp. 3580–3600 (1982) Sohda, et al.

J. Med. Chem. 1986, vol. 29, pp. 770–778 Schnur, et al.

*Primary Examiner*—Robert Gerstl
(74) *Attorney, Agent, or Firm*—James L. McGinnis; Mollie M. Yang; David L. Rose

(57) ABSTRACT

Substituted 5-aryl-2,4-thiazolidinediones are potent agonists of PPAR, and are therefore useful in the treatment, control or prevention of diabetes, hyperglycemia, hyperlipidemia (including hypercholesterolemia and hypertriglyceridemia), atherosclerosis, obesity, vascular restenosis, and other PPAR $\alpha$, $\delta$ and/or $\gamma$ mediated diseases, disorders and conditions.

7 Claims, No Drawings

ARYLTHIAZOLIDINEDIONE DERIVITIVES

CROSS REFERENCE TO RELATED APPLICATIONS

This is a division of application Ser. No. 09/213,542 filed Dec. 17, 1998 now U.S. Pat. No. 6,008,237. Which is based on, and claims priority from, provisional applications No. 60/068,271, filed Dec. 19, 1997, and No. 60/105,238, filed Oct. 22, 1998, which are hereby incorporated by reference in their entirety.

SUMMARY OF THE INVENTION

The instant invention is concerned with arylthiazolidinediones and pharmaceutically acceptable salts thereof, which are useful as therapeutic compounds. Thus, it is an object of this invention to describe such compounds, processes for their preparation, methods of using such compounds, and compositions containing such compounds. Further objects will become apparent from reading the following description.

BACKGROUND OF THE INVENTION

Diabetes refers to a disease process derived from multiple causative factors and characterized by elevated levels of plasma glucose or hyperglycemia. Uncontrolled hyperglycemia is associated with increased and premature mortality due to an increased risk for microvascular and macrovascular diseases, including nephropathy, neuropathy, retinopathy, hypertension, stroke, and heart disease. Therefore, control of glucose homeostasis is critically important approach for the treatment of diabetes.

There are two generally recognized forms of diabetes. In type I diabetes, or insulin-dependent diabetes mellitus (IDDM), patients produce little or no insulin, the hormone which regulates glucose utilization. In type II diabetes, or noninsulin dependent diabetes mellitus (NIDDM), patients often have plasma insulin levels that are the same or even elevated compared to nondiabetic humans; however, these patients have developed a resistance to the insulin stimulating effect on glucose and lipid metabolism in the main insulin-sensitive tissues, muscle, liver and adipose tissue and the plasma insulin levels are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in liver.

The common treatments for NIDDM, which have not changed substantially in many years, are all with limitations. While physical exercise and reductions in dietary intake of calories will dramatically improve the diabetic condition, compliance with this treatment is very poor because of well-entrenched sedentary lifestyles and excess food consumption, especially of high fat-containing food. Increasing the plasma level of insulin by administration of sulfonylureas (e.g. tolbutamide, glipizide) which stimulate the pancreatic β-cells to secrete more insulin or by injection of insulin after the response to sulfonylureas fails will result in high enough insulin concentrations to stimulate the very insulin-resistant tissues. However, dangerously low levels of plasma glucose can result from these last two treatments and increasing insulin resistance due to the even higher plasma insulin levels could occur. The biguanides increase insulin sensitivity resulting in some correction of hyperglycemia. However, the two biguanides, phenformin and metformin, can induce lactic acidosis and nausea/diarrhea, respectively.

The glitazones (i.e. 5-benzylthiazolidine-2,4-diones) are a more recently described class of compounds with potential for a novel mode of action in ameliorating many symptoms of NIDDM. These agents substantially increase insulin sensitivity in muscle, liver and adipose tissue in several animal models of NIDDM resulting in complete correction of the elevated plasma levels of glucose, triglycerides and nonesterified fatty acids without occurrence of hypoglycemia.

Hyperlipidemia is a condition which is characterized by an abnormal increase in serum lipids, such as cholesterol, triglycerides and phospholipids. These lipids do not circulate freely in solution in plasma, but are bound to proteins and transported as macromolecular complexes called lipoproteins. See the *Merck Manual*, 16th Ed. 1992 (see for example pp. 1039–1040) and "Structure and Metabolism of Plasma Lipoproteins" in *Metabolic Basis of Inherited Disease*, 6th Ed. 1989, pp. 1129–1138.

One form of hyperlipidemia is hypercholesterolemia, characterized by the existence of elevated LDL cholesterol levels. The initial treatment for hypercholesterolemia is often to modify the diet to one low in fat and cholesterol, coupled with appropriate physical exercise, followed by drug therapy when LDL-lowering goals are not met by diet and exercise alone. LDL is commonly known as the "bad" cholesterol, while HDL is the "good" cholesterol. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., Am. J. Med., 62, 707–714 (1977); Stampfer, et al., N. England J. Med., 325, 373–381 (1991); and Kannel, et al., Ann. Internal Med., 90, 85–91 (1979). An example of an HDL raising agent is nicotinic acid, but the quantities needed to achieve HDL raising are associated with undesirable effects, such as flushing.

Peroxisome proliferators are a structurally diverse group of compounds that when administered to rodents elicit dramatic increases in the size and number of hepatic and renal peroxisomes, as well as concomitant increases in the capacity of peroxisomes to metabolize fatty acids via increased expression of the enzymes of the beta-oxidation cycle. Compounds of this group include but are not limited to the fibrate class of hyperlipidemic drugs, herbicides and phthalate plasticizers. Peroxisome proliferation is also triggered by dietary or physiological factors such as a high-fat diet and cold acclimatization.

Three sub-types of peroxisome proliferator activated receptor (PPAR) have been discovered and described; they are peroxisome proliferator activated receptor alpha (PPARα), peroxisome proliferator activated receptor gamma (PPARγ) and peroxisome proliferator activated receptor delta (PPARδ). Identification of PPARα, a member of the nuclear hormone receptor superfamily activated by peroxisome proliferators, has facilitated analysis of the mechanism by which peroxisome proliferators exert their pleiotropic effects. PPARα is activated by a number of medium and long-chain fatty acids, and it is involved in stimulating β-oxidation of fatty acids. PPARα is also involved with the activity of fibrates and fatty acids in rodents and humans. Fibric acid derivatives such as clofibrate, fenofibrate, bezafibrate, ciprofibrate, beclofibrate and etofibrate, as well as gemfibrozil, produce a substantial reduction in plasma triglycerides along with moderate reduction in LDL cholesterol, and they are used particularly for the treatment of hypertriglyceridemia.

The PPARγ receptor subtypes are involved in activating the program of adipocyte differentiation and are not involved in stimulating peroxisome proliferation in the liver. There are two isoforms of PPARγ: PPARγ1 and PPARγ2, which differ only in that PPARγ2 contains an additional 28 amino acids present at the amino terminus. The DNA sequences for the isotypes are described in Elbrecht, et al., BBRC 224;431–437 (1996). In mice, PPARγ2 is expressed specifically in fat cells. Tontonoz et al., Cell 79: 1147–1156 (1994) provide evidence to show that one physiological role of PPARγ2 is to induce adipocyte differentiation. As with other members of the nuclear hormone receptor superfamily, PPARγ2 regulates the expression of genes through interaction with other proteins and binding to hormone response elements for example in the 5' flanking regions of responsive genes. An example of a PPARγ2 responsive gene is the tissue-specific adipocyte P2 gene. Although peroxisome proliferators, including the fibrates and fatty acids, activate the transcriptional activity of PPAR's, only prostaglandin $J_2$ derivatives have been identified as natural ligands of the PPARγ subtype, which also binds thiazolidinedione antidiabetic agents with high affinity.

The human nuclear receptor gene PPARδ (hPPARδ) has been cloned from a human osteosarcoma cell cDNA library and is fully described in A. Schmidt et al., Molecular Endocrinology, 6 :1634–1641 (1992), herein incorporated by reference. It should be noted that PPARδ is also referred to in the literature as PPARβ and as NUC1, and each of these names refers to the same receptor; in Schmidt et al. the receptor is referred to as NUC1.

In WO96/01430, a human PPAR subtype, hNUC1B, is disclosed. The amino acid sequence of hNUC1B differs from human PPARδ (referred to therein as hNUC1) by one amino acid, i.e., alanine at position 292. Based on in vivo experiments described therein, the authors suggest that hNUC1B protein represses hPPARa and thyroid hormone receptor protein activity.

It has been disclosed in WO97/28149 that agonists of PPARδ are useful in raising HDL plasma levels. WO97/27857, 97/28115, 97/28137 and 97/27847 disclose compounds that are useful as antidiabetic, antiobesity, antiatherosclerosis and antihyperlipidemic agents, and which may exert their effect through activation of PPARs.

It has been suggested that glitazones exert their effects by binding to the peroxisome proliferator activated receptor (PPAR) family of receptors, controlling certain transcription elements having to do with the biological entities listed above. See Hulin et al., Current Pharm. Design (1996) 2, 85–102. The glitazones have been shown to bind exclusively to the PPARγ subtype.

All the glitazones that have progressed to clinical trials in human, and almost all of the glitazones that have been reported in the literature have the molecular motif of an aryl group attached to the 5-position of thiazolidinedione via a one carbon spacer. Although several compounds having a 4-(oxy)phenyl group directly attached to the 5-position of thiazolidinedione have been prepared and tested as potential antidiabetic agents, they have been stated to lack hypoglycemic activity.

Thus, the compound 5-[4-[2-(2-benzoxazolylmethylamino) ethoxy]phenyl]-2,4-thiazolidinedione (1) showed no antihyperglycemic activity in ob/ob mice, and subsequent studies showed this compound to require relatively high amounts for PPARγ activation. (Cantello et al, J. Med. Chem., 1994, 37:3977–3985 and Willson et al, J. Med. Chem., 1996, 39:665–668).

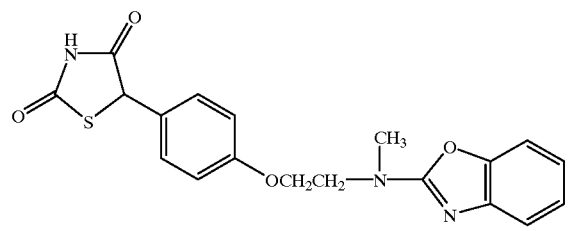

1

The compound 5-[4-(phenylethoxy)phenyl]-2,4-thiazolidinedione (2) showed no antihyperglycemic effect in diabetic mouse model, even though it may have aldose reductase inhibitory activity. (Sohda et al, Chem. Pharm. Bull., 1982, 30:3580–3600, and Sohda et al, Chem. Pharm. Bull., 1982, 30:3601–3616). Examples of other phenylthiazolidinedione aldose reductase inhibitors include 5-[4-(4-chlorophenoxy)phenyl]-2,4-thiazolidinedione, 5-[4-(4-chlorobenzyloxy)phenyl)-2,4-thiazolidinedione, 5-[4-(2-pyridylethoxy)phenyl]-2,4-thiazolidinedione, 5-[4-(6-methyl-2-pyridylethoxy)phenyl]-2,4-thiazolidinedione, and 5-[4-(2-thienylethoxy)phenyl]-2,4-thiazolidinedione. (Sohda et al, Chem. Pharm. Bull., 1982, 30:3601–3616).

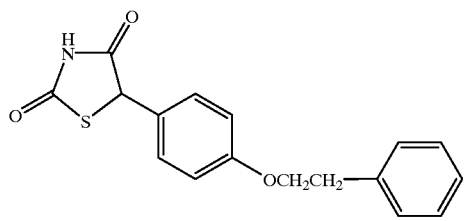

2

PCT Published Application WO97/22600 discloses antihyperglycemic 5-[3-(carboxamido)phenyl]-2,4-thiazolidinediones of the formula

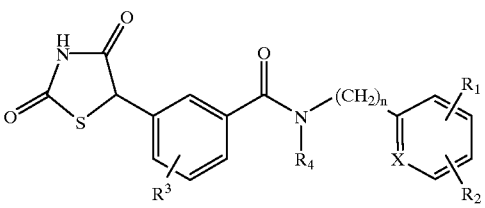

The present inventors have found that certain substituted 5-aryl-2,4-thiazolidinediones are potent agonists of PPAR, in particular the α, δ and/or γ subtypes, and especially the γ subtype including dual agonists of the α/γ subtypes. These compounds are therefore useful in the treatment, control or prevention of diabetes, hyperglycemia, hyperlipidemia (including hypercholesterolemia and hypertriglyceridemia), atherosclerosis, obesity, vascular restenosis, and other PPAR α, δ and/or γ mediated diseases, disorders and conditions.

DETAILED DESCRIPTION OF THE INVENTION

The present invention provides compounds having the formula I:

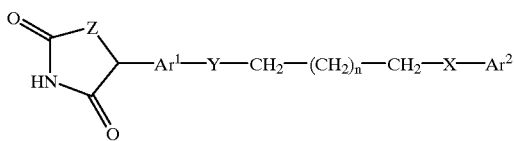

I wherein
Ar$^1$ is (1) arylene or
 (2) heteroarylene,
  wherein arylene and heteroarylene are optionally substituted with from 1 to 4 groups selected from R$^a$;
Ar$^2$ is (1) ortho-substituted aryl or
 (2) ortho-substituted heteroaryl,
  wherein said ortho substituent is selected from R; and aryl and heteroaryl are optionally further substituted with from 1–4 groups independently selected from R$^a$;
X and Y are independently O, S, N—R$^b$, or CH$_2$;
Z is O or S;
n is 0 to 3;
R is (1) C$_{3-10}$alkyl optionally substituted with 1–4 groups selected from halo and C$_{3-6}$cycloalkyl,
 (2) C$_{3-10}$alkenyl, or
 (3) C$_{3-8}$cycloalkyl;
R$^a$ is (1) C$_{1-5}$ alkanoyl,
 (2) C$_{1-5}$ alkyl,
 (3) C$_{2-15}$ alkenyl,
 (4) C$_{2-15}$ alkynyl,
 (5) halo,
 (6) OR$^b$,
 (7) aryl, or
 (8) heteroaryl,
  wherein said alkyl, alkenyl, alkynyl, and alkanoyl are optionally substituted with from 1–5 groups selected from R$^c$, and said aryl and heteroaryl optionally substituted with 1 to 5 groups selected from R$^d$;
R$^b$ is (1) hydrogen,
 (2) C$_{1-10}$alkyl,
 (3) C$_{2-10}$alkenyl,
 (4) C$_{2-10}$alkynyl,
 (5) aryl,
 (6) heteroaryl,
 (7) aryl C$_{1-15}$ alkyl,
 (8) heteroaryl C$_{1-5}$ alkyl,
 (9) C$_{1-5}$ alkanoyl,
 (10) C$_{3-8}$cycloalkyl,
  wherein alkyl, alkenyl, alkynyl are optionally substituted with one to four substituents independently selected from R$^c$, and cycloalkyl, aryl and heteroaryl are optionally substituted with one to four substituents independently selected from R$^d$; or
R$^c$ is (1) halo,
 (2) aryl,
 (3) heteroaryl,
 (4) CN,
 (5) NO$_2$,
 (6) OR$^f$,
 (7) S(O)$_m$R$^f$, m=0, 1 or 2, provided that R$^f$ is not H when m is 1 or 2;
 (8) NR$^f$R$^f$,
 (9) NR$^f$COR$^f$,
 (10) NR$^f$CO$_2$R$^f$,
 (11) NR$^f$CON(R$^f$)$_2$,
 (12) NR$^f$SO$_2$R$^f$, provided that R$^f$ is not H,
 (13) COR$^f$,
 (14) CO$_2$R$^f$,
 (15) CON(R$^f$)$_2$,
 (16) SO$_2$N(R$^f$)$_2$,
 (17) OCON(R$^f$)$_2$, or
 (18) C$_{3-8}$cycloalkyl,
  wherein said cycloalkyl, aryl and heteroaryl are optionally substituted with 1 to 3 groups of halo or C$_{1-6}$ alkyl;
R$^d$ is (1) a group selected from R$^c$,
 (2) C$_{1-10}$alkyl,
 (3) C$_{2-10}$ alkenyl,
 (4) C$_{2-10}$ alkynyl,
 (5) aryl C$_{1-10}$alkyl, or
 (6) heteroaryl C$_{1-10}$ alkyl,
  wherein alkyl, alkenyl, alkynyl, aryl, heteroaryl are optionally substituted with a group independently selected from R$^e$;
R$^e$ is (1) halogen,
 (2) amino,
 (3) carboxy,
 (4) C$_{1-4}$alkyl,
 (5) C$_{1-4}$alkoxy,
 (6) hydroxy,
 (7) aryl,
 (8) aryl C$_{1-4}$alkyl, or
 (9) aryloxy;
R$^f$ is (1) hydrogen,
 (2) C$_{1-10}$alkyl,
 (3) C$_{2-10}$alkenyl,
 (4) C$_{2-10}$alkynyl,
 (5) aryl,
 (6) heteroaryl,
 (7) aryl C$_{1-15}$ alkyl,
 (8) heteroaryl C$_{1-15}$ alkyl,
 (9) C$_{1-15}$ alkanoyl,
 (10) C$_{3-8}$cycloalkyl;
  wherein alkyl, alkenyl, alkynyl, aryl, heteroaryl, alkanoyl and cycloalkyl are optionally substituted with one to four groups selected from R$^e$;
or a pharmaceutically acceptable salt thereof.

In one subset of compounds of formula I Z is sulfur.

In another subset of compounds of formula I Ar$^1$ is arylene optionally substituted with 1–4 groups selected from R$^a$. Preferred Ar$^1$ is phenylene optionally substituted with 1–2 groups selected from halogen and C$_{1-4}$alkyl. More preferred Ar$^1$ is phenylene.

In another subset of compounds of formula I X and Y are each CH$_2$, O or S. Preferably X and Y are each O.

In another subset of compounds of formula I Ar$^2$ is

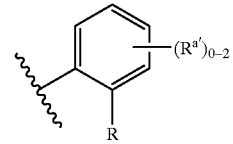

wherein R is C$_{3-4}$alkyl optionally substituted with one to four groups selected from halo and C$_{3-6}$cycloalkyl, and R$^{a'}$ is selected from R$^a$, or 2 R$^{a'}$ groups on adjacent carbon atoms taken together complete a 5- or 6-membered aromatic ring containing 0–2 heteroatoms selected from N, O and S(O)m (m is 0–2), said ring being optionally substituted with 1–2 groups selected from $R^a$. In a preferred subset, $R^{a'}$ is selected from $OR^b$, aryl optionally substituted with 1 to 5 groups independently selected from $R^d$, and $C_{1-15}$ alkyl optionally substituted with 1 to 5 groups independently selected from $R^c$. In another preferred subset, 2 $R^{a'}$ groups on adjacent carbon atoms taken together complete a 5- or 6-membered aromatic ring containing 1–2 heteroatoms selected from N, O and S(O)m (m is 0–2), said ring being optionally substituted with 1–2 groups selected from $R^a$. In a more preferred subset, $R^{a'}$ is selected from O-phenyl in which phenyl is optionally substituted with 1 to 4 groups selected from $R^d$, phenyl optionally substituted with 1 to 2 halogen, and $C_{1-5}$ alkyl optionally substituted with 1 to 5 groups independently selected from halogen, phenyl, and $C_{3-8}$cycloalkyl. In another more preferred subset 2 $R^{a'}$ groups on adjacent carbon atoms taken together complete a 5- or 6-membered aromatic ring selected from isoxazole, thiophene (S-oxide and S-dioxide), furan each of which is optionally substituted with 1 to 2 groups selected from $R^a$.

In another subset of compounds of formula I n is 1 or 2.

A preferred embodiment of formula I are compounds of formula Ia:

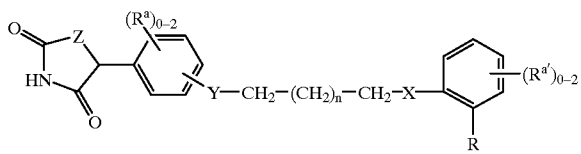

Ia wherein
$R^{a'}$ is selected from $R^a$, or 2 $R^{a'}$ groups on adjacent carbon atoms taken together complete a 5- or 6-membered aromatic ring containing 0–2 heteroatoms selected from N, O and S(O)m (m is 0–2), said ring being optionally substituted with 1–2 groups selected from $R^a$;
X, Y, Z, n, R, and $R^a$ are as defined under formula I.

In one subset of compounds of formula Ia are compounds of formula Ia(i):

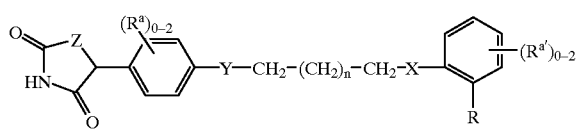

Ia(i)

In another subset of compounds of formula Ia are compounds of formula Ia(ii):

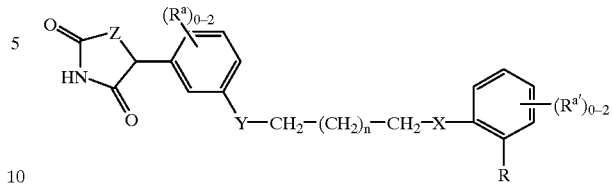

Ia(ii)

A more preferred embodiment are compounds of formula Ia wherein Z is S.

Another more preferred embodiment are compounds of formula Ia wherein Y is S or O, and X is O.

Another more preferred embodiment are compounds of formula Ia wherein R is $C_{3-4}$alkyl.

Another more preferred embodiment are compounds of formula Ia wherein n is 1 or 2.

Another more preferred embodiment are compounds of formula Ia wherein $R^{a'}$ is O-aryl optionally substituted with 1 to 3 groups independently selected from $R^d$, aryl optionally substituted with 1–3 groups selected from $R^d$, or $C_{1-5}$alkyl optionally substituted with 1–5 groups selected from $R^c$, or 2 $R^{a'}$ groups on adjacent carbon atoms taken together complete a 5- or 6-membered aromatic ring containing 0–2 heteroatoms selected from N, O and S(O)m (m is 0–2), said ring being optionally substituted with 1–2 groups selected from $R^a$.

An even more preferred embodiment are compounds of formula Ia wherein

Z is S;

X is O;

Y is (1) O or
  (2) S;

R is $C_{3-4}$ alkyl;

$R^a$ is (1) halogen or
  (2) $C_{1-5}$ alkyl;

$R^{a'}$ is (1) O-aryl optionally substituted with 1 to 3 groups independently selected from $R^d$,
  (2) aryl optionally substituted with 1–3 groups selected from $R^d$,
  (3) $C_{1-5}$alkyl optionally substituted with 1–5 groups selected from $R^c$, or
  2 $R^{a'}$ groups on adjacent carbon atoms taken together complete a 5- or 6-membered aromatic ring containing 0–2 heteroatoms selected from N, O and S(O)m (m is 0–2), said ring being optionally substituted with 1–2 groups selected from $R^a$.

Representative compounds of the present invention include those shown in Tables 1–3:

TABLE 1

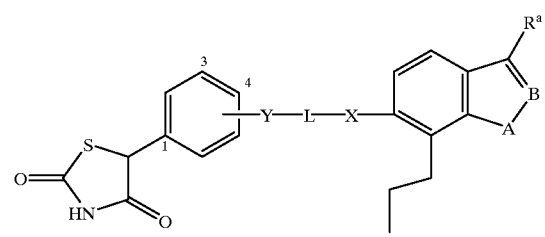

| * | Y—L—X | A/B | R$^a$ |
|---|---|---|---|
| 4 | O(CH$_2$)$_3$O | O/CH | Ph |
| 4 | O(CH$_2$)$_3$O | O/CH | CH$_2$C(CH$_3$)$_3$ |
| 3 | O(CH$_2$)$_4$O | O/CH | CH$_2$C(CH$_3$)$_3$ |
| 3 | O(CH$_2$)$_4$O | O/CH | (CH$_2$)$_2$Ph |
| 4 | O(CH$_2$)$_3$O | O/N | Ph |
| 4 | O(CH$_2$)$_3$O | O/N | CH$_2$C(CH$_3$)$_3$ |
| 4 | O(CH$_2$)$_3$O | O/N | CF$_3$ |
| 4 | O(CH$_2$)$_3$O | O/N | (CH$_2$)$_2$Ph |
| 4 | O(CH$_2$)$_3$O | O/N | (CH$_2$)$_4$Ph |
| 4 | O(CH$_2$)$_3$O | O/N | CH$_2$-c-Hex** |
| 4 | O(CH$_2$)$_3$O | O/N | CH$_2$C(CH$_3$)$_2$Ph |
| 3 | O(CH$_2$)$_4$O | O/N | CF$_3$ |
| 4 | O(CH$_2$)$_3$O | S/CH | (CH$_2$)$_2$Ph |
| 3 | O(CH$_2$)$_4$O | S/CH | (CH$_2$)$_2$Ph |
| 3 | O(CH$_2$)$_4$O | SO/CH | (CH$_2$)$_2$Ph |
| 4 | O(CH$_2$)$_3$O | SO/CH | (CH$_2$)$_2$Ph |
| 4 | O(CH$_2$)$_3$O | SO$_2$/CH | Ph |
| 3 | O(CH$_2$)$_4$O | SO$_2$/CH | (CH$_2$)$_2$Ph |
| 4 | O(CH$_2$)$_3$O | SO$_2$/CH | (CH$_2$)$_2$Ph |

*point of attachment of Y to the phenyl ring.
**c-Hex is cyclohexyl.

TABLE 2

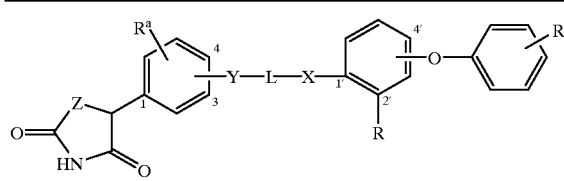

| Z | R$^a$ | * | Y—L—X | R | ** | R$^d$ |
|---|---|---|---|---|---|---|
| S | H | 4 | O(CH$_2$)$_3$O | propyl | 4' | H |
| S | 3-Cl | 4 | O(CH$_2$)$_3$O | propyl | 4' | H |
| S | 3-F | 4 | O(CH$_2$)$_3$O | propyl | 4' | H |
| S | 3-propyl | 4 | O(CH$_2$)$_3$O | propyl | 4' | H |
| S | 3-Cl | 4 | S(CH$_2$)$_3$O | propyl | 4' | H |
| S | 3-Cl | 4 | O(CH$_2$)$_4$O | propyl | 4' | H |
| S | 3-propyl | 4 | O(CH$_2$)$_4$O | propyl | 4' | H |
| S | H | 4 | O(CH$_2$)$_4$O | propyl | 4' | H |
| S | H | 3 | O(CH$_2$)$_3$O | propyl | 4' | H |
| S | H | 3 | O(CH$_2$)$_4$O | propyl | 4' | H |
| O | H | 3 | O(CH$_2$)$_3$O | propyl | 4' | H |
| O | H | 4 | O(CH$_2$)$_3$O | propyl | 4' | H |
| S | H | 4 | O(CH$_2$)$_3$O | propyl | 4' | 4-SO$_2$CH$_3$ |
| S | H | 4 | O(CH$_2$)$_3$O | propyl | 4' | 4-CH$_3$ |
| S | H | 4 | O(CH$_2$)$_3$O | propyl | 4' | 4-Cl |
| S | H | 4 | O(CH$_2$)$_3$O | propyi | 4' | 4-Ph |
| S | H | 3 | O(CH$_2$)$_3$O | propyl | 4' | 4-OCH$_3$ |
| S | H | 3 | O(CH$_2$)$_3$O | propyl | 4' | 4-F |
| S | H | 3 | (CH$_2$)$_4$O | propyl | 4' | H |
| S | H | 4 | (CH$_2$)$_4$O | propyl | 4' | 4-OCH$_3$ |
| S | H | 4 | (CH$_2$)$_4$O | propyl | 4' | 4-Cl |
| S | H | 3 | (CH$_2$)$_4$O | propyl | 4' | 4-Cl |
| S | H | 3 | (CH$_2$)$_5$O | propyl | 4' | H |
| S | H | 3 | (CH$_2$)$_5$O | propyl | 4' | 4-OCH$_3$ |
| S | H | 3 | (CH$_2$)$_5$O | propyl | 4' | 4-F |
| S | H | 3 | O(CH$_2$)$_5$ | propyl | 4' | 4-Ph |
| S | H | 4 | O(CH$_2$)$_4$ | propyl | 4' | 4-OCH$_3$ |

TABLE 2-continued

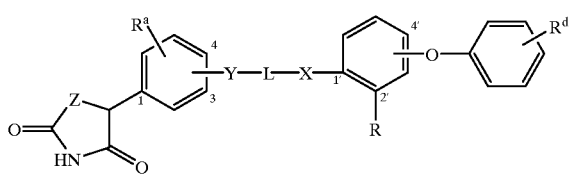

| Z | R$^a$ | * | Y—L—X | R | ** | R$^d$ |
|---|---|---|---|---|---|---|
| S | H | 3 | O(CH$_2$)$_4$ | propyl | 4' | 4-F |
| S | H | 3 | O(CH$_2$)$_5$ | propyl | 4' | 4-Cl |
| S | H | 3 | O(CH$_2$)$_3$O | propyl | 4' | 3-CH$_3$-4-Cl |
| S | H | 4 | O(CH$_2$)$_3$O | propyl | 4' | 4-CH$_2$CH(CH$_3$)$_2$ |
| S | H | 3 | O(CH$_2$)$_3$O | propyl | 4' | 4-c-pentyl |
| S | H | 3 | O(CH$_2$)$_3$O | propyl | 4' | 4-CH(CH$_3$)$_2$ |
| S | 3-propyl | 4 | O(CH$_2$)$_3$O | propyl | 4' | 4-OCH$_3$ |
| S | H | 4 | O(CH$_2$)$_4$O | propyl | 4' | 4-OCH$_3$ |
| S | H | 4 | o(CH$_2$)$_4$O | propyl | 4' | 4-F |
| S | H | 3 | O(CH$_2$)$_4$O | propyl | 4' | OCH$_3$ |
| S | H | 3 | O(CH$_2$)$_4$O | propyl | 4' | 4-Cl |
| S | H | 3 | O(CH$_2$)$_3$O | propyl | 4' | SO$_2$CH$_3$ |
| S | H | 3 | O(CH$_2$)$_3$O | propyl | 4' | 4-SO$_2$CH$_3$ |
| S | H | 4 | O(CH$_2$)$_3$O | propyl | 5' | H |
| S | H | 4 | O(CH$_2$)$_3$O | propyl | 3' | H |
| S | H | 3 | O(CH$_2$)$_4$O | propyl | 3' | H |
| S | H | 3 | O(CH$_2$)$_3$O | allyl | 4' | H |
| S | H | 3 | O(CH$_2$)$_3$O | 3-F-propyl | 4' | H |
| S | H | 3 | O(CH$_2$)$_3$O | propyl | 4' | 4-CO$_2$CH$_2$CH$_3$ |
| S | H | 4 | O(CH$_2$)$_3$O | propyl | 4' | 4-F |
| S | H | 4 | O(CH$_2$)$_3$O | propyl | 4' | 4-(4'-tolylsulfon-amide) |
| S | H | 3 | O(CH$_2$)$_3$O | c-pr-CH$_2$† | 4' | H |

*point of attachment of Y to the phenyl ring.
**point of attachment of the phenoxy group to the phenyl ring.
† c-pr is cyclopropyl

TABLE 3

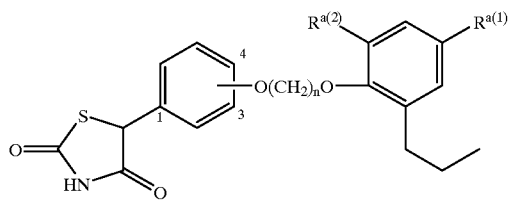

| * | n | R$^{a(1)}$ | R$^{a(2)}$ |
|---|---|---|---|
| 4 | 3 | 4-F-Ph | H |
| 3 | 3 | 2-naphthyloxy | H |
| 3 | 3 | 2-dibenzofuranyl | H |
| 3 | 3 | phenoxy | propyl |
| 4 | 3 | 3-isoxazolyl | H |
| 3 | 4 | 3-isoxazolyl | H |
| 4 | 3 | pyrazinyloxy | H |

*point of attachment of O to the phenyl ring.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic ring fused to an aryl group in which the point of attachment is on the non-aromatic portion. Examples of cycloalkyl include cyclopropyl, cyclopentyl, cyclohexyl, cycloheptyl, and the like.

"Aryl" (and "arylene") means mono- or bicyclic aromatic rings containing only carbon ring atoms. The term also includes aryl group fused to a monocyclic cycloalkyl or monocyclic heterocyclyl group in which the point(s) of attachment is on the aromatic portion.

"Heterocyclyl" means a fully or partially saturated ring containing at least one heteroatom selected from N, S and O, each of said ring having from 3 to 10 atoms. Examples of aryl include phenyl, naphthyl, indanyl, indenyl, tetrahydronaphthyl, 2,3-dihydrobenzofuranyl, benzopyranyl, 1,4-benzodioxanyl, and the like.

"Heteroaryl" (and heteroarylene) means a mono-, bi- or tricyclic aromatic ring containing at least one ring heteroatom selected from N, O and S (including SO and $SO_2$), with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, dibenzofuran and the like.

"Halogen" includes fluorine, chlorine, bromine and iodine.

The term "ortho-substituted" means the substituent is attached to a ring atom that is adjacent to the point of attachment to the backbone of the molecule.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Optical Isomers—Diastereomers—Geometric Isomers—Tautomers

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic, acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

Compounds of the present invention are potent agonists of varioius peroxisome proliferator activator receptor subtypes, particularly PPARα, PPARγ and/or PPARδ. Compounds of the present invention may be selective agonists of one receptor subtype, e.g. PPARγ agonists, or they may be agonists of more than one receptor subtypes, e.g. dual PPARα/γ agonists. Compounds of the present invention are useful in treating, controlling or preventing diseases, disorders or conditions mediated by the activation of an individual PPAR subtypes (α, δ or γ), or a combination of PPAR subtypes (e.g. α/γ). Thus one aspect of the present invention provides a method for the treatment, control or prevention of such diseases, disorders, or conditions in a mammal which comprises administering to such mammal a therapeutically effective amount of a compound of Formula I. The diseases, disorders or conditions for which compounds of the present invention are useful in treating, controlling or preventing include, but are not limited to, (1) diabetes mellitus, (2) hyperglycemia, (3) obesity, (4) hyperlipidemia, (5) hypertriglyceridemia, (6) hypercholesterolemia (including raising HDL levels), (7) atherosclerosis, (8) vascular restenosis, (9) irritable bowel syndrome, (10) pancreatitis, (11) abdominal obesity, (12) adipose cell tumors, (13) adipose cell carcinomas such as liposarcoma, and (14) other disorders where insulin resistance is a component including Syndrome X and ovarian hyperandrogenism (polycystic ovarian syndrome).

Another aspect of the invention provides a method for the treatment, control, or prevention of hypercholesterolemia which comprises administering to a mammal in need of such treatment a therapeutically effective amount of an agonist of both PPARα and PPARγ (PPARα/γ dual agonist). Preferably the dual agonist is administered with a cholesterol biosynthesis inhibitor, particularly an HMG-CoA reductase inhibitor such as lovastatin, simvastatin, pravastatin, fluvastatin, atorvastatin and rivastatin.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the-like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment, prevention, suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be combined with a compound of Formula I, either administered separately or in the same pharmaceutical compositions, include, but are limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide, or related materials;

(d) α-glucosidase inhibitors (such as acarbose), (e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) inhibitors of cholesterol absorption for example beta-sitosterol and (acyl CoA:cholesterol acyltransferase) inhibitors for example melinamide and (vi) probucol;

(f) PPARδ agonists such as those disclosed in WO97/97/28149;

(g) antiobesity compounds such as fenfluramine, dexfenfluramine, phentiramine, sulbitramine, orlistat, neuropeptide Y5 inhibitors, and β$_3$ adrenergic receptor agonist;

(h) ileal bile acid transporter inhibitor.

BIOLOGICAL ASSAYS

A. White Adipose Tissue in vitro Assay

This assay measures the efficacy of the instant compounds to enhance the insulin activation of $^{14}$C-glucose incorporation into glycogen in white adipose tissue (WAT) in a 5 hour completely in vitro system. All procedures are performed in medium 199 containing 1% bovine serum albumen, 5 mM HEPES, and antibiotic (100 units/ml penicillin, 100 μg/ml streptomycin sulfate, 0.25 μg/ml amphotericin B), hereafter called culture medium. Epididimyl fat pads are minced with scissors into small fragments, approximately 1 mm in diameter. Minced WAT fragments (100 mg) are incubated in a total volume of 0.9 ml culture medium containing 1 mU/ml insulin and test compound in tissue culture incubator at 37° C. with 5% $CO_2$ with orbital shaking for 3 hours. $^{14}$C-labeled glucose is added and incubation continued for 2 hours. Tubes are centrifuged at low speed, infranatant is removed and 1 M NaOH is added. Incubation of alkali-treated WAT for 10 minutes at 60° C. solubilizes tissue. Resulting tissue hydrolyzate is applied to Whatman filter paper strips which are then rinsed in 66% ethanol followed by 100% acetone which removes unincorporated $^{14}$C-glucose from bound $^{14}$C-glycogen. The dried paper is then incubated in solution of amyloglucosidase to cleave glycogen into glucose. Scintillation fluid is added and samples are counted for $^{14}$C activity. Test compounds that resulted in $^{14}$C activity substantially above incubations with insulin alone are considered active insulin-enhancing agents. Active compounds were titrated to determine the compound concentration which resulted in 50% of maximum enhancement of insulin activation and were termed $EC_{50}$ values.

B. Gal-4 hPPAR Transactivation Assays (a) Plasmids

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5X)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter.

(b) Cell Culture and Transactivation Assays

COS-1 cells were seeded at $12 \times 10^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% $CO_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 gg of pUAS(5X)-tk-luc reporter vector and 0.0002 μg of pCMV-lacZ as an internal control for transactivation efficiency. Cells were incubated in the transfection mixture for 5 h at 37° C. in an atmosphere of 10% $CO_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

C. In Vivo Studies

Male db/db mice (10–11 week old C57Bl/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose)±test compound at the indicated dose. Drug suspensions were prepared daily. Plasma glucose, and triglyceride concentrations were determined from blood obtained by tail bleeds at 3–5 day intervals during the study period. Glucose, and triglyceride, determinations were performed on a Boehringer Mannheim Hitachi 911 automatic analyzer (Boehringer Mannheim, Indianapolis, Ind.) using heparinized plasma diluted 1:6 (v/v) with normal saline. Lean animals were age-matched heterozygous mice maintained in the same manner.

Compounds of formula I may be prepared according to the methods outlined in the schemes. The various variables in the schemes, unless otherwise specified, have the same meanings as defined above under formula I.

Scheme 1

$H_3COOC-CH_2-Ar^1-Y-CH_2-(CH_2)_n-CH_2-X-Ar^2$ (A1)

a. LiHMDS, THF, TMSCl, NBS
b. when Z = S, thiourea, methoxyethanol, HCl, reflux

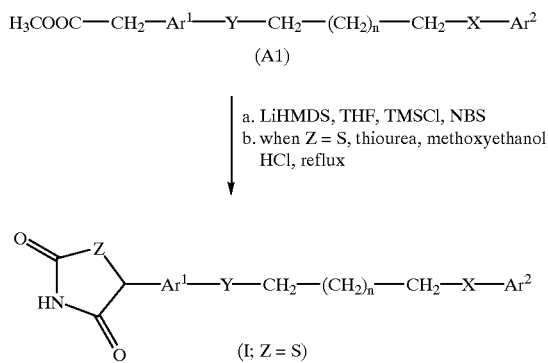

(I; Z = S)

Alpha-bromination of an arylacetate ester intermediate A1 with a halogenating agent (e.g. N-bromosuccinimide) in the presence of a base produces a halo intermediate which may be ring-closed with thiourea (Z=S) in the presence of aqueous strong acid or sodium acetate in an alcoholic solvent such as 2-methoxyethanol at elevated temperatures to give the title aryl-thiazolidinones (I; Z=S).

Scheme 2

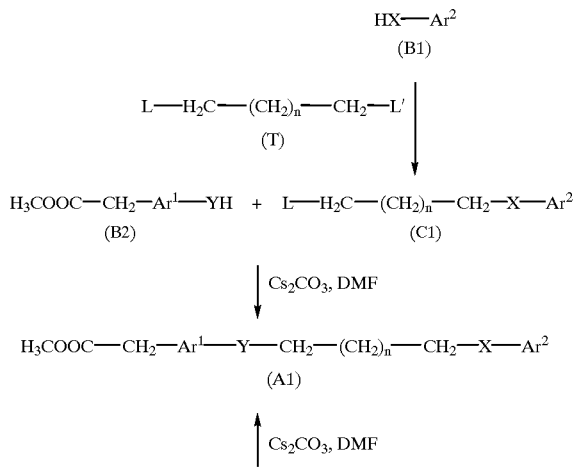

L and L' are same or different leaving groups

Scheme 2 shows the synthesis of intermediate A1, which contains an $Ar^1$ moiety and an $Ar^2$ moiety connected by a ≧4 atom tether. Intermediate A1 may be prepared by convergent synthesis by first attaching the tether T having two terminal leaving groups to either $Ar^1$ or $Ar^2$; in T, L and L' represent independently of each other a conventional leaving group such as halide (preferably bromide) and sulfonyloxy (e.g. mesylate or tosylate). Treatment of the tethered molecule C1 or C2 with the other aryl moiety B2 or B1, respectively in the presence of an inorganic base (e.g. $Cs_2CO_3$) in DMF solution provides the tethered arylacetate ester intermediate A1. The starting material T, B1, and B2 are either commercially available or may be prepared using known organic synthesis procedures. Compounds of formula B2 may be prepared according to the methods described in published PCT Applications 97/27857, 97/28115 and 97/28137.

Scheme 3

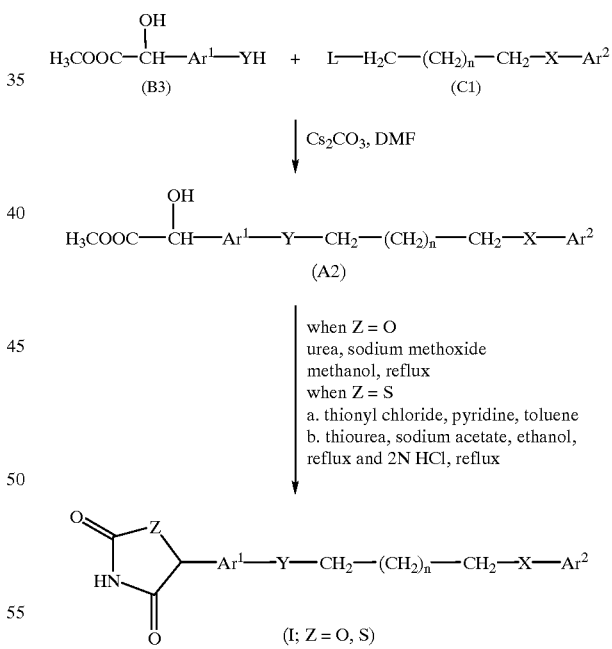

In Scheme 3 an appropriately substituted mandelic acid ester B3 is reacted with the $Ar^2$ derivative having a leaving group L, C1, in the presence of an inorganic base such as cesium carbonate. The resulting product A2 is cyclized with urea in the presence of a base such as sodium methoxide to form the desired product (I; Z=O). Alternatively, the hydroxy group of A2 may be converted to the corresponding chloride using thionyl chloride, and the resulting compound is ring-closed as described previously in Scheme 1 to provide compounds of formula I wherein Z=S. The starting materials for the synthesis depicted in Scheme 3 are either commercially available or may be prepared using known organic synthesis methodologies.

The following Examples are provided only to illustrate the invention and are not to be construed as limiting the invention in any manner.

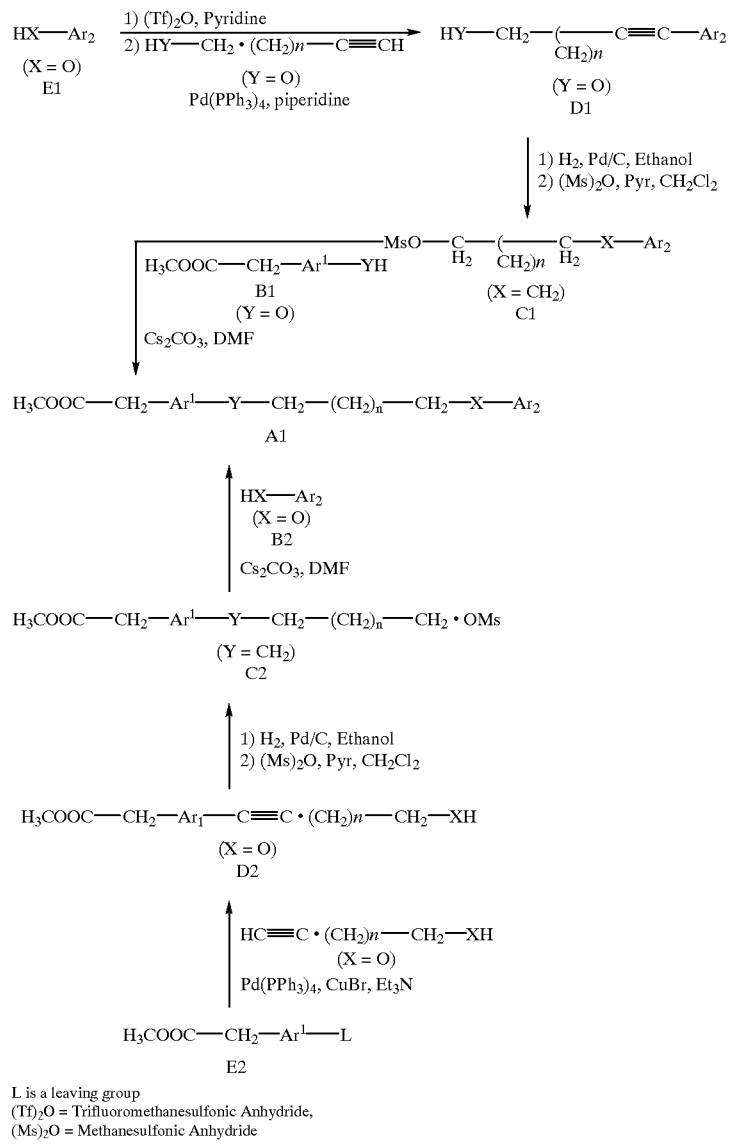

Scheme 4 shows the synthesis of intermediate A1, which contains an $Ar^1$ moiety and an $Ar^2$ moiety connected by a $\geq 4$ atom tether in which one of X or Y is oxygen. Palladium catalyzed addition of an alkyne to either an arylbromide (E1) or triflate (E2) gives D1 or D2, respectively. Hydrogenation of the alkyne (D1 or D2) at atmospheric pressure afforded the fully saturated material, C1 or C2, which was coupled to either B1 or B2 in the presence of an inorganic base (e.g. Cs2CO3) in dimethylformamide solution to provide the tethered arylacetate ester intermediate A1. The starting materials for the synthesis depicted in scheme 4 are either commercially available or may be prepared using known organic synthesis methodologies.

EXAMPLE 1
5-[4-(3-(2-propyl-4-phenoxy-phenoxypropoxy) phenyl]-2,4-thiazolidinedione

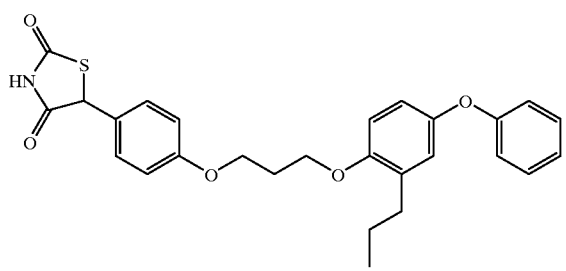

Step A: Preparation of Methyl 4-(3-bromopropoxy)phenylacetate

A solution of methyl 4-hydroxyphenylacetate (20.0 g, 0.12 mol), 1,3-dibromopropane (97.2 g, 0.48 mol) and cesium carbonate (43.1 g, 0.13 mol) in dry DMF (250 mL) was stirred at room temperature overnight. The reaction mixture was partitioned between ethyl acetate and 0.2N HCl. The organic layer was washed twice with water, then dried over sodium sulfate. The organic layer was filtered and evaporated to an oil which was chromatographed over silica gel with methylene chloride/hexane (2:1) to afford the title compound.

$^1$H NMR (400 MHz, CDCl$_3$): δ 7.17 (d, 2H, J=8.7 Hz), 6.84 (d, 2H, J=8.7 Hz), 4.07 (t,2H, J=5.8 Hz), 3.66 (s, 3H), 3.58 (t, 2H, J=6.5 Hz), 3.55 (s, 2H), 2.31 (quint, 2H, J=6.3 Hz).

Step B: Preparation of Methyl 4-(3-(2-propyl-4-phenoxyphenoxy)propoxy)phenylacetate A solution of the product from Step A (11.0 g, 38.58 mmol), 4-phenoxy-2-propylphenol (PCT Application WO97/28115; 8.0 g, 35.07 mmol) and cesium carbonate (12.0 g, 36.82 mmol) in DMF (80 mL) was stirred at 40° C. overnight. The reaction mixture was partitioned between ethyl acetate and 0.2N HCl. The organic layer was washed twice with water, then dried over sodium sulfate. The organic layer was filtered and evaporated to an oil which was chromatographed over silica gel with 10% of ethyl acetate in hexane to afford the title compound.

$^1$H NMR (400 MHz, CDCl$_3$): δ 7.30–7.18 (m, 4H), 7.02–6.70 (m, 8H), 4.17 (t, 2H, J=6.3 Hz), 4.11 (t, 2H, J=6.0 Hz), 2.53 (t, 2H, 7.4 Hz), 2.26 (quint, 2H, J=6.3 Hz), 1.55 (hex, 2H, 5.6 Hz), 0.89 (t, 3H, J=7.3 Hz).

Step C: Preparation of 5-[4-(3-(2-propyl-4-phenoxyphenoxy)propoxy)phenyl]-2,4-thiazolidinedione A solution of lithium bis(trimethylsilyl)amide (27.36 mL, 27.36 mmol) in dry THF (80 mL) was treated with trimethylsilyl chloride (5.94 mL, 46.76 mmol) at −78° C. To this mixture was added dropwise a solution of the product of Step B (10.80 g, 24.87 mmol) in THF (15 mL). The reaction mixture was stirred at −78° C. for 2 h. N-bromosuccinimide (4.65 g, 26.12 mmol) was added, and the mixture was allowed to warm to room temperature overnight. THF was evaporated and the residue was partitioned between ethyl acetate and water. The organic layer was washed once with water, then dried over sodium sulfate. The organic layer was filtered and evaporated to provide methyl α-bromo-4-(3-(2-propyl-4-phenoxy-phenoxy)propoxy)phenylacetate as an oil.

The residual oil was dissolved in methoxyethanol (100 mL); thiourea (2.84 g, 37.31 mmol) and sodium acetate (2.14 g, 26.12 mmol) were added. The mixture was heated at 115° C. for 5 h. Hydrochloric acid (19.43 mL, 6 N) was added, and the mixture was heated at 115° C. for 5 h. The mixture was partitioned between ethyl acetate and water. The organic layer was washed twice with water, dried over sodium sulfate, filtered and evaporated to an oil, which was chromatographed over silica gel with 1% of methanol in methylene chloride to afford the title compound.

$^1$H NMR (400 MHz, CDCl$_3$): δ 8.01 (brs, 1H), 7.32–7.24 (m, 4H), 7.02–6.79 (m,8H), 5.32 (s, 3H), 4.17 (t, 2H, J=6.3 Hz), 4.11 (t, 2H, J=6.0 Hz), 2.53 (t, 2H, 7.4 Hz), 2.26 (quint, 2H, J=6.3 Hz), 1.55 (hex, 2H, 5.6 Hz), 0.89 (t, 3H, J=7.3 Hz).

EXAMPLE 2

5-[4-(3-(7-propyl-3-phenyl-6-benz[4,5]isoxazolyloxy)propoxy)phenyl]-2,4-thiazolidinedione

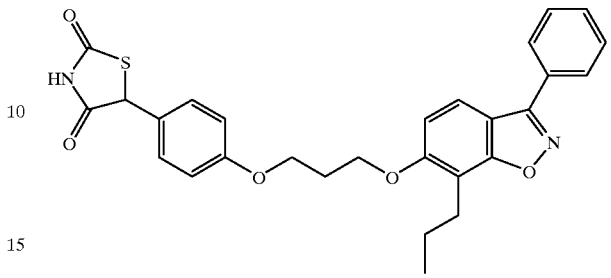

Step A: Preparation of Methyl 4-(3-(7-propyl-3-phenyl-6-benz[4,5]isoxazolyloxy)propoxy)phenylacetate The title compound was prepared according to the method described in Example 1, Step B, using 7-propyl-3-phenyl-6-hydroxy-benz-[4,5]-isoxazole (PCT Application WO97/28137) as the starting material.

$^1$H NMR (400 MHz, CDCl$_3$): δ 7.92 (dd, 2H, J=7.9, 2.6 Hz), 7.64 (d, 1H, J=8.7 Hz), 7.52 (m, 3H), 7.18 (d, 2H, J=8.6 Hz), 7.01 (d, 2H, J=8.8 Hz), 6.86 (dd, 2H, J=8.7, 2.1 Hz), 4.26 (t,2H, J=6.1 Hz), 4.18 (t, 2H, J=6.0 Hz), 3.67 (s, 3H), 3.55 (s, 2H), 2.90 (t, 2H, J=7.3 Hz), 2.31 (quint, 2H, J=6.3 Hz), 1.71 (hex, 2H, J=5.7 Hz), 0.92 (t, 3H, J=7.3 Hz).

Step B: Preparation of 5-[4-(3-(7-propyl-3-phenyl-6-benz[4,5]isoxazolyloxy)propoxy)phenyl]-2,4-thiazolidinedione The title compound was prepared according to the method described in Example 1, Step C, using methyl 4-(3-(7-propyl-3-phenyl-6-benz[4,5]isoxazolyloxy)propoxy)phenylacetate as the starting material.

$^1$H NMR (400 MHz, CDCl$_3$): δ 8.23 (brs, 1H), 7.92 (dd, 2H, J=7.9, 2.6 Hz), 7.64 (d, 1H, J=8.7 Hz), 7.52 (m, 3H), 7.31 (d, 2H, J=8.6 Hz), 6.98 (d, 2H, J=8.8 Hz), 6.92 (dd, 2H, J=8.7, 2.1 Hz), 4.26 (t,2H, J=6.1 Hz), 4.20 (t, 2H, J=6.0 Hz), 3.67 (s, 3H), 3.55 (s, 2H), 2.90 (t, 2H, J=7.3 Hz), 2.31 (quint, 2H, J=6.3 Hz), 1.71 (hex, 2H, J=5.7 Hz), 0.92 (t, 3H, J=7.3 Hz).

CI-MS: m/e=503 (M+1).

EXAMPLE 3

5-[4-(3-(7-propyl-3-neopentyl-6-benz[4,5]isoxazolyloxy)propoxy)phenyl]-2,4-thiazolidinedione

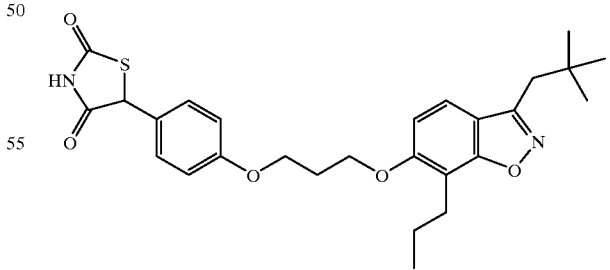

Step A: Preparation of Methyl 4-(3-(7-propyl-3-neopentyl-6-benz[4,5]isoxazolyloxy)propoxy)phenylacetate The title compound was prepared according to the method described in Example 1, Step B, using 7-propyl-3-neopentyl-6-hydroxy-benz[4,5]isoxazole (PCT Application WO97/28137) as the starting material.

¹H NMR (400 MHz, CDCl₃): δ 7.34 (d, 1H, J=8.7 Hz), 7.17 (dd, 2H, J=8.7, 2.1 Hz), 6.90 (d, 1H, J=8.7 Hz), 6.86 (dd, 2H, J=8.7, 2.1 Hz), 4.23 (t, 2H, J=6.0 Hz), 4.18 (t, 2H, J=6.0 Hz), 3.67 (s, 3H), 3.54 (s, 2H), 2.85 (t, 2H, J=7.2 Hz), 2.78 (s, 2H), 2.28 (quint, 2H, J=6.3 Hz), 1.66 (hex, 2H, J=5.9 Hz), 1.02 (s, 9H), 0.92 (t, 3H, J=7.3 Hz).

Step B: Preparation of 5-[4-(3-(7-propyl-3-neopentyl-6-benz[4,5]isoxazolyloxy)propoxy)phenyl]-2,4-thiazolidinedione The title compound was prepared according to the method described in Example 1, Step C, methyl 4-(3-(7-propyl-3-neopentyl-6-benz[4,5]isoxazolyloxy)propoxy)-phenylacetate as the starting material.

¹H NMR (400 MHz, CDCl₃): δ 8.10 (brs, 1H), 7.34–7.30 (m, 3H), 6.88–6.93 (m, 3H), 5.32 (s, 1H), 4.24–4.17 (m, 4H), 2.82 (t, 2H, J=7.2 Hz), 2.78 (s, 2H), 2.28 (quint, 2H, J=6.3 Hz), 1.66 (hex, 2H, J=5.9 Hz), 1.02 (s, 9H), 0.92 (t, 3H, J=7.3 Hz

EXAMPLE 4

5-[4-(3-(7-propyl-3-trifluoromethyl-6-benz[4,5]-isoxazolyloxy)propoxy)phenyl]-2,4-thiazolidinedione

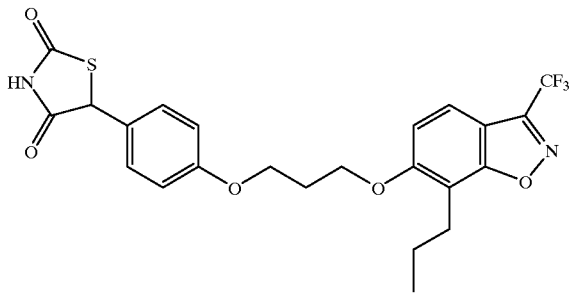

Step A: Preparation of Methyl 4-(3-(7-propyl-3-trifluoromethyl-6-benz[4,5]isoxazolyloxy)propoxy)-phenylacetate The title compound was prepared according to the method described in Example 1, Step B, using 7-propyl-3-trifluoromethyl-6-hydroxy-benz[4,5]isoxazole (PCT Application WO97/28137) as the starting material.

¹H NMR (400 MHz, CDCl₃): δ 7.53 (d, 1H, J=8.2 Hz), 7.18 (dd, 2H, J=8.7, 2.1 Hz), 7.05 (d, 1H, J=8.8 Hz), 6.86 (dd, 2H, J=8.7, 2.1 Hz), 4.27 (t, 2H, J=6.0 Hz), 4.18 (t, 2H, J=6.0 Hz), 3.65 (s, 3H), 3.54 (s, 2H), 2.88 (t, 2H, J=7.2 Hz), 2.30 (quint, 2H, J=6.3 Hz), 1.66 (hex, 2H, J=5.9 Hz), 0.92 (t, 3H, J=7.3 Hz).

Step B: Preparation of 5-[4-(3-(7-propyl-3-trifluoromethyl-6-benz[4,5]isoxazolyloxy)propoxy)phenyl]-2,4-thiazolidinedione The title compound was prepared according to the method described in Example 1, Step C, using methyl 4-(3-(7-propyl-3-trifluoromethyl-6-benz[4,5]isoxazolyloxy)propoxy)phenylacetate as the starting material.

¹H NMR (400 MHz, CDCl₃): δ 8.05 (brs, 1H), 7.53 (d, 1H, J=8.8 Hz), 7.32 (dd, 2H, J=8.7, 2.1 Hz), 7.06 (d, 1H, J=8.6 Hz), 6.92 (dd, 2H, J=8.7, 2.1 Hz), 5.32 (s, 1H), 4.27 (t, 2H, J=6.1 Hz), 4.18 (t, 2H, J=6.1 Hz), 2.85 (t, 2H, J=7.5 Hz), 2.28 (quint, 2H, J=6.3 Hz), 1.66 (hex, 2H, J=5.9 Hz), 0.92 (t, 3H, J=7.3 Hz).

CI-MS: m/e=512.3 (M+NH4).

EXAMPLE 5

5-[4-(3-(7-propyl-3-phenethyl-6-benz[4,5]isoxazolyloxy)propoxy)phenyl]-2,4-thiazolidinedione

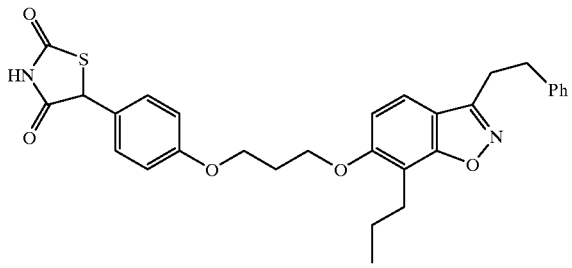

Step A: Preparation of methyl 4-(3-(7-propyl-3-phenethyl-6-benz[4,5]isoxazolyloxy)propoxy)phenylacetate The title compound was prepared according to the method described in Example 1, Step B, using 7-propyl-3-phenethyl-6-hydroxybenz-[4,5]-isoxazole (PCT Application WO97/28137) as the starting material.

¹H NMR (400 MHz, CDCl₃): δ 7.28–7.16 (m, 8H), 6.88–6.84 (m, 3H), 4.21 (t, 2H, J=6.0 Hz), 4.16 (t, 2H, J=6.0 Hz), 3.67 (s, 3H), 3.54 (s, 2H), 3.22–3.12 (m, 4H), 2.85 (t, 2H, J=7.2 Hz), 2.29 (quint, 2H, J=6.3 Hz), 1.66 (hex, 2H, J=5.9 Hz), 0.92 (t, 3H, J=7.3 Hz).

Step B: Preparation of 5-[4-(3-(7-propyl-3-phenethyl-6-benz[4,5]isoxazolyloxy)propoxy)phenyl]-2,4-thiazolidinedione The title compound was prepared according to the method described in Example 1, Step C, using methyl 4-(3-(7-propyl-3-trifluoromethyl-6-benz[4,5]isoxazolyloxy)propoxy)phenylacetate as the starting material.

¹H NMR (400 MHz, CDCl₃): δ 8.10 (brs, 1H), 7.32–7.19 (m, 8H), 6.93–6.86 (m, 3H), 4.23–4.17 (m, 4H), 3.22–3.10 (m, 4H), 2.85 (t, 2H, J=7.2 Hz), 2.29 (quint, 2H, J=6.3 Hz), 1.66 (hex, 2H, J=5.9 Hz), 0.92 (t, 3H, J=7.3 Hz).

CI-MS: m/e=531.5 (M+1).

EXAMPLE 6

5-[4-(3-(7-propyl-3-phenylbutyl-6-benz[4,5]isoxazolyloxy)propoxy)phenyl]-2,4-thiazolidinedione

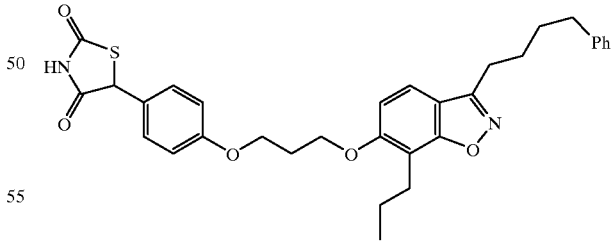

Step A: Preparation of Methyl 4-(3-(7-propyl-3-phenylbutyl-6-benz[4,5]isoxazolyloxy)propoxy)phenylacetate The title compound was prepared according to the method described in Example 1, Step B, using 7-propyl-3-phenylbutyl-6-hydroxybenz[4,5]isoxazole as the starting material.

¹H NMR (400 MHz, CDCl₃): δ 7.31 (d,1H, J=8.6 Hz), 7.26–7.13 (m, 8H), 6.88–6.84 (m, 2H), 4.21 (t, 2H, J=6.0

Hz), 4.16 (t, 2H, J=6.0 Hz), 3.67 (s, 3H), 3.54 (s, 2H), 2.91 (t, 2H, J=7.4 Hz), 2.82 (t, 2H, J=7.5 Hz), 2.66 (t, 2H, J=7.2 Hz), 2.29 (quint, 2H, J=6.3 Hz), 1.90–1.70 (m,4H), 1.66 (hex, 2H, J=5.9 Hz), 0.92 (t, 3H, J=7.3 Hz).

Step B: Preparation of 5-[4-(3-(7-propyl-3-phenylbutyl-6-benz[4,5]isoxazolyloxy)propoxy)phenyl]-2,4-thiazolidinedione The title compound was prepared according to the method described in Example 1, Step C, using methyl 4-(3-(7-propyl-3-phenylbutyl)-6-benz[4,5]isoxazolyloxy)propoxy)phenylacetate as the starting material.

$^1$H NMR (400 MHz, CDCl$_3$): δ 8.10 (brs, 1H), 7.32–7.29 (m,3H), 7.26–7.20 (m, 2H), 7.17–7.11 (m, 3H), 6.93–6.87 (m, 3H), 4.23–4.16 (m, 4H), 2.91 (t, 2H, J=7.4 Hz), 2.82 (t, 2H, J=7.5 Hz), 2.66 (t, 2H, J=7.2 Hz), 2.29 (quint, 2H, J=6.3 Hz), 1.90–1.70 (m,4H), 1.66 (hex, 2H, J=5.9 Hz), 0.92 (t, 3H, J=7.3 Hz)

CI-MS: m/e=559.7 (M+1).

EXAMPLE 7

5-[4-(3-(7-propyl-3-phenylbenzofuran-6-yl)oxy)propoxy)phenyl]-2,4-thiazolidinedione

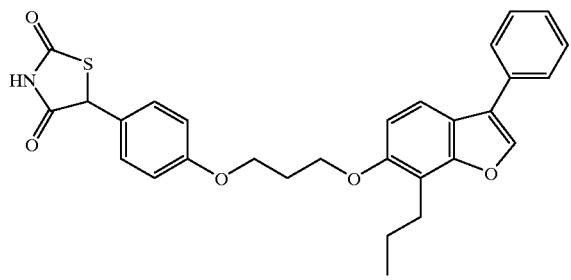

Step A: Preparation of Methyl 4-(3-(7-propyl-3-phenylbenzofuran-6-yl)propoxy)phenylacetate The title compound was prepared according to the method described in Example 1, Step B, using 6-hydroxy-7-propyl-3-phenylbenzofuran (PCT Application WO97/27857) as the starting material.

$^1$H NMR (400 MHz, CDCl$_3$): δ 7.69 (s, 1H), 7.68–7.59 (m, 2H), 7.54 (d,1H, J=8.5 Hz), 7.45–7.131 (m, 3H), 7.18–7.15 (m, 2H), 6.92 (d, 1H, J=8.5 Hz), 6.90–6.85 (m, 2H), 4.21–4.16 (m, 4H), 3.67 (s, 3H), 3.54 (s, 2H), 2.88 (t, 2H, J=7.4 Hz), 2.29 (quint, 2H, J=6.3 Hz), 1.66 (hex, 2H, J=5.9 Hz), 0.92 (t, 3H, J=7.3 Hz).

Step B: Preparation of 5-[4-(3-(7-propyl-3-phenyl-benzofuran-6-yl)propoxy)phenyl]-2,4-thiazolidinedione The title compound was prepared according to the method described in Example 1, Step C, using methyl 4-(3-(7-propyl-3-phenylbenzofuran-6-yl)propoxy)phenylacetate as the starting material.

$^1$H NMR (400 MHz, CDCl$_3$): δ 8.18 (brs, 1H), 7.69 (s, 1H), 7.63–7.59 (m, 2H), 7.55 (d,1H, J=8.5 Hz), 7.45–7.40 (m, 2H), 7.36–7.27 (m, 3H), 6.90–6.55 (m, 3H), 5.31 (s, 1H), 4.21–4.16 (m, 4H), 3.67 (s, 3H), 3.54 (s, 2H), 2.88 (t, 2H, J=7.4 Hz), 2.29 (quint, 2H, J=6.3 Hz), 1.66 (hex, 2H, J=5.9 Hz), 0.92 (t, 3H, J=7.3 Hz).

CI-MS: m/e=502.4 (M+1).

EXAMPLE 8

5-[4-(3-(7-propyl-3-phenylbenzothiophen-1,1-dioxide-6-yl)oxy)propoxy)phenyl]-2,4-thiazolidinedione

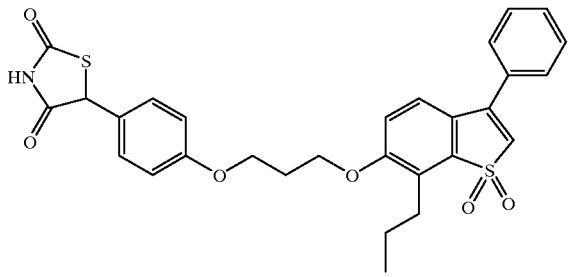

Step A: Preparation of Methyl 4-(3-(7-propyl-3-phenyl-benzothiophen-1,1-dioxide-6-yl)propoxy)phenylacetate The title compound was prepared according to the method described in Example 1, Step B, using 6-hydroxy-7-propyl-3-phenylbenzothiophen-1,1-dioxide as the starting material.

$^1$H NMR (400 MHz, CDCl$_3$): δ 7.50–7.42 (m, 4H), 7.31 (d,2H, J=8.8 Hz), 7.19–7.16 (d,2H, J=8.3 Hz), 6.92–6.83 (m, 3H), 6.46 (s, 1H), 4.21–4.16 (m, 4H), 3.67 (s, 3H), 3.54 (s, 2H), 2.95 (t, 2H, J=7.4 Hz), 2.29 (quint, 2H, J=6.3 Hz), 1.71 (hex, 2H, J=5.9 Hz), 1.01 (t, 3H, J=7.3 Hz).

Step B: Preparation of 5-[4-(3-(7-propyl-3-phenyl-benzothiophen-1,1-dioxide-6-yl)propoxy)phenyl]-2,4-thiazolidinedione The title compound was prepared according to the method described in Example 1, Step C, using methyl 4-(3-(7-propyl-3-phenylbenzothiophen-1,1-dioxide-6-yl)propoxy)phenylacetate as the starting material.

$^1$H NMR (400 MHz, CDCl$_3$): δ 8.05 (brs, 1H), 7.50–7.42 (m, 4H), 7.31 (d,2H, J=8.8 Hz), 7.19–7.16 (d,2H, J=8.3 Hz), 6.92–6.83 (m, 3H), 6.46 (s, 1H), 5.32 (s, 1H), 4.21–4.16 (m, 4H), 2.95 (t, 2H, J=7.4 Hz), 2.29 (quint, 2H, J=6.3 Hz), 1.71 (hex, 2H, J=5.9 Hz), 1.01 (t, 3H, J=7.3 Hz).

CI-MS: m/e=567.3 (M+NH4).

EXAMPLE 9

5-[4-(3-(7-propyl-3-cyclohexylmethyl-6-benz-[4,5]-isoxazolyloxy)propoxy)phenyl]-2,4-thiazolidinedione

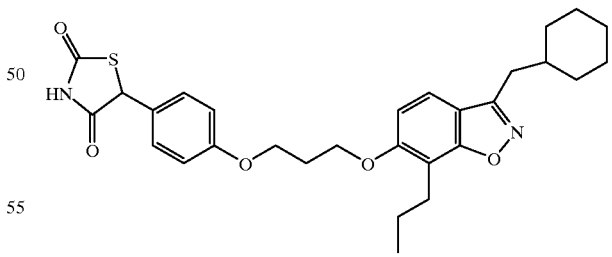

Step A: Preparation of Methyl 4-(3-(7-propyl-3-cyclohexylmethyl-6-benz[4,5]-isoxazolyloxy)propoxy)phenylacetate The title compound was prepared according to the method described in Example 1, Step B. using (3-cyclohexylmethyl-6-hydroxy-7-propy)benz[4,5]-isoxazole as the starting material.

$^1$H NMR (400 MHz, CDCl$_3$): δ 7.36 (d,1H, J=8.6 Hz), 7.32 (dd, 2H, J=6.7, 1.9 Hz), 6.93–6.88 (m, 3H), 4.23–4.17

(m, 4H), 3.84 (s, 3h), 3.72 (s, 2H), 2.84 (t, 2H, J=6.3 Hz), 2.77 (d, 2H, J=7.0 Hz), 2.29 (quint, 2H, J=6.3 Hz), 1.85–1.00 (m, 13H), 0.89 (t, 3H, J=7.3 Hz).

Step B: Preparation of 5-[4-(3-(7-propyl-3-cyclohexylmethyl-6-benz-[4,5]-isoxazolyloxy)propoxy)phenyl]-2,4-thiazolidinedione The title compound was prepared according to the method described in Example 1, Step C. using methyl 4-(3-(7-propyl-3-cyclohexanemethyl-6-benz[4,5]-isoxazolyloxy)propoxy)phenylacetate as the starting material.

¹H NMR (400 MHz, CDCl₃): δ 8.25 (s, 1H), 7.36 (d,1H, J=8.6 Hz), 7.32 (dd, 2H, J=6.7, 1.9 Hz), 6.93–6.88 (m, 3H), 5.32 (s, 1H), 4.23–4.17 (m, 4H), 2.84 (t, 2H, J=6.3 Hz), 2.77 (d, 2H, J=7.0 Hz), 2.29 (quint, 2H, J=6.3 Hz), 1.85–1.00 (m, 13H), 0.89 (t, 3H, J=7.3 Hz).

EXAMPLE 10

5-[4-(3-(2-propyl-4-(4'-fluorobiphenyloxy)propoxy)phenyl]-2,4-thiazolidinedione

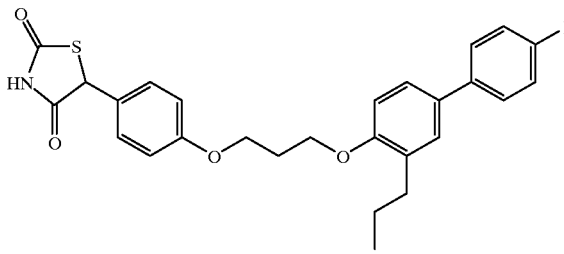

Step A: Preparation of Methyl 4-(3-(2-propyl-(4'-fluorobiphenyloxy)propoxy)phenylacetate The title compound was prepared according to the method described in Example 1, Step B, using 2-propyl-4-(4-fluorophenyl)-phenol as the starting material.

¹H NMR (400 MHz, CDCl₃): δ 7.32–7.24 (m, 4H), 7.02–6.79 (m,7H), 4.20–4.16 (m, 4H), 3.80 (s, 3h), 3.70 (s, 2H), 2.53 (t, 2H, 7.4 Hz), 2.26 (quint, 2H, J=6.3 Hz), 1.55 (hex, 2H, 5.6 Hz), 0.89 (t, 3H, J=7.3 Hz).

Step B: Preparation of 5-[4-(3-(2-propyl-(4'-fluorobiphenyloxy)propoxy)phenyl]-2,4-thiazolidinedione The title compound was prepared according to the method described in Example 1, Step C, using methyl 4-(3-(2-propyl-(4'-fluorobiphenyloxy)propoxy)phenylacetate as the starting material.

¹H NMR (400 MHz, CDCl₃): δ 8.01 (brs, 1H), 7.32–7.24 (m, 4H), 7.02–6.79 (m,7H), 5.32 (s, 3H), 4.20–4.16 (m, 4H), 2.53 (t, 2H, 7.4 Hz), 2.26 (quint, 2H, J=6.3 Hz), 1.55 (hex, 2H, 5.6 Hz), 0.89 (t, 3H, J=7.3 Hz).

EXAMPLE 11

5-[4-(3-(2-propyl-4-phenoxyphenoxy)propoxy)-3-chlorophenyl]-2,4-thiazolidinedione

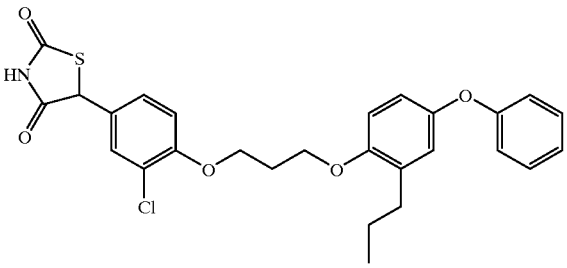

Step A: Preparation of 4-(3-bromopropoxy)-3-propylphenyl phenyl ether

A solution of 4-phenoxy-2-propylphenol (12.0 g, 52.60 mmol), 1,3-dibromopropane (31.86 g, 157.81 mmol) and cesium carbonate (18.0 g, 55.23 mmol) in dry DMF (110 mL) was stirred at room temperature overnight. The reaction mixture was partitioned between ethyl acetate and 0.2N HCl. The organic was washed twice with water, then dried over sodium sulfate. The organic was filtered and evaporated to an oil which was chromatographed over silica gel with methylene chloride/hexane (1:1) to afford the title compound.

Step B: Preparation of Methyl 4-(3-(2-propyl-4-phenoxyphenoxy)propoxy)-3-chlorophenylacetate A solution of the product from Step A (2.5 g, 7.18 mmol), methyl 3-chloro-4-hyrdoxyphenylacetate (1.42 g, 7.11 mmol) and cesium carbonate (2.43 g, 7.45 mmol) in DMF (20 mL) was stirred at 40° C. overnight. The reaction mixture was partitioned between ethyl acetate and 0.2N HCl. The organic was washed twice with water, then dried over sodium sulfate. The organic was filtered and evaporated to an oil which was chromatographed over silica gel with 10% of ethyl acetate in hexane to afford the title compound.

¹H NMR (400 MHz, CDCl₃): δ 7.24–7.29 (m, 3H), 7.10 (dd, 1H, J=8.4, 2.1 Hz), 7.00 (t, 1H, J=7.3 Hz), 6.92–6.80 (m, 6H), 4.22 (t, 2H, J=6.1 Hz), 4.16 (t, 2H, J=6.0 Hz), 3.67 (s, 3H), 3.52 (s, 2H), 2.53 (t, 2H, J=7.4 Hz), 2.30 (quint, 2H, J=6.3 Hz), 1.55 (hex, 2H, 5.6 Hz), 0.89 (t, 3H, J=7.3 Hz).

Step C: Preparation of 5-[4-(3-(2-propyl-4-phenoxyphenoxy)propoxy)-3-chlorophenyl]-2,4-thiazolidinedione The title compound was prepared according to the method described in Example 1, Step C, using methyl 4-(3-(2-propyl-4-phenoxyphenoxy)propoxy)-3-chlorophenylacetate as the starting material.

¹H NMR (400 MHz, CDCl₃): δ 8.46 (brs, 1H), 7.42 (d, 1H, J=2.3 Hz), 7.29–7.23 (m, 3H), 7.02–6.80 (m, 7H), 5.27 (s, 1H), 4.24 (t, 2H, J=6.1 Hz), 4.15 (t, 2H, J=6.0 Hz), 3.67 (s, 3H), 3.52 (s, 2H), 2.53 (t, 2H, J=7.4 Hz), 2.30 (quint, 2H, J=6.3 Hz), 1.55 (hex, 2H, 5.6 Hz), 0.89 (t, 3H, J=7.3 Hz).

EXAMPLE 12

5-[4-(3-(2-propyl-4-phenoxyphenoxy)propoxy)-3-fluorophenyl]-2,4-thiazolidinedione

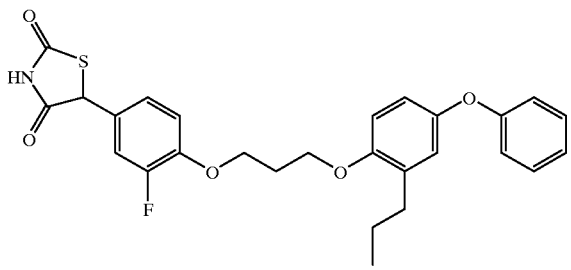

Step A: Preparation of methyl 4-(3-(2-propyl-4-phenoxyphenoxy)propoxy)-3-fluorophenylacetate The title compound was prepared according to the method described in Example 11, Step B, using methyl 3-fluoro-4-hydroxyphenylacetate as the starting material.

$^1$H NMR (400 MHz, CDCl$_3$): δ 7.23–7.28 (m, 3H), 7.11 (dd, 1H, J=8.4, 2.1 Hz), 7.03 (t, 1H, J=7.3 Hz), 6.92–6.82 (m, 6H), 4.24 (t, 2H, J=6.1 Hz), 4.14 (t, 2H, J=6.0 Hz), 3.66 (s, 3H), 3.52 (s, 2H), 2.51 (t, 2H, J=7.4 Hz), 2.31 (quint, 2H, J=6.3 Hz), 1.54 (hex, 2H, 5.6 Hz), 0.86 (t, 3H, J=7.3 Hz).

Step B: Preparation of 5-[4-(3-(2-propyl-4-phenoxyphenoxy)propoxy)-3-fluorophenyl]-2,4-thiazolidinedione The title compound was prepared according to the method described in Example 1, Step C, using methyl 4-(3-(2-propyl-4-phenoxyphenoxy)propoxy)-3-fluorophenylacetate as the starting material.

$^1$H NMR (400 MHz, CDCl$_3$): δ 7.98 (brs, 1H), 7.42 (d, 1H, J=2.3 Hz), 7.29–7.23 (m, 3H), 7.02–6.80 (m, 7H), 5.27 (s, 1H), 4.24 (t, 2H, J=6.1 Hz), 4.15 (t, 2H, J=6.0 Hz), 3.67 (s, 3H), 3.52 (s, 2H), 2.53 (t, 2H, J=7.4 Hz), 2.30 (quint, 2H, J=6.3 Hz), 1.55 (hex, 2H, 5.6 Hz), 0.89 (t, 3H, J=7.3 Hz).

EXAMPLE 13

5-[4-(3-(2-propyl-4-phenoxyphenoxy)propoxy)-3-propylphenyl]-2,4-thiazolidinedione

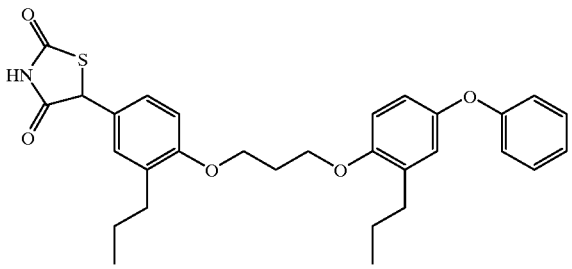

Step A: Preparation of methyl 4-(3-(2-propyl-4-phenoxyphenoxy)propoxy)-3-propylphenylacetate The title compound was prepared according to the method described in Example 11, Step B, using methyl 4-hydroxy-3-propylphenylacetate as the starting material.

$^1$H NMR (400 MHz, CDCl$_3$): δ 7.31–7.25 (m, 2H), 7.07–6.80 (m, 9H), 4.18–4.13 (m, 4H), 3.67 (s, 3H), 3.54 (s, 2H), 2.58–2.53 (m, 4H), 2.29 (quint, 2H, J=6.3 Hz), 1.61–1.55 (m, 4H,), 0.96–0.86 (m,6H).

Step B: Preparation of 5-[4-(3-(2-propyl-4-phenoxyphenoxy)propoxy)-3-propylphenyl]-2,4-thiazolidinedione The title compound was prepared according to the method described in Example 1, Step C, using methyl 4-(3-(2-propyl-4-phenoxyphenoxy)propoxy)-3-propylphenylacetate as the starting material.

$^1$H NMR (400 MHz, CDCl$_3$): δ 8.04 (brs, 1H), 7.28–7.24 (m, 2H), 7.18 (dd, 1H, J=8.4, 2.3 Hz), 7.12 (d, 1H, J=2.5 Hz), 7.00 (t, 1H, J=7.4 Hz), 6.92–6.79 (m, 6H), 5.30 (s, 1H), 4.18–4.13 (m, 4H), 2.58–2.53 (m, 4H), 2.29 (quint, 2H, J=6.3 Hz), 1.61–1.55 (m, 4H,), 0.96–0.86 (m,6H).

EXAMPLE 14

5-[4-(3-(2-propyl-4-phenoxyphenoxy)propylthio)-3-chlorophenyl]-2,4-thiazolidinedione

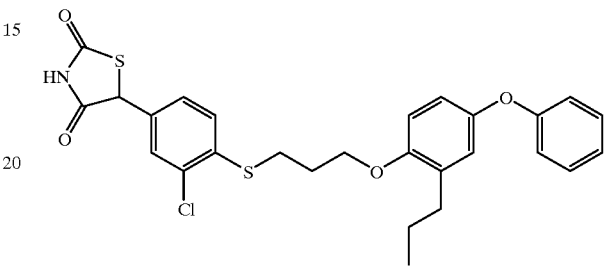

Step A: Preparation of methyl 3-chloro-4-(3-bromopropylthio)phenylacetate

To a solution of methyl 3-chloro-4-dimethylcarbamoylthiophenylacetate (8.5 g, 0.0295 mol) in methanol (30 mL) was added 25% NaOMe in methanol (7.0 mL, 0.034 mol). The reaction was heated to reflux for 2 h. TLC analysis shows residual starting carbamate. Additional NaOMe/MeOH (1.0 mL) was added and the mixture stirred an additional 30 min at reflux. After cooling to ambient temperature, the thiolate solution was added dropwise to a solution of 1,3-dibromopropane (12 mL, 0.12 mol) in methanol (30 mL). The resulting solution was refluxed for 3 h then cooled to ambient temperature, After standing overnight, the reaction was quenched by pouring into ice water. After adjusting to pH1 with conc. HCl, the aqueous solution was extracted with EtOAc (0.2 L then 2×0.1 L). The combined organics were washed with water, brine, dried over anhyd. MgSO$_4$, filtered, and concentrated. The residue was chromatographed over silica gel with 10% of ethyl acetate in hexane to afford the title compound.

$^1$H NMR (CDCl$_3$): δ 7.25–7.32 (m, 2H), 7.15 (dd, 1H, J=8.1, 1.8 Hz), 3.71 (s, 3H), 3.57 (s, 2H), 3.55 (t, 2H, J=7.7 Hz), 3.10 (t, 2H, J=7.7 Hz), 2.18 (m, 2H).

Step B: Preparation of methyl 4-(3-(2-propyl-4-phenoxyphenoxy)propylthio)3-chlorophenylacetate A solution of 4-(3-bromopropoxy)-3-propylphenyl phenyl ether (2.5 g, 7.18 mmol), methyl 3-chloro-4-hydroxyphenylacetate (1.42 g, 7.11 mmol) and cesium carbonate (2.43 g, 7.45 mmol) in DME (20 mL) was stirred at 40° C. overnight. The reaction mixture was partitioned between ethyl acetate and 0.2N HCl. The organic was washed twice with water, then dried over sodium sulfate. The organic was filtered and evaporated to an oil which was chromatographed over silica gel with 10% of ethyl acetate in hexane to afford the title compound.

$^1$H NMR (400 MHz, CDCl$_3$): δ 7.24–7.29 (m, 3H), 7.10 (dd, 1H, J=8.4, 2.1 Hz), 7.00 (t, 1H, J=7.3 Hz), 6.92–6.80 (m, 6H), 4.22 (t, 2H, J=6.1 Hz), 4.16 (t, 2H, J=6.0 Hz), 3.67 (s, 3H), 3.52 (s, 2H), 2.53 (t, 2H, J=7.4 Hz), 2.30 (quint, 2H, J=6.3 Hz), 1.55 (hex, 2H, 5.6 Hz), 0.89 (t, 3H, J=7.3 Hz).

Step C: Preparation of 5-[4-(3-(2-propyl-4-phenoxyphenoxy)propylthio)-3-chlorophenyl]-2,4-thiazolidinedione The title compound was prepared according to the method described in Example 1, Step C, methyl 4-(3-(2-propyl-4-phenoxyphenoxy)propylthio)-3-chlorophenylacetate as the starting material.

$^1$H NMR (400 MHz, CDCl$_3$): δ 8.60 (brs, 1H), 7.42 (d, 1H, J=2.3 Hz), 7.29–7.23 (m, 3H), 7.02–6.80 (m, 7H), 5.27 (s, 1H), 4.24 (t, 2H, J=6.1 Hz), 4.15 (t, 2H, J=6.0 Hz), 3.67 (s, 3H), 3.52 (s, 2H), 2.53 (t, 2H, J=7.4 Hz), 2.30 (quint, 2H, J=6.3 Hz), 1.55 (hex, 2H, 5.6 Hz), 0.89 (t, 3H, J=7.3 Hz).

EXAMPLE 15

5-[4-(3-(2-propyl-4-phenoxyphenoxy)propoxy)-3-chlorophenyl]-2,4-thiazolidinedione

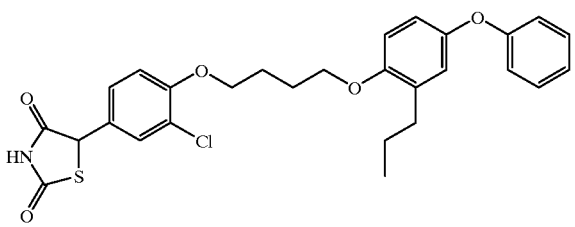

Step A: Preparation of 4-(4-bromobutoxy)-3-propylphenyl phenyl ether

A solution of 4-phenoxy-2-propylphenol (25.0 g, 0.11 mol), 1,4-dibromobutane (70.99 g, 0.33 mol) and cesium carbonate (39.28 g, 0.12 mol) in dry DMF (250 mL) was stirred at room temperature overnight. The reaction mixture was partitioned between ethyl acetate and 0.2N HCl. The organic layer was washed twice with water, then dried over sodium sulfate. The organic layer was filtered and evaporated to an oil which was chromatographed over silica gel with methylene chloride/hexane (1:1) to afford the title compound.

Step B: Preparation of methyl 4-(4-(2-propyl-4-phenoxyphenoxy)butoxy)-3-chlorophenylacetate A solution of 4-(4-bromobutoxy)-3-propylphenyl phenyl ether (5.7 g, 15.75 mmol), methyl 3-chloro-4-hyrdoxyphenylacetate (3.0 g, 15.00 mmol) and cesium carbonate (5.38 g, 16.50 mmol) in DMF (50 mL) was stirred at 40° C. overnight. The reaction mixturewas partitioned between ethyl acetate and 0.2N HCl. The organic layer was washed twice with water, then dried over sodium sulfate. The organic layer was filtered and evaporated to an oil which was chromatographed over silica gel with 10% of ethyl acetate in hexane to afford the title compound.

$^1$H NMR (400 MHz, CDCl$_3$): δ 7.28–7.24 (m, 3H), 7.10 (dd, 1H, J=8.4, 2.2 Hz), 7.02–6.98 (m, 1H), 6.92–6.76 (m, 6H), 4.09 (t, 2H, J=5.7 Hz), 4.01 (t, 2H, J=5.8 Hz), 3.67 (s, 3H), 3.52 (s, 2H), 2.53 (t, 2H, J=7.4 Hz), 2.02 (m, 4H), 1.55 (hex, 2H, 5.6 Hz), 0.89 (t, 3H, J=7.3 Hz).

Step C: Preparation of 5-[4-(3-(2-propyl-4-phenoxyphenoxy)butoxy)-3-chlorophenyl]-2,4-thiazolidinedione The title compound was prepared according to the method described in Example 1, Step C, using methyl 4-(4-(2-propyl-4-phenoxyphenoxy)butoxy)-3-chlorophenylacetate as the starting material.

$^1$H NMR (400 MHz, CDCl$_3$): δ 8.12 (brs, 1H), 7.42 (d, 1H, J=2.4 Hz), 7.28–7.23 (m, 3H), 7.02–6.75 (m, 7H), 5.28 (s, 1H), 4.09 (t, 2H, J=5.7 Hz), 4.03 (t, 2H, J=5.8 Hz), 3.67 (s, 3H), 3.52 (s, 2H), 2.53 (t, 2H, J=7.4 Hz), 2.02 (m, 4H), 1.55 (hex, 2H, 5.6 Hz), 0.89 (t, 3H, J=7.3 Hz).

EXAMPLE 16

5-[4-(4-(2-propyl-4-phenoxyphenoxy)butoxy)-3-chlorophenyl]-2,4-thiazolidinedione

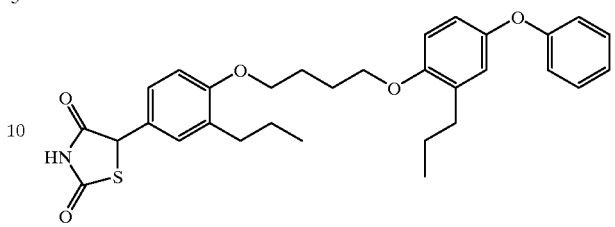

Step A: Preparation of methyl 4-(4-(2-propyl-4-phenoxyphenoxy)butoxy)-3-propylphenylacetate The title compound was prepared according to the method described in Example 15, Step A, using methyl 3-propyl-4-hydroxyphenylacetate as the starting material.

$^1$H NMR (400 MHz, CDCl$_3$): δ 7.31–7.25 (m, 2H), 7.04–6.76 (m, 9H), 4.02–4.00 (m, 4H), 3.67 (s, 3H), 3.55 (s, 2H), 2.61–2.53 (m, 4H), 2.03–1.98 (m, 4H), 1.68–1.55 (m, 4H), 0.98–0.90 (m, 6H).

Step B: Preparation of 5-[4-(4-(2-propyl-4-phenoxyphenoxy)butoxy)-3-propylphenyl]-2,4-thiazolidinedione The title compound was prepared according to the method described in Example 1, Step C, using methyl 4-(4-(2-propyl-4-phenoxyphenoxy)butoxy)-3-propylphenylacetate as the starting material.

$^1$H NMR (400 MHz, CDCl$_3$): δ 8.14 (brs, 1H), 7.29–7.24 (m, 2H), 7.19–6.12 (m, 2H), 7.02–6.90 (m, 1H), 6.84–6.75 (m, 6H), 5.30 (s, 1H), 4.02–4.00 (m, 4H), 3.67 (s, 3H), 3.55 (s, 2H), 2.61–2.53 (m, 4H), 2.03–1.98 (m, 4H), 1.68–1.55 (m, 4H), 0.98–0.90 (m, 6H).

EXAMPLE 17

5-[4-(4-(2-propyl-4-phenoxyphenoxy)butoxy)phenyl]-2,4-thiazolidinedione

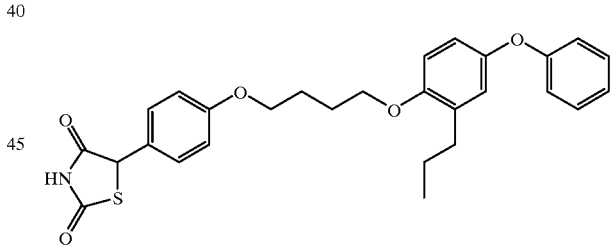

Step A: Preparation of methyl 4-(4-(2-propyl-4-phenoxyphenoxy)butoxy)phenylacetate The title compound was prepared according to the method described in Example 15, Step A, using methyl 4-hydroxyphenylacetate as the starting material.

$^1$H NMR (400 MHz, CDCl$_3$): δ 7.32–7.23 (m, 5H), 7.02–6.76 (m, 7H), 4.02–4.00 (m, 4H), 2.54 (t, 2H, J=6.4 Hz), 2.01–1.94 (m, 4H), 1.56 (hex, 2H, J=6.7 Hz), 0.90 (t, 3H, J=7.4 Hz).

Step B: Preparation of 5-[4-(4-(2-propyl-4-phenoxyphenoxy)butoxy)phenyl]-2,4-thiazolidinedione The title compound was prepared according to the method described in Example 1, Step C, using methyl 4-(4-(2-propyl-4-phenoxyphenoxy)butoxy)phenylacetate as the starting material.

$^1$H NMR (400 MHz, CDCl$_3$): δ 8.01 (brs, 1H), 7.32–7.23 (m, 5H), 7.02–6.76 (m, 7H), 5,32 (s, 1H), 4.02–4.00 (m, 4H), 2.54 (t, 2H, J=6.4 Hz), 2.01–1.94 (m, 4H), 1.56 (hex, 2H, J=6.7 Hz), 0.90 (t, 3H, J=7.4 Hz).

EXAMPLE 18

5-[3-(3-(2-propyl-4-phenoxyphenoxy)propoxy)phenyl]-2,4-thiazolidinedione

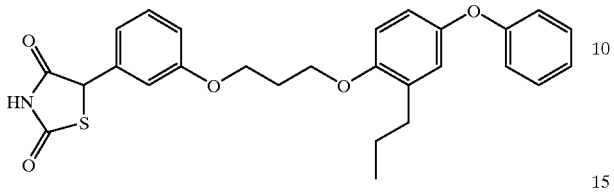

Step A: Preparation of methyl 3-(3-(2-propyl-4-phenoxyphenoxy)propoxy)phenylacetate The title compound was prepared according to the method described in Example 11, Step B, using methyl 3-hydroxyphenylacetate as the starting material.

$^1$H NMR (400 MHz, CDCl$_3$): δ 7.29–7.19 (m, 3H), 7.01–6.72 (m, 9H), 4.16 (t, 2H, J=6.2 Hz), 4.11 (t, 2H, J=6.1 Hz), 3.67 (s, 3H), 3.57 (s, 2H), 2.55 (t, 2H, J=6.2 Hz), 2.27 (quint, 2H, J=6.3 Hz), 1.56 (hex, 2H, J=7.2 Hz), 0.96 (t, 3H, J=7.3 Hz).

Step B: Preparation of 5-[3-(3-(2-propyl-4-phenoxyphenoxy)propoxy)phenyl]-2,4-thiazolidinedione The title compound was prepared according to the method described in Example 1, Step C, using methyl 3-(3-(2-propyl-4-phenoxyphenoxy)propoxy)phenylacetate as the starting material.

$^1$H NMR (400 MHz, CDCl$_3$): δ 8.48 (brs, 1H), 7.32–7.24 (m, 3H), 7.02–6.79 (m, 9H), 5.30 (s, 1H), 4.16 (t, 2H, J=6.2 Hz), 4.11 (t, 2H, J=6.1 Hz), 3.67 (s, 3H), 3.57 (s, 2H), 2.55 (t, 2H, J=6.2 Hz), 2.27 (quint, 2H, J=6.3 Hz), 1.56 (hex, 2H, J=7.2 Hz), 0.96 (t, 3H, J=7.3 Hz).

EXAMPLE 19

5-[3-(4-(2-propyl-4-phenoxyphenoxy)butoxy)phenyl]-2,4-thiazolidinedione

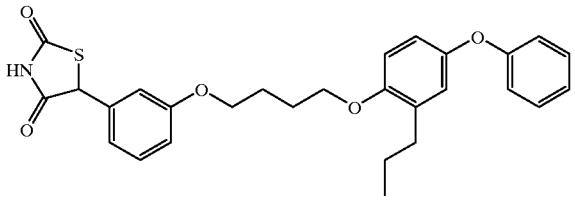

Step A: Preparation of methyl 3-(4-(2-propyl-4-phenoxyphenoxy)butoxy)phenylacetate The title compound was prepared according to the method described in Example 15, Step A, using methyl 3-hydroxyphenylacetate as the starting material.

$^1$H NMR (400 MHz, CDCl$_3$): δ 7.31–7.22 (m, 5H), 7.01–6.76 (m, 7H), 4.01–4.00 (m, 4H), 2.54 (t, 2H, J=6.4 Hz), 2.00–1.94 (m, 4H), 1.55 (hex, 2H, J=6.7 Hz), 0.91 (t, 3H, J=7.4 Hz).

Step B: Preparation of 5-[3-(4-(2-propyl-4-phenoxyphenoxy)butoxy)phenyl]-2,4-thiazolidinedione The title compound was prepared according to the method described in Example 1, Step C, using methyl 3-(4-(2-propyl-4-phenoxyphenoxy)butoxy)phenylacetate as the starting material.

$^1$H NMR(400 MHz, CDCl$_3$): δ 7.93 (brs, 1H), 7.31–7.22 (m, 5H), 7.00–6.75 (m, 7H), 5,31 (s, 1H), 4.02–4.00 (m, 4H), 2.53 (t, 2H, J=6.4 Hz), 2.01–1.93 (m, 4H), 1.55 (hex, 2H, J=6.7 Hz), 0.91 (t, 3H, J=7.4 Hz).

EXAMPLE 20

5-[3-(3-(2-propyl-4-phenoxyphenoxy)propoxy)phenyl]-2,4-oxazolidinedione

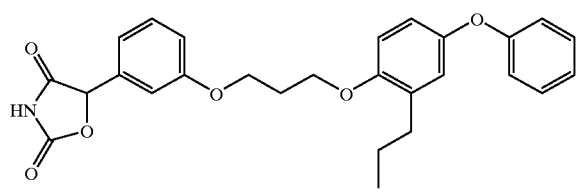

Step A: Preparation of Methyl 3-(3-(2-propyl-4-phenoxyphenoxy)propoxy)mandelate

A solution of methyl 3-hydroxymadelate (253 mg, 1.39 mmol), 4-(3-bromopropoxy)-3-propylphenyl phenyl ether (500 mg, 1.44 mmol) and cesium carbonate (475 mg, 1.46 mmol) in dry DMF (5 mL) was stirred at room temperature overnight. The reaction mixture was partitioned between ethyl acetate and 0.2N HCl. The organic layer was washed twice with water, then dried over sodium sulfate. The organic layer was filtered and evaporated to an oil which was chromatographed over silica gel with methylene chloride/hexane (1:1) to afford the title compound.

$^1$H NMR (400 MHz, CDCl$_3$): δ 7.29–7.24 (m, 3H), 7.03–6.79 (m, 9H), 5.12 (d, 1H, J=5.7 Hz), 4.18 (t, 2H, J=6.2 Hz), 4.13 (t, 2H, J=6.1 Hz), 3.40 (d, 1H, J=5.7 Hz), 2.55 (t, 2H, J=6.2 Hz), 2.27 (quint, 2H, J=6.3 Hz), 1.56 (hex, 2H, J=7.2 Hz), 0.96 (t, 3H, J=7.3 Hz).

Step B: Preparation of 5-[3-(3-(2-propyl-4-phenoxyphenoxy)propoxy)phenyl]-2,4-oxazolidinedione A solution of methyl 3-(3-(2-propyl-4-phenoxyphenoxy)propoxy)mandelate (194 mg), urea (39 mg) and sodium methoxide (0.90 mL, 0.5 M) was refluxed overnight. The reaction mixture was partitioned between ethyl acetate and water. The organic layer was washed twice with water, dried over sodium sulfate, filtered and evaporated to an oil, which was chromatographed over silica gel with 3% of methanol in methylenechloride to afford the title compound.

$^1$H NMR (400 MHz, CDCl$_3$): δ 7.34 (t, 1H, J=7.6 Hz), 7.30–7.24 (m, 2H), 7.03–6.79 (m, 9H), 5.74 (s, 1H), 4.18 (t, 2H, J=6.2 Hz), 4.13 (t, 2H, J=6.1 Hz), 2.55 (t, 2H, J=6.2 Hz), 2.27 (quint, 2H, J=6.3 Hz), 1.56 (hex, 2H, J=7.2 Hz), 0.96 (t, 3H, J=7.3 Hz).

EXAMPLE 21

5-[4-(3-(2-propyl-4-phenoxyphenoxy)propoxy) phenyl]-2,4-oxazolidinedione

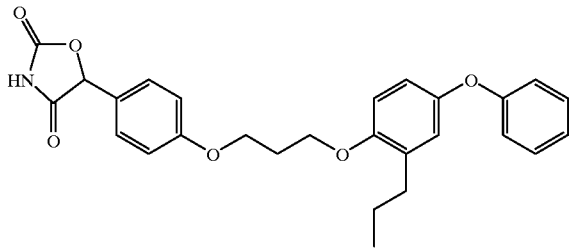

Step A: Preparation of Ethyl 4-(3-(2-propyl-4-phenoxyphenoxy)propoxy)mandelate

The title compound was prepared according to the method described in Example 20, Step A, using ethyl 4-hydroxymandelate as the starting material.

$^1$H NMR (400 MHz, CDCl$_3$): δ 7.32–7.24 (m, 5H), 7.01 (t, 1H, J=7.4 Hz), 6.92–6.79 (m, 6H), 5.03 (d, 1H, J=5.7 Hz), 4.26 (quart, 2H, J=7.4 Hz), 4.18 (t, 2H, J=6.2 Hz), 4.13 (t, 2H, J=6.1 Hz), 3.36 (d, 1H, J=5.7 Hz), 2.55 (t, 2H, J=6.2 Hz), 2.27 (quint, 2H, J=6.3 Hz), 1.56 (hex, 2H, J=7.2 Hz), 1.21 (t, 3H, J=7.2 Hz), 0.96 (t, 3H, J=7.3 Hz).

Step B: Preparation of 5-[4-(3-(2-propyl-4-phenoxyphenoxy)propoxy)phenyl]-2,4-oxazolidinedione The title compound was prepared according to the method described in Example 20, Step B, using ethyl 4-(3-(2-propyl-4-phenoxyphenoxy)propoxy)mandelate as the starting material.

$^1$H NMR (400 MHz, CDCl$_3$): δ 7.32–7.24 (m, 5H), 7.01 (t, 1H, J=7.4 Hz), 6.92–6.79 (m, 6H), 5.74 (s, 1H), 4.18 (t, 2H, J=6.2 Hz), 4.13 (t, 2H, J=6.1 Hz), 2.55 (t, 2H, J=6.2 Hz), 2.27 (quint, 2H, J=6.3 Hz), 1.56 (hex, 2H, J=7.2 Hz), 0.96 (t, 3H, J=7.3 Hz).

EXAMPLE 22

5-[4-(3-(2-propyl-4-(4'-methylsulfonyl)phenoxyphenoxypropoxy)phenyl]-2,4-thiazolidinedione

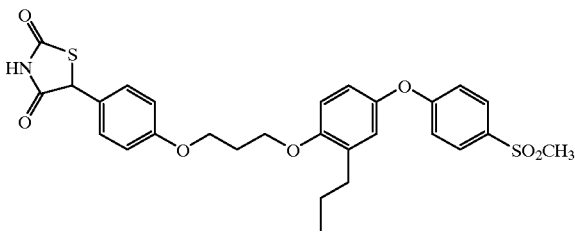

Step A: Preparation of 2-Propyl-4-(4'-methylsulfonyl) phenoxyphenol

A solution of hydroquinone (33.00 g, 0.30 mol) and potassium carbonate (45.6 g, 0.33 mol) in dry DMF (250 mL) was stirred at 40° C. for 30 minutes. Allyl bromide (5.20 mL, 0.06 mol) was added and the reaction was stirred overnight. The reaction mixture was partitioned between ethyl acetate and 0.2N HCl. The organic layer was washed twice with water, then dried over sodium sulfate. The organic layer was filtered and evaporated to an oil which was chromatographed over silica gel with hexane/ethyl acetate (4:1) to afford 4-allyloxyphenol.

$^1$H NMR (400 MHz, CDCl$_3$): δ 6.74 (dd, 4H, J=9.0 Hz, 12.5 Hz), 6.03 (m, 1H), 5.37 (dd, 1H, J=1.3 Hz, 15.7 Hz), 5.25 (dd, 1H, J=1.3 Hz, 9.0 Hz), 4.64 (broad s, 1H), 4.46 (d, 2H, J=5.3 Hz)

A solution of 4-allyloxyphenol (4.3 g, 28.70 mmol), 4-fluorophenyl methyl sulfone (5.00 g, 28.70 mmol) and potassium carbonate (4.8 g, 34.45 mmol) in dry N,N-dimethylacetamide (50 mL) was heated at reflux overnight. The reaction mixture was partitioned between ethyl acetate and 0.2N HCl. The organic layer was washed twice with water, then dried over sodium sulfate. The organic layer was filtered and evaporated to an oil which was chromatographed over silica gel with hexane /ethyl acetate (5:1) to afford 4-(4'-methylsulfonyl)phenoxyphenyl allyl ether.

$^1$H NMR (400 MHz, CDCl$_3$): δ 7.84 (d, 2H, J=8.9 Hz), 7.00 (m, 6H), 6.08 (m, 1H), 5.44 (dd, 1H, J=1.5 Hz, 15.5 Hz), 5.31 (dd, 1H, J=1.4 Hz, 8.8 Hz), 4.45 (d, 2H, J=5.6 Hz), 3.02 (s, 3H).

A solution of 4-((4'-methylsulfonyl)phenoxy)phenyl allyl ether (5.20 g, 0.12 mol), in dry 1,2-dichlorobenzene was heated at 180° C. overnight. After solvent removal in vacuo, the residue was chromatographed over silica gel with hexane/ethyl acetate (4:1) to afford 2-allyl-4-(4'-methylsulfonyl)phenoxyphenol.

$^1$H NMR (400 MHz, CDCl$_3$): δ 7.84 (d, 2H, J=8.9 Hz), 7.34 (s, 1H), 7.01 (dd, 2H, J=9.8 Hz, 2.0 Hz), 6.84 (d, 2H, J=2.2 Hz), 5.97 (m,1H), 5.18 (d, 1H, J=1.4 Hz), 5.15 (dd, 1H, J=1.5 Hz, 5.8 Hz), 4.93 (s, 1H), 3.38 (d, 2H, J=6.5 Hz), 3.02 (s, 3H).

A solution of 2-allyl-4-(4'-methylsulfonyl)phenoxyphenol (3.8 g, 12.40 mmol) and 5% palladium on carbon (1.2 g) in ethyl acetate (50 mL) was stirred at room temperature under hydrogen atmosphere for 3 hr. The reaction was filtered through Celite, passed through a short pad of silica gel and concentrated in vacuo to an oil to afford 2-propyl-4-(4'-methylsulfonyl)phenoxyphenol which was used without further purification.

$^1$H NMR (400 MHz, CDCl$_3$): δ 7.86 (d, 2H, J=8.9 Hz), 7.02 (d, 2H, J=9.9 Hz), 6.84 (s,1H), 6.78 (d, 2H, J=1.0 Hz), 4.73 (s, 1H), 3.02 (s, 3H), 2.56 (t, 2H, J=7.5 Hz), 1.62 (quint, 2H, J=7.5 Hz), 0.95 (t, 3H, J=7.5 Hz)

Step B: Preparation of Ethyl 4-(3-bromopropoxy)mandelate

A solution of ethyl 4-hydroxymandelate (19.6 g, 0.1 mol), 1,3-dibromopropane (60.75 g, 0.3 mol) and cesium carbonate (35.75 g, 0.11 mol) in dry DMF (200 mL) was stirred at room temperature overnight. The reaction mixture was partitioned between ethyl acetate and 1.0 N HCl. The organic layer was washed twice with water, once with brine and then dried over sodium sulfate. The organic layer was then filtered and the solvent remove in vacuo. The resulting oil was chromatographed on silica gel, using a gradient of 100% hexane to methylene chloride/hexane (2:1) to yield the titled compound.

$^1$H NMR (400 MHz, CDCl$_3$): δ 7.30 (m, 2H); 6.86 (m, 2H); 5.82 (d, 1H, J=5.6 Hz); 4.2 (m, 2H); 4.08 (t, 3H, J=5.6 Hz); 3.58 (t, 2H, J=0.016 ppm); 3.37 (d, 1H, J=5.6 Hz); 2.29 (m, 2H); 1.21 (t, 3H, J=7.2 Hz).

Step C: Preparation of Ethyl 4-(3-(2-propyl-4-(4'-methylsulfonyl)phenoxyphenoxypropoxy)mandelate A solution of 2-propyl-4-(4'-methylsulfonyl) phenoxyphenol (19.0 g, 62.0 mmol) (as prepared in Step A), potassium carbonate (9.4 g, 68.2 mmol) and DMF (100 mL) were stirred at 40° C. for 0.5 hours. Then ethyl 4-(3-bromopropoxy)mandelate (19.5 g, 58.9 mmol) was added and the reaction mixture was stirred overnight. The reaction mixture was partitioned between ethyl acetate and 1.0 N HCl. The organic layer was washed twice with water, once with brine and then dried over sodium sulfate. The organic layer was then filtered and the solvent remove in vacuo. The resulting oil was chromatographed on silica gel, using ethyl acetatelhexane/methylene chloride (1:4:5) to yield the titled compound.

¹H NMR (400 MHz, CDCl₃): δ 7.30 (m, 2H); 6.86 (m, 2H); 5.82 (d, 1H, J=5.6 Hz); 4.2 (m, 2H); 4.08 (t, 3H, J=5.6 Hz ppm); 3.58 (t, 2H, J=6.4 Hz); 3.37 (d, 1H, J=5.6 Hz); 2.29 (m, 2H); 1.21 (t, 3H, J=7.2 Hz).

Step D: Preparation of ethyl α-chloro-4-(3-(2-propyl-4-(4'-methylsulfonylphenoxy)phenoxy)propoxy)phenylacetate To a solution of ethyl 4-(3-(2-propyl-4-(4'-methylsulfonyl)phenoxy-phenoxypropoxy) mandalate of Step C (16.8 g, 30.18 mmol), pyridine (2.95 mL, 36.51 mmol) and toluene (160 mL) was added thionyl chloride (2.88 mL, 39.54 mmol). The reaction mixture was stirred overnight and then partitioned between ethyl acetate and water. The organic layer was washed twice with water, once with brine, dried over sodium sulfate, and filtered. The solvent was removed in vacuo and the resulting oil was filtered through a pad of silica gel, using acetone/hexane (1:4) to yield the titled compound.

¹H NMR (400 MHz, CDCl₃): δ 7.86 (m, 2H); 7.35 (m, 2H); 7.03 (m, 2H); 6.92 (m, 2H); 6.87 (bs, 3H); 5.12 (bs, 1H); 4.2 (m, 6H); 3.05 (s, 3H); 2.59 (t, 2H, J=7.6 Hz); 2.31 (m, 2H); 1.60 (m, 3H); 1.25 (m, 3H); 0.93 (t, 3H, J=7.2 Hz).

Step E: Preparation of 5-[4-(3-(2-propyl-4-(4'-methylsulfonyl)phenoxy)phenoxy)propoxy)phenyl]-2,4-thiazolidinedione The title compound was prepared according to the method described in Example 1, Step C (second paragraph), using ethyl α-chloro-4-(3-(2-propyl-4-(4'-methylsulfonylphenoxy)phenoxy)propoxy)phenylacetate as the starting material.

¹H NMR (400 MHz, CDCl₃): δ 8.18 (broad s, 1H), 7.84 (d, 2H, J=8.9 Hz), 7.35 (d, 2H, J=8.7 Hz), 6.99 (d, 2H, J=8.7 Hz), 6.92 (d, 2H, J=9.8 Hz), 6.84 (s, 3H), 5.35 (s, 1H), 4.12 (t, 2H, J=6.6 Hz), 4.08 (t, 2H, J=6.3 Hz), 3.02 (s, 3H), 2.57 (t, 2H, 7.5 Hz), 2.28 (q, 2H, J=6.4 Hz), 1.57(hex, 2H, 5.8 Hz), 0.91 (t, 3H, J=7.5 Hz).

EXAMPLE 23

5-[4-(3-(2-propyl-4-(4'-methylphenoxy)phenoxypropoxy)phenyl]-2,4-thiazolidinedione

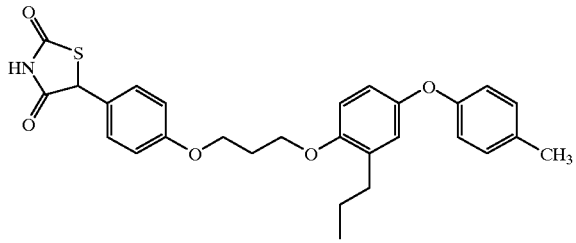

Step A: Preparation of 2-Propyl-4-(4'-methylphenoxy)phenol

A solution of 4-methylphenol (4.52 g, 40.29 mmol), 4-fluorobenzaldehyde (5.00 g, 40.29 mmol) and potassium carbonate (6.70 g, 48.35 mmol) in dimethylacetamide (40 mL) was refluxed for 12 h and cooled to room temperature. Water was added and the reaction mixture was extracted with ethyl acetate. The organic extract was washed with brine, dried over sodium sulfate, filtered and concentrated to afford an oil which was chromatographed on silica gel (15% ethyl acetate/hexane) to afford 4-(4'-methylphenoxy)benzaldehyde.

A solution of 4-(4'-methylphenoxy)benzaldehyde (9.00 g, 41.63 mmol) in CHCl₃ (75 mL) was treated with m-chloroperbenzoic acid (46–85%, 15.80 g, 52.00 mmol) and stirred for 3 h at room temperature. The reaction was washed with sat. aq. NaHSO₃, sat. aq. NaHCO₃, and water. The organic layer is concentrated and the residual oil taken up in MeOH (10 mL) containing a few drops of conc. HCL and stirred for 1 h at room temperature. The solvent is removed in vacuo and the resulting oil was chromatographed on silica gel (20% ethyl acetate/hexane) to afford 4-(4'-methylphenoxy)phenol.

A solution of 4-(4'-methylphenoxy)phenol (4.75 g, 23.30 mmol), potassium carbonate (4.17 g, 30.30 mmol) and allyl bromide (2.22 mL, 25.60 mmol) in DMF (50 mL) was stirred for 5 h at 60° C. After cooling, the reaction mixture was neutralized with 1 N HCl and extracted with ethyl acetate. The organic extract was washed with brine, dried over sodium sulfate, filtered and concentrated to afford an oil which was chromatographed on silica gel (15% ethyl acetate/hexane) to afford 4-(4'-methylphenoxy)phenyl allyl ether.

4-(4'-Methylphenoxy)phenyl allyl ether (4.00 g, 16.37 mnmol) was taken up in 1,2-dichlorobenzene (50 mL) and refluxed for 20 h. After cooling, the solvent was removed in vacuo and the resulting crude oil was chromatographed on silica gel (15% ethyl acetate/hexane) to afford 4-(4'-methylphenoxy)-2-allylphenol.

A solution of 4-(4'-methylphenoxy)-2-allylphenol (2.30 g, 9.42 mmol) and 5% Pd/C (0.90 g) in ethyl acetate (30 mL) was stirred under H₂ atmosphere for 3 h at room temperature. The reaction mixture was filtered through a short pad of silica gel and concentrated in vacuo to afford the title compound which was used as is. ¹H NMR (400 MHz, CDCl₃): δ 7.19 (d, 2H), 6.86 (d, 1H), 6.83 (dd, 2H), 6.72 (d, 2H), 4.61 (s, 1H), 2.53 (t, 2H), 2.30 (s, 3H), 1.61 (hex, 2H), 0.96 (t, 3H).

Step B: Preparation of Methyl 4-(3-(2-propyl-4-(4'-methylphenoxy)phenoxy)propoxy)phenylacetate The title compound was prepared according to the method described in Example 1, Step B using 2-propyl-4-(4'-methylphenoxy)phenol (19.0 g, 62.0 mmol) and methyl 4-(3-bromopropoxy)phenylacetate (19.5 g, 58.9 mmol) (Example 1, step A) as the starting materials. ¹H NMR (400 MHz, CDCl₃): δ 7.18 (d, 2H), 7.07 (d, 2H), 6.85 (m, 5H), 6.76 (d, 1H), 6.70 (d, 1H), 5.33 (s, 1H), 4.15 (t, 2H), 4.10 (t, 2H), 3.67 (s, 3H), 3.55 (s, 2H), 2.53 (t, 2H), 2.28 (s, 3H), 2.25 (quint, 2H), 1.59 (hex, 2H), 0.89 (t, 3H).

Step C: Preparation of 5-[4-(3-(2-propyl-4-(4'-methylphenoxy)phenoxy)propoxy)phenyl]-2,4-thiazolidinedione The title compound was prepared according to the method described in Example 1, Step C, using methyl 4-(3-(2-propyl-4-(4'-methylphenoxy)phenoxy)propoxy)phenylacetate (19.5 g, 58.9 mmol) as the starting material.

¹H NMR (400 MHz, CDCl₃): δ 8.32 (broad s, 1H), 7.32 (d, 2H); 7.09 (d, 2H); 6.94 (d, 2H); 6.85 (d, 2H); 6.83 (d, 1H), 6.77 (dd, 2H), 5.33 (s, 1H); 4.05 (t, 2H); 4.00 (t, 2H); 2.55 (t, 2H); 2.31 (s, 3H); 2.00 (quint, 2H); 1.59 (hex, 2H); 0.93 (t, 3H).

EXAMPLE 24

5-[4-(3-(2-propyl-4-(4'-chlorophenoxy)phenoxy)propoxy)phenyl]-2,4-thiazolidinedione

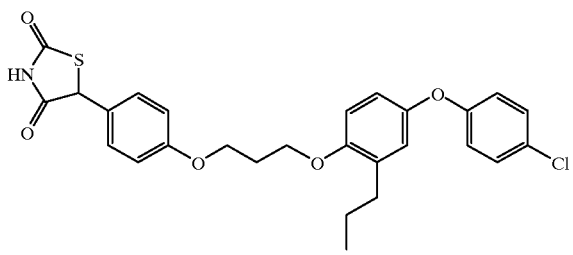

The title compound was prepared according to the method described in Example 23, using 4-chlorophenol in place of 4-methylphenol as the starting material in Step A. $^1$H NMR (400 MHz, CDCl$_3$): δ 8.19 (broad s, 1H), 7.33 (d, 2H), 7.22 (d, 2H), 6.93 (d, 2H), 6.85 (d, 1H), 6.84 (d, 2H), 6.80 (dd, 2H), 5.32 (s, 1H), 4.18 (t, 2H), 4.11 (t, 2H), 2.54 (t, 2H, 2.37 (quint, 2H), 1.55 (hex, 2H), 0.89 (t, 3H).

EXAMPLE 25

5-[4-(3-(2-propyl-4-(4'-phenyl)phenoxy)phenoxy)propoxy)phenyl]-2,4-thiazolidinedione

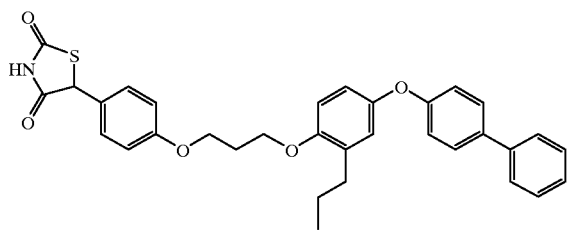

The title compound was prepared according to the method described in Example 23, using 4-phenylphenol in place of 4-methylphenol as the starting material in Step A. $^1$H NMR (400 MHz, CDCl$_3$): δ 8.01 (broad s, 1H), 7.54 (d, 2H), 7.50 (d, 2H), 7.40 (t, 2H), 7.32 (d, 2H), 7.31 (t, 1H), 6.98 (d, 2H), 6.91 (d, 2H), 6.98 (d, 1H), 6.85 (dd, 1H), 6.87 (d, 1H), 5.28 (s, 1H), 4.05 (t, 2H); 4.00 (t, 2H), 2.56 (t, 2H), 1.99 (quint, 2H), 1.59 (hex, 2H), 0.92 (t, 3H).

EXAMPLE 26

5-[3-(3-(2-propyl-4-(4'-methoxyphenoxy)propoxy)phenyl]-2,4-thiazolidinedione

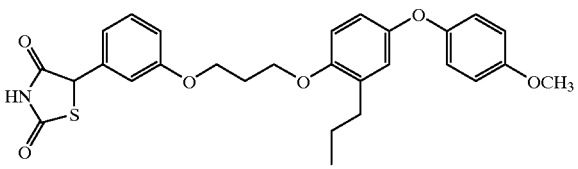

The title compound was prepared according to the method described in Example 23, using 4-methoxyphenol in place of 4-methylphenol as the starting material in Step A and methyl 3-(3-bromopropoxy)-phenylacetate in place of methyl 4-(3-bromopropoxy)-phenylacetate in Step B. $^1$H NMR (400 MHz, CDCl$_3$): δ 8.09 (broad s, 1H), 7.31 (t, 1H), 7.23 (m, 1H), 7.25 (dd, 1H), 6.95 (d, 1H), 6.89 (d, 2H), 6.83 (d, 2H), 6.78 (d, 1H), 6.75 (d, 1H), 6.72 (dd, 1H), 5.31 (s, 1H), 4.17 (t, 2H), 4.10 (t, 2H), 3.77 (s, 3H), 2.52 (t, 2H), 2.26 (quint, 2H), 1.54 (hex, 2H), 0.88 (t, 3H).

EXAMPLE 27

5-[3-(3-(2-propyl-4-(4'-fluorophenoxy)phenoxy)propoxy)phenyl]-2,4-thiazolidinedione

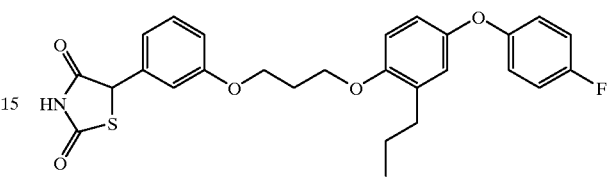

The title compound was prepared according to the method described in Example 26, using 4-fluorophenol in place of 4-methoxyphenol as the starting material. $^1$H NMR (400 MHz, CDCl$_3$): δ 8.01 (broad s, 1H), 7.54 (d, 2H), 7.49 (d, 2H), 7.40 (t, 1H), 7.31 (d, 1H), 7.29 (d, 1H), 6.95 (overlapping d's, 2H), 6.87 (d, 1H), 6.85 (dd, 1H), 5.32 (s, 1H), 4.21 (t, 2H); 4,15 (t, 2H), 2.56 (t, 2H), 2.29 (quint, 2H), 1.57 (hex, 2H), 0.90 (t, 3H).

EXAMPLE 28

5-[4-(4-(2-propyl-4-phenoxyphenoxy)butyl)phenyl]-2,4-thiazolidinedione

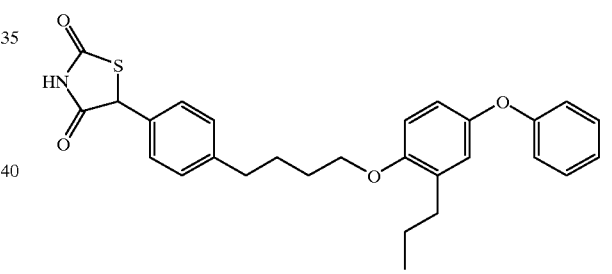

Step A: Preparation of methyl 4-bromophenylacetate

A solution of 4-bromophenylacetic acid (10.0 g, 46.5 mmol), in methanol (125 mL) and sulfuric acid (5 mL) was heated at reflux overnight. The reaction mixture was concentrated and partitioned between ethyl ether and saturated aqueous sodium bicarbonate. The organic layer was washed with water and brine, then dried over magnesium sulfate. The organic layer was filtered and evaporated to an oil to afford the title compound.

$^1$H NMR (400 MHz, CDCl$_3$): δ 7.42 (d, 2H, J=8.3 Hz) 7.13 (d, 2H, J=8.3 Hz), 3.67 (s, 3H), 3.56 (s, 2H).

Step B: Preparation of methyl (4-(4-hydroxyl-1-butynyl)phenylacetate

A solution of the product from step A (1.45 g, 6.35 mmol), 1-hydroxy-3-butyne (0.89 g, 12.7 mmol), tetrakis(triphenylphosphine)palladium(O) (0.293 g, 4 mol %), copper(I) bromide (0.109 g, 12 mol % ) in triethylamine (12.5 mL) was purged with nitrogen and heated at reflux for 1 h. The reaction mixture was concentrated and partitioned between ethyl ether and saturated aqueous ammonium chloride. The organic layer was washed with water and brine, then dried over magnesium sulfate. The organic layer was filtered and evaporated to an oil which was chromatographed over silica gel with chloroform/ethyl acetate (10:1) affording the title compound.

$^1$H NMR (400 MHz, CDCl$_3$): δ 7.34 (d, 2H, J=8.3 Hz), 7.12 (d,2H, J=8.3 Hz), 3.79 (t, 2H, J=6.2 Hz), 3.67 (s, 2H), 3.59 (s, 3H), 2.67 (t, 2H, J=6.2 Hz).

Step C: Preparation of methyl (4-(4-hydroxybutyl) phenylacetate

A solution of the product from step B (1.38 g, 6.35 mmol) in ethanol (25 mL) was degassed and purged with nitrogen, palladium over carbon (10%) was added, the reaction mixture was degassed and purged with hydrogen. The mixture was stirred under hydrogen at room temperature for 2 h and filtered through celite. The filtrate was evaporated to afford the title compound.

$^1$H NMR (400 MHz, CDCl$_3$): δ 7.13–7.18 (m, 4H), 3.62–3.66 (m,5H), 3.57 (s, 2H), 2.60 (t, 2H, J=7.2 Hz), 1.59–1.68 (m, 4H), 1.40 (brs, 1H).

Step D: Preparation of methyl (4-(4-(2-propyl-4-phenoxyphenoxy)butyl)phenylacetate A solution of the product from step C (0.395 g, 1.80 mmol), methanesulfonic anhydride (0.470 g, 2.70 mmol), 4-(dimethylamino)pyridine (0.001 g, catalytic amount) and pyridine (0.267 mL, 2.70 mmol) in methylene chloride (2 mL) was stirred at room temperature 1 h. The reaction mixture was concentrated, diluted with ethyl acetate, and washed twice with water and brine. The organic layer was dried over sodium sulfate, filtered and evaporated to an oil.

The residual oil was added to a reaction mixture containing 4-phenoxy-2-propylphenol (0.483 g, 2.12 mmol), and cesium carbonate (0.749 g, 2.30 mmol) in DMF (2 mL). The resulting mixture was stirred at 60° C. overnight. The reaction mixture was partitioned between ethyl acetate and 0.45M citric acid. The organic layer was washed once with water, brine, then dried over sodium sulfate. The organic layer was filtered and evaporated to an oil which was chromatographed over silica gel with toluene/hexane (1:1) to afford the title compound.

$^1$H NMR (400 MHz, CDCl$_3$): δ 7.27–7.18 (m, 7H), 6.92–6.75 (m, 5H), 3.93 (brs, 2H), 3.67 (s, 3H), 3.58 (s, 2H), 2.67 (brs, 2H), 2.54 (t, 2H, J=7.3 Hz), 1.81 (brs, 4H), 1.56 (m, 2H), 0.90 (t, 3H, J=7.3 Hz)

Step E: Preparation of 5-[4-(4-(2-propyl-4-phenoxyphenoxy)butyl)phenyl]-2,4-thiazolidinedione The title compound was prepared according to the method described in Example 1, Step C, using methyl (4-(4-(2-propyl-4-phenoxyphenoxy)butyl)phenylacetate as the starting material.

$^1$H NMR (400 MHz, CDCl$_3$): δ 8.24 (brs, 1H), 7.34–7.22 (m, 6H), 6.92–6.75 (m, 6H), 5.34 (s, 1H), 3.93 (brs, 2H), 2.69 (brs, 2H), 2.52 (t, 2H, J=7.4 Hz), 1.82 (brs, 4H), 1.57 (quint, 2H, 7.5 Hz), 0.90 (t, 3H, J=7.3 Hz).

EXAMPLE 29

5-[4-(4-(2-propyl-4-(4'-methoxyphenoxy)phenoxy) butyl)phenyl]-2,4-thiazolidinedione

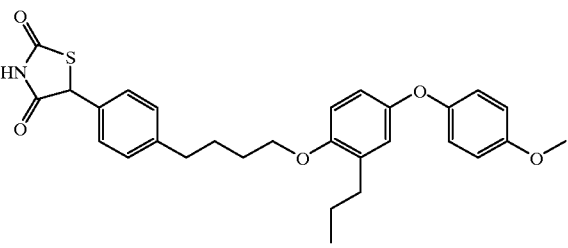

The title compound was prepared according to the method described in Example 28, using 2-propyl-4-(4'-methoxyphenoxy)phenol in place of 2-propyl-4-phenoxyphenol as the starting materials in step D.

$^1$H NMR (400 MHz, CDCl$_3$): δ 7.98 (brs, 1H), 7.34 (m, 2H), 7.24 (m, 3H), 6.71–6.90 (m, 6H), 5.34 (s, 1H), 3.91 (brs, 2H), 3.77 (s, 3H), 2.69 (brs, 2H), 2.52 (t, 2H, J=7.3 Hz), 1.81 (brs, 4H), 1.57 (m, 2H), 0.89 (t, 3H, J=7.3 Hz).

CI-MS m/e=528.3 (M+Na).

EXAMPLE 30

5-[4-(4-(2-propyl-4-(4'-chlorophenoxy)phenoxy) butyl)phenyl]-2,4-thiazolidinedione

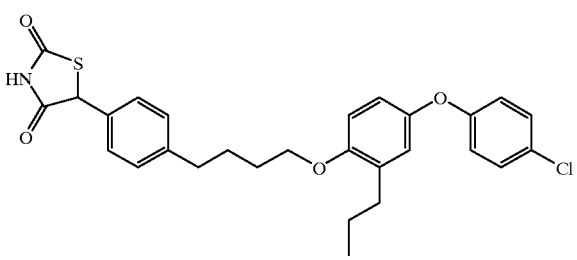

The title compound was prepared according to the method described in Example 28, using 2-propyl-4-(4'-chlorophenoxy)phenol in place of 2-propyl-4-phenoxyphenol as the starting materials in step D.

$^1$H NMR (400 MHz, CDCl$_3$): δ 7.98 (brs, 1H), 7.32 (m, 2H), 7.19 (m, 3H), 6.75–6.84 (m, 6H), 5.35 (s, 1H), 3.93 (brs, 2H), 2.69 (brs, 2H), 2.54 (t, 2H, J=7.6 Hz), 1.81 (brs, 4H), 1.55 (m, 2H), 0.90 (t, 3H, J=7.3 Hz).

CI-MS m/e=532.2 (M+Na).

EXAMPLE 31

5-[3-(4-(2-propyl-4-(4'-chlorophenoxy)phenoxy)butyl)phenyl]-2,4-thiazolidinedione

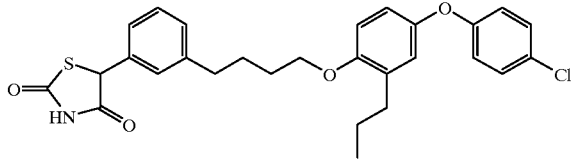

The title compound was prepared according to the method described in Example 28, using methyl (3-bromo)phenylacetate in place of methyl (4-bromo)phenylacetate as the starting material in step B and 2-propyl-4-(4'-chlorophenoxy)phenol in place of 2-propyl-4-phenoxyphenol as the starting materials in step D.

$^1$H NMR (400 MHz, CDCl$_3$): δ 8.20 (brs, 1H), 7.32–7.20 (m, 5H), 6.85–6.75 (m, 6H), 5.33 (s, 1H), 3.93 (brs, 2H), 2.70 (brs, 2H), 2.54 (t, 2H, J=7.6 Hz), 1.81 (brs, 4H), 1.55 (m, 2H), 0.90 (t, 3H, J=7.3 Hz).

CI-MS m/e=532.2 (M+Na).

EXAMPLE 32

5-[3-(5-(2-propyl-4-phenoxy-phenoxy)pentyl)phenyl]-2,4-thiazolidinedione

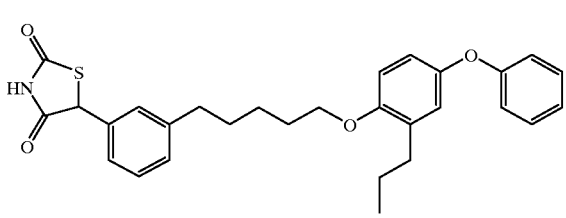

The title compound was prepared according to the method described in Example 28, using methyl 3-bromophenylacetate in place of methyl 4-bromophenylacetate and 4-pentyn-1-ol in place of 3-butyn-1-ol as the starting materials in step B.

$^1$H NMR (400 MHz, CDCl$_3$): δ 8.11 (brs, 1H), 7.32–7.22 (m, 6H), 7.21–6.7 (m, 6H), 5.33 (s, 1H), 3.91 (t, 2H, 6.3 Hz), 2.65 (t, 2H, 7.6 Hz), 2.52 (t, 2H), 1.83–1.50 (m, 8H), 0.89 (t, 3H, 7.3 Hz).

CI-MS: m/e=490.3 (M+1).

EXAMPLE 33

5-[3-(5-(2-propyl-4-(4'-methoxyphenoxy)phenoxy)pentyl)phenyl]-2,4-thiazolidinedione

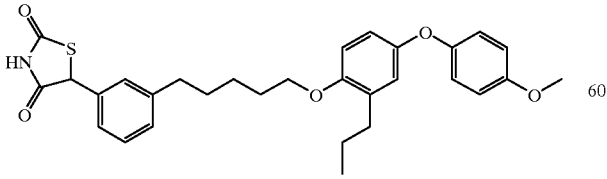

The title compound was prepared according to the method described in Example 28, using methyl 3-bromophenylacetate in place of methyl 4-bromophenylacetate and 4-pentyn-1-ol in place of 3-butyn-1-ol as the starting materials in step B, and 2-propyl-4-(4'-methoxyphenoxy)phenol in place of 2-propyl-4-phenoxyphenol as. the starting materials in step D.

$^1$H NMR (400 MHz, CDCl$_3$): δ 8.19 (brs, 1H), 7.34 (m, 1H), 7.21 (m, 3H) 6.9–6.71 (m, 7H), 5.3 (s, 1H), 3.91 (t, 2H, J=6.3 Hz), 3.76 (s, 3H), 2.64 (t, 2H, J=7.6 Hz), 2.51 (t, 2H, J=7.6 Hz), 1.81–1.59 (m, 8H), 0.89 (t, 3H, J=7.3 Hz).

CI-MS: m/e=519.3 (M+).

EXAMPLE 34

5-[3-(5-(2-propyl-4-(4'-fluorophenoxy)phenoxy)pentyl)phenyl]-2,4-thiazolidinedione

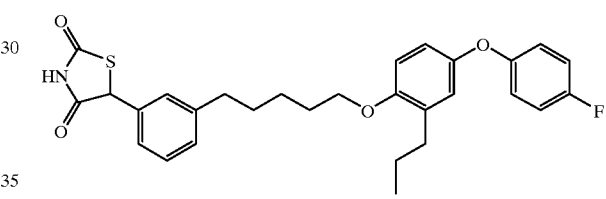

The title compound was prepared according to the method described in Example 28, using methyl 3-bromophenylacetate in place of methyl 4-bromophenylacetate and 4-pentyn-1-ol in place of 3-butyn-1-ol as the starting materials in step B, and 2-propyl-4-(4'-fluorophenoxy)phenol in place of 2-propyl-4-phenoxyphenol as the starting materials in step D.

$^1$H NMR (400 MHz, CDCl$_3$): δ 8.33 (brs, 1H), 7.34 (m, 1H), 7.21 (m, 3H) 6.9–6.71 (m, 7H), 5.3 (s, 1H), 3.90 (t, 2H, 6.3 Hz), 2.64 (t, 2H, 7.6 Hz), 2.51 (t, 2H, 7.6 Hz), 1.82–1.59 (m, 8H), 0.89 (t, 3H, 7.3 Hz).

CI-MS: m/e=507.2 (M+).

EXAMPLE 35

5-[3-(5-(2-propyl-4-(4'-phenylphenoxy)phenyl)pentoxy)phenyl]-2,4-thiazolidinedione

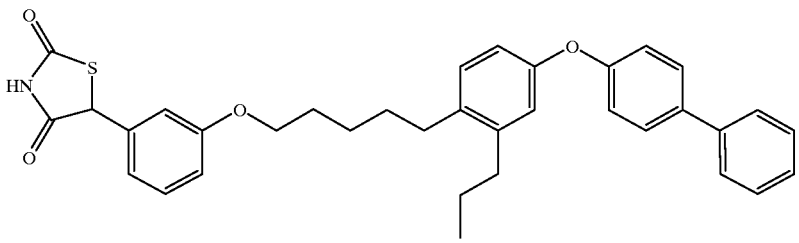

Step A: Preparation 5-(2-propyl-4-(4'-phenylphenoxy)phenyl)pentyn-1-ol

A solution of 4-(4'-phenylphenoxy)-2-propylphenol (1.0 g, 3.30 mmol), trifluoromethanesulfonic anhydride (0.832 mL, 4.95 mmol) and pyridine (0.400 mL, 4.95 mmol) in methylene chloride (3 mL) was stirred (0° C.-RT) overnight. The reaction mixture was concentrated, diluted with ethyl acetate, and washed twice with water and once with brine. The organic layer was dried over sodium sulfate, filtered and evaporated to an oil.

A solution of the residual oil (1.30 g, 3.03 mmol), 4-pentyn-1-ol (0.567 mL, 6.1 mmol), tetrakis (triphenylphosphine)palladium(O) (0.175 g, 0.151 mmol), in pyridine (3.0 mL) was purged with nitrogen and heated at 80° C. overnight. The reaction mixture was concentrated and partitioned between ethyl acetate and saturated aqueous ammonium chloride. The organic layer was washed with water and brine, then dried over sodium sulfate. The organic layer was filtered and evaporated to an oil which was chromatographed over silica gel with toluene/ethylacetate (10:1) to afford the title compound.

$^1$H NMR (400 MHz, CDCl$_3$): δ 7.55 (m, 5H), 7.41 (t, 2H, J=7.3 Hz), 7.32 (m, 2H), 7.05 (m, 2H), 6.78 (m, 1H), 3.82 (t, 2H, J=6.1 Hz), 2.68 (t, 2H, J=7.6 Hz), 2.55 (t, 2H, J=6.9 Hz), 1.86 (t, 2H, J=6.22 Hz), 1.62 (m, 2H), 0.94 (t, 3H, J=7.3 Hz).

Step B: Preparation of 5-(2-propyl-4-(4'-phenylphenoxy)phenyl)pentanol

The title compound was prepared according to the method described in Example 28, Step C, using 5-(2-propyl-4-(4'-phenylphenoxy)phenyl)pentyn-1-ol as the starting material.

$^1$H NMR (400 MHz, CDCl$_3$): δ 7.55 (m, 5H), 7.41 (t, 2H, J=7.3 Hz), 7.32 (m, 2H), 7.05 (m, 2H), 6.78 (m, 1H), 3.65 (t, 2H, J=6.5 Hz), 2.61–2.52 (m, 4H)), 1.63–1.44 (m, 8H), 0.95 (t, 3H, J=7.3 Hz).

Step C: Preparation of methyl (3-(5-(2-propyl-4-(4'-phenylphenoxy)phenyl)pentoxy)phenylacetate The title compound was prepared according to the method described in Example 28, Step D, using 5-(4-(4'-phenylphenoxy)-2-propylphenyl)-1-pentanol and methyl 3-hydroxyphenylacetate as the starting materials.

$^1$H NMR (400 MHz, CDCl$_3$): δ 7.55 (m, 4H), 7.42 (t, 2H, J=7.3 Hz), 7.38 (m, 1H), 7.02–7.11 (m, 4H), 6.79–6.86 (m, 5H), 3.95 (t, 2H, J=6.4 Hz), 3.67 (s, 3H), 3.57 (s, 2H), 2.60–2.53 (m, 4H)), 1.80 (m, 2H), 1.59–1.52 (m, 6H), 0.95 (t, 3H, J=7.3 Hz).

Step C: Preparation of 5-[3-(5-(2-propyl-4-(4'-phenylphenoxy)phenyl)pentoxy)phenyl]-2,4-thiazolidinedione The title compound was prepared according to the method described in Example 1, Step C, using methyl (3-(5-(2-propyl-4-(4'-phenylphenoxy)phenyl)pentoxy)phenylacetate as the starting materials.

$^1$H NMR (400 MHz, CDCl$_3$): δ 7.55–7.51 (m, 5H), 7.50–7.38 (m, 2H), 7.29–7.24 (m, 1H), 7.10–7.01 (m, 3H), 6.86–6.81 (m, 6H), 5.25 (s, 1H), 3.95 (brs, 2H), 2.60–2.52 (m, 4H)), 1.80 (m, 2H), 1.60–1.54 (m, 6H), 0.96 (t, 3H, 7.3 Hz).

CI-MS m/e=588.3 (M+Na).

EXAMPLE 36

5-[4-(4-(2-propyl-4-(4'-methoxyphenoxy)phenyl)butoxy)phenyl]-2,4-thiazolidinedione

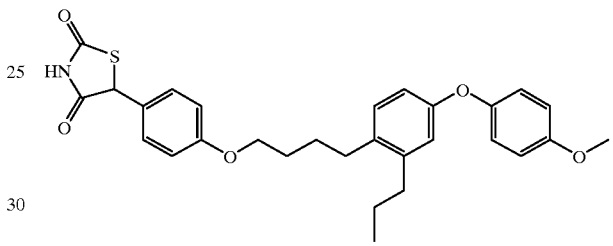

The title compound was prepared according to the method described in Example 35, using 4-(4'-methoxyphenoxy)-2-propylphenol in place of 4-(4'-phenylphenoxy)-2-propylphenol as the starting material in step A, and 3-butyn-1-ol in place of 4-pentyn-1-ol as the starting materials in step A (second paragraph).

$^1$H NMR (400 MHz, CDCl$_3$): δ 8.51 (brs, 1H), 7.31 (d, 2H), 7.24–6.74 (m, 9H), 5.32 (s, 1H), 3.96 (t, 2H, 6.3 Hz), 3.78 (s, 3H), 2.61 (t, 2H), 2.51 (t, 2H), 2.02–1.59 (m, 6H), 0.92 (t, 3H, J=7.3 Hz).

CI-MS m/e=505.6 (M+).

EXAMPLE 37

5-[3-(4-(2-propyl-4-(4'-fluorophenoxy)phenyl)butoxy)phenyl]-2,4-thiazolidinedione

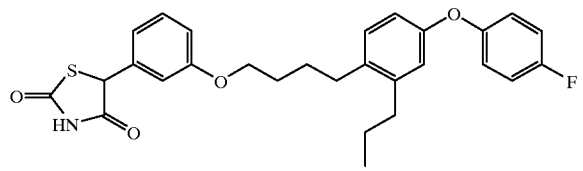

The title compound was prepared according to the method described in Example 35, using 4-(4-fluorophenoxy)-2-propylphenol in place of 4-(4-phenylphenoxy)-2-propylphenol as the starting material in step A, and 3-butyn-1-ol in place of 4-pentyn-1-ol as the starting materials in step A (second paragraph).

$^1$H NMR (400 MHz, CDCl$_3$): δ 8.51 (brs, 1H), 7.27 (t, 2H), 7.08–6.72 (m, 9H), 5.30 (s, 1H), 3.97 (m, 2H)), 2.63 (t, 2H), 2.52 (t, 2H), 1.85–1.54 (m, 6H), 0.92 (t, 3H, J=7.3 Hz).

CI-MS m/e=517.2 (M+Na).

EXAMPLE 38

5-[3-(5-(2-propyl-4-(4'-chlorophenoxy)phenyl)pentoxy)phenyl]-2,4-thiazolidinedione

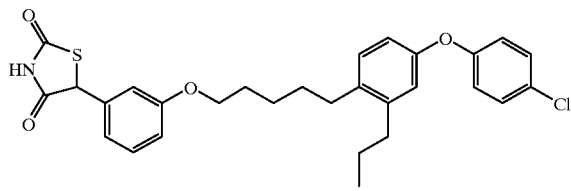

The title compound was prepared according to the method described in Example 35, using 4-(4-chlorophenoxy)-2-propylphenol in place of 4-(4-phenylphenoxy)-2-propylphenol as the starting material in step A.

$^1$H NMR (400 MHz, CDCl$_3$): δ 8.07 (brs, 1H), 7.31–6.71 (m, 11H), 5.31 (s, 1H), 3.96 (t, 2H), 2.61–2.51 (m, 4H)), 1.83 (m, 2H), 1.62–5.51 (m, 6H), 0.94 (t, 3H, J=7.3 Hz).

CI-MS m/e=546.2 (M+Na).

EXAMPLE 39

5-[3-(3-(2-propyl-4-(3'-methyl-4'-chlorophenoxy)phenoxy)propoxy)phenyl]-2,4-thiazolidinedione

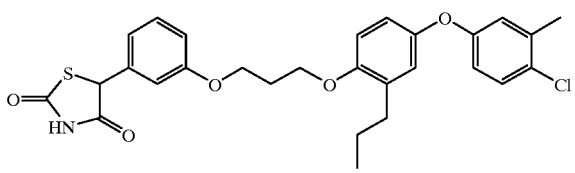

The title compound was prepared according to the method described in Example 23, using 4-chloro-3-methylphenol in place of 4-methylphenol as the starting material.

$^1$H NMR (400 MHz, CDCl$_3$): δ 8.04 (brs, 1H), 7.35–7.20 (m, 4H), 7.02–6.67 (m,6H), 5.32 (s, 3H), 4.19 (m, 4H), 2.55 (t, 2H, J=7.4 Hz), 2.26 (quint, 2H, J=6.3 Hz), 1.60 (hex, 2H, J=5.6 Hz), 0.89 (t, 3H, J=7.3 Hz).

CI-MS: m/e=544 (M+NH4).

EXAMPLE 40

5-[4-(3-(2-propyl-4-(4'-isobutylphenoxy)phenoxy)propoxy)phenyl]-2,4-thiazolidinedione

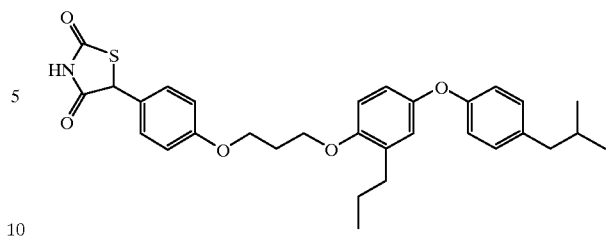

The title compound was prepared according to the method described in Example 23, using 4-isobutylphenol in place of 4-methylphenol as the starting material in step A.

$^1$H NMR (400 MHz, CDCl$_3$): δ 7.89 (brs, 1H), 7.34 (d, 2H), 7.06 (d, 2H), 7.04–6.78 (m, 7H), 5.35 (s, 1H), 4.2 (t, 2H), 4.16 (t, 2H), 2.54 (t, 2H, J=7.4 Hz), 2.41 (d, 2H), 2.25 (t, 2H), 1.81 (m, 1H), 1.57 (m, 4H), 1.23 (t, 3H, J=7.3 Hz), 0.90 (m, 9H).

CI-MS: m/e=533.35 (M+).

EXAMPLE 41

5-[3-(3-(2-propyl-4-(4'-cyclopentylphenoxy)phenoxy)propoxy)phenyl]-2,4-thiazolidinedione

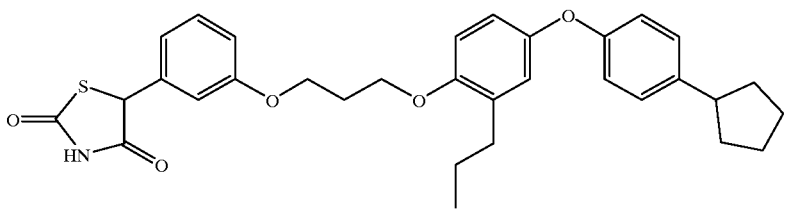

The title compound was prepared according to the method described in Example 23, using 4-cyclopentylphenol in place of 4-methylphenol as the starting material in Step A.

$^1$H NMR (400 MHz, CDCl$_3$): δ 9.79 (brs, 1H), 7.39 (t, 1H), 7.18 (d, 2H), 7.16–6.81 (m, 8H) 5.34 (s, 1H), 4.21 (t, 2H, J=6.2 Hz), 4.16 (t, 2H, J=6.0 Hz), 2.95 (quart, 1H), 2.56 (t, 2H, J=7.4), 2.30 (t, 2H, J=6.0 Hz), 2.07 (brm, 2H), 1.80–1.54 (m, 8H), 0.90 (m, 3H, 7.3 Hz).

CI-MS: m/e=545.38 (M+).

EXAMPLE 42

5-[3-(3-(2-propyl-4-(4'-isopropylphenoxy)phenoxy)propoxy)phenyl]-2,4-thiazolidinedione

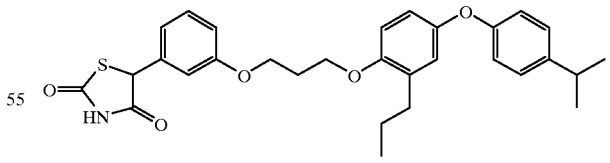

The title compound was prepared according to the method described in Example 23, using 4-isopropylphenol in place of 4-methylphenol as the starting material in Step A.

$^1$H NMR (400 MHz, CDCl$_3$): δ 8.23 (brs, 1H), 7.27 (d, 2H), 7.16 (d, 2H), 6.90 (d, 2H), 6.90–6.80 (m, 5H), 5.34 (s, 1H), 4.21 (t, 2H, J=6.2 Hz), 4.15 (t, 2H, J=6.1 Hz), 2.98 (quart, 1H), 2.57 (t, 2H, J=7.8 Hz), 2.30 (t, 2H), 1.64 (m, 2H), 1.26 (m, 6H), 0.96 (t, 3H, J=7.4 Hz).

CI-MS: m/e=521.2 (M+H).

EXAMPLE 43

5-[3-(3-(2-propyl-4-(naphthyloxy)phenoxy)propoxy)phenyl]-2,4-thiazolidinedione

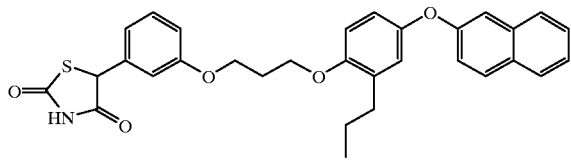

The title compound was prepared according to the method described in Example 23, using 2-naphthol in place of 4-methylphenol as the starting material in Step A.

$^1$H NMR (400 MHz, CDCl$_3$): δ 8.05 (s, 1H), 7.83 (d, 2H), 7.66 (d, 1H), 7.46–7.39 (m, 2H), 7.38–7.20 (m, 2H) 6.92–6.78 (m, 3H), 5.35 (s, 1H), 4.29 (m, 4H), 2.59 (t, 2H, J=7.4 Hz), 2.35 (t, 2H), 1.69 (quart, 4H), 0.99 (t, 3H).

CI-MS: m/e=528.3 (M+H).

EXAMPLE 44

5-(3-(3-(2-propyl-4-(dibenzofuran-2-yloxy)phenoxy)propoxy)phenyl]-2,4-thiazolidinedione

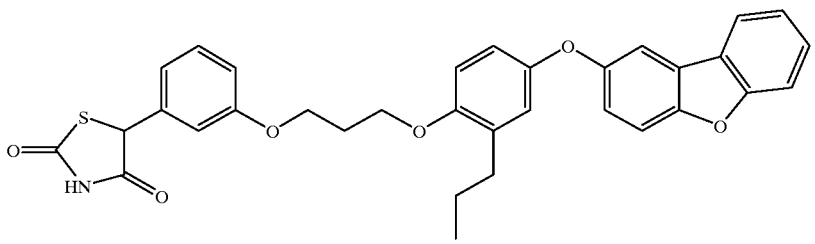

The title compound was prepared according to the method described in Example 23, using 2-hydroxydibenzofuran in place of 4-methylphenol as the starting material in Step A.

$^1$H NMR (400 MHz, CDCl$_3$): δ 7.99 (brs, 1H), 7.87 (d, 1H), 7.66–7.46 (m, 4H), 7.38–7.22 (m, 2H) 6.92–6.78 (m, 3H), 5.35 (s, 1H), 4.22 (t, 2H), 4.17 (t, 2H), 2.59 (t, 2H, J=7.4 Hz), 2.35 (t, 2H), 1.69 (quart, 2H), 0.99 (t, 3H).

CI-MS: m/e=567.3 (M+NH4).

EXAMPLE 45

5-[3-(3-(2,6-bispropyl-4-phenoxypropoxy)phenyl]-2,4-thiazolidinedione

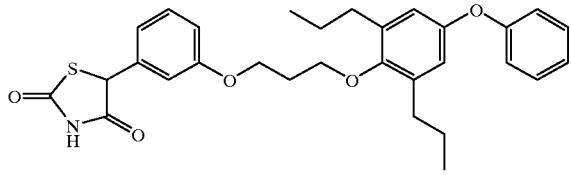

Step A: Preparation of 2,6-bispropyl-4-phenoxyphenol

To a solution of 4-phenoxy-2-propylphenol (PCT Application WO97/28115) in DMF was added potassium carbonate and allyl bromide. The reaction was stirred for 5 h at 50° C., and after cooling was neutralized with 1N HCl and extracted with ethyl acetate. The organic extract was washed with brine, dried over magnesium sulphate, filtered and concentrated to afford an oil which was chromatographed on silica gel (15% ethyl acetate:hexanes) to afford 2-propyl-4-phenoxyphenyl allyl ether.

The pure 2-propyl-4-phenoxy allyl ether was used to prepare the title compound according to the method described in Example 23, Step A, paragraphs 4 and 5.

$^1$H NMR (400 MHz, CDCl$_3$): δ 7.31–6.69 (ar, 7H), 4.49 (s, 1H), 2.54 (t, 4H, J=7.47 Hz), 1.59 (m, 4H), 0.96 (t, 6H, J=7.33 Hz).

Step B: Preparation of 5-[3-(3-(2,6-bispropyl-4-phenoxypropoxy)phenyl]-2,4-thiazolidinedione Using methyl 3-(3-bromopropoxy)mandelate and 2,6-bispropyl-4-phenoxyphenol (as prepared in Step A) as the starting materials for Example 22, Step B; the title compound was prepared according to the methods described in Example 22, Steps B through D.

$^1$H NMR (400 MHz, CDCl$_3$): 7.36–6.69 (ar, 11H), 5.35 (s, 1H), 4.26 (t, 2H, J=6.04 Hz), 3.94 (t, 2H, J=5.98 Hz), 2.52 (m, 4H), 2.27 (quint, 2H, J=6.05 Hz), 1.54 (m, 4H), 0.86 (t, 6H, J=7.36 Hz).

EXAMPLE 46

5-[4-(3-(7-propyl-3-neophyl-6-benz[4,5]isoxazolyloxy)propoxy)phenyl]-2,4-thiazolidinedione

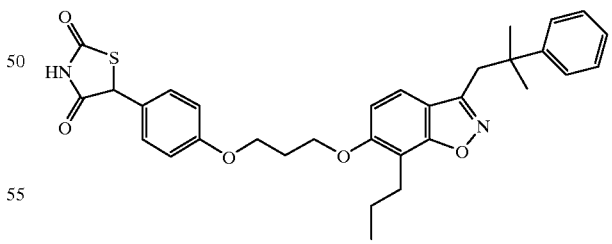

Step A: Preparation of methyl 4-(3-(7-propyl-3-neophyl-6-benz[4,5]isoxazolyloxy)propoxy)phenylacetate The title compound was prepared according to the method described in Example 1, Step B, using 7-propyl-3-neophyl-6-hydroxybenz[4,5]isoxazole (PCT Application WO97/28137) as the starting material.

$^1$H NMR (400 MHz, CDCl$_3$): δ 7.38 (d, 2H, J=7.32 Hz), 7.30–7.16 (ar, 9H), 6.85 (d, 2H, J=8.67 Hz), 6.67 (d, 1H, J=8.75 Hz), 6.50 (d, 1H, J=8.71 Hz), 4.15 (m, 4H), 3.66 (s,

3H), 3.55 (s, 2H), 3.18 (s, 2H), 2.81 (t, 2H, J=7.38 Hz), 2.25 (quint, 2H, J=6.06 Hz), 1.63 (hex, 2H, J=7.53 Hz), 1.44 (s, 6H), 0.91 (t, 3H, J=7.36 Hz).

Step B: Preparation of 5-[4-(3-(7-propyl-3-neophyl-6-benz[4,5]isoxazolyloxy)propoxy)phenyl]-2,4-thiazolidinedione The title compound was prepared according to the method described in Example 1, Step C, using methyl 4-(3-(7-propyl-3-neophyl-6-benz[4,5]isoxazolyloxy)propoxy)phenylacetate as the starting material.

$^1$H NMR (400 MHz, CDCl$_3$): δ 8.02 (brs, 1H), 7.38–7.16 (ar, 9H), 6.9 (d, 2H, J=8.71 Hz), 6.66 (d, 1H, J=8.79 Hz), 6.49 (d, 1H, J=8.78 Hz), 5.32 (s, 1H), 4.15 (m, 4H), 3.17 (s, 2H), 2.79 (t, 2H, J=7.61 Hz), 2.26 (quint, 2H, J=6.14 Hz), 1.60 (hex, 2H, J=6.14 Hz), 1.43 (s, 6H), 0.91 (t, 3H, J=7.45 Hz).

EXAMPLE 47

5-[3-(4-(7-propyl-3-trifluoromethyl-6-benz[4,5]-isoxazolyloxy)butoxy)phenyl]-2,4-thiazolidinedione

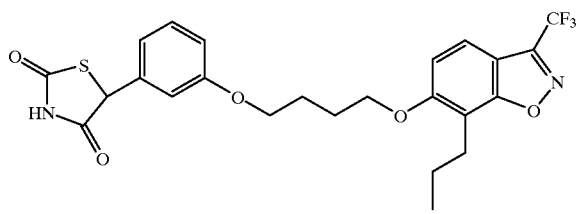

Step A: Preparation of Ethyl 3-(4-(7-propyl-3-trifluoromethyl-6-benz[4,5]isoxazolyloxy)butoxy)mandelate The title compound was prepared according to the method described in Example 22, Step C, using 7-propyl-3-trifluoromethyl-6-hydroxy-benz[4,5]isoxazole (PCT Application WO97/28137) and methyl 3-(4-bromobutoxy)mandelate as the starting materials.

$^1$H NMR (400 MHz, CDCl$_3$): δ 7.5 (d, 1H, J=8.5 Hz), 7.27–6.83 (ar, 5H), 4.28–4.24 (m, 2H), 4.17–4.031 (m, 4H), 2.89 (t, 2H, J=7.41 Hz), 1.22 (t, 3H, J=7.16 Hz), 0.94 (t, 3H, J=7.41 Hz).

Step B: Preparation of Ethyl α-chloro-3-(4-(7-propyl-3-trifluoromethyl-6-benz[4,5]isoxazolyloxy)butoxy)phenylacetate The title compound was prepared according to the method described in Example 22, Step D, using ethyl 3-(4-(7-propyl-3-trifluoromethyl-6-benz[4,5]isoxazolyloxy)butoxy)mandelate as the starting material.

$^1$H NMR (400 MHz, CDCl$_3$): δ 7.5 (d, 1H, J=8.5 Hz), 7.27–6.83 (ar, 5H), 5.28 (s, 1H), 4.28–4.24 (m, 2H), 4.17–4.031 (m, 4H), 2.89 (t, 2H, J=7.41 Hz), 1.22 (t, 3H, J=7.16 Hz), 0.94 (t, 3H, J=7.41 Hz).

Step C: Preparation of 5-[3-(4-(7-propyl-3-trifluoromethyl-6-benz[4,5]isoxazolyloxy)butoxy)phenyl]-2,4-thiazolidinedione The title compound was prepared according to the method described in Example 22, Step E, using ethyl α-chloro-3-(4-(7-propyl-3-trifluoromethyl-6-benz[4,5]isoxazolyloxy)butoxy)-phenylacetate as the starting material.

$^1$H NMR (400 MHz, CDCl$_3$): δ 8.18 (brs, 1H), 7.5 (d, 1H, J=8.14 Hz), 7.32–6.88 (ar, 5H), 5.31 (s, 1H), 4.16 (t, 2H, 5.78), 4.04 (t, 2H, 4.28), 2.89 (t, J=7.41 Hz), 2.03 (m, 4H), 1.67 (sext, 2H, 7.45), 0.94 (t, 3H, J=7.36 Hz).

EXAMPLE 48

5-[4-(3-(2-propyl-4-(4'-methoxyphenoxy)phenoxy)propoxy)-3-propylphenyl]-2,4-thiazolidinedione

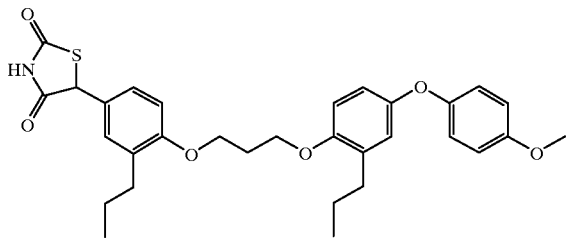

Step A: Preparation of of 4-(3-bromopropoxy)-3-propylphenyl phenyl ether

The title compound was prepared according to the method described in Example 11, Step A, using 2-propyl-4-(4'-methoxyphenoxy)phenol (as prepared in Example 23, Step A using 4-methoxyphenol) as the starting material.

Step B: Preparation of methyl 4-(3-(2-propyl-4-(4'-methoxyphenoxy)phenoxy)propoxy)-3-propylphenylacetate The title compound was prepared according to the method described in Example 11, Step B, using methyl 4-hydroxy-3-propylphenylacetate and 4-(3-bromopropoxy)-3-propylphenyl phenyl ether (as prepared in Step A) as the starting materials.

$^1$H NMR (400 MHz, CDCl$_3$): δ 7.09–6.74 (ar, 10H), 4.19–4.14 (m, 4H), 3.81 (s, 3H), 3.70 (s, 3H), 3.56 (s, 2H), 2.60–2.54 (quint, 4H, J=7.6 Hz), 2.29 (quint, 2H,J=6 Hz), 1.59 (quint,4H, J=7.7), 0.93 (quart, 6H, J=6.7 Hz).

Step C: Preparation of 5-[4-(3-(2-propyl-4-(4'-methoxyphenoxy)phenoxy)propoxy)-3-propylphenyl]-2,4-thiazolidinedione The title compound was prepared according to the method described in Example 1, Step C, using methyl 4-(3-(2-propyl-4-(4'-methoxy phenoxy)phenoxy)propoxy)-3-propylphenylacetate as the starting material.

$^1$H NMR (400 MHz, CDCl$_3$): δ 7.89 (brs, 1H), 7.29–6.74 (ar, 10H), 5.34 (s, 1H), 4.20 (t, 2H, J=6.1 Hz), 4.15 (t, 2H, 5.8 Hz 3.81 (s, 3H), 2.61–2.53 (m, 4H), 2.3 (quint, 2H,J=6.1 Hz), 1.57 (m, 4H), 0.92 (m, 6H).

EXAMPLE 49

5-[4-(4-(2-propyl-4-(4'-methoxyphenoxy)phenoxy)butoxy)phenyl]-2,4-thiazolidinedione

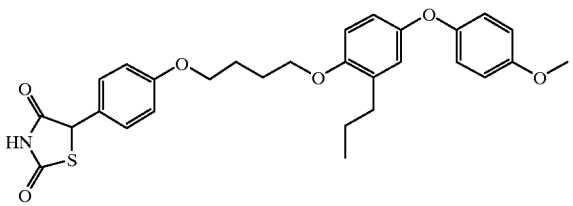

Step A: Preparation of ethyl 4-(4-(2-propyl-4-(4'-methoxyphenoxy)phenoxy)butoxy)mandelate The title compound was prepared according to the method described in Example 22, Step C, using and ethyl 4-(4-bromobutoxy)mandelate and 2-propyl-4-(4'-methoxyphenoxy)phenol (as prepared in Example 23, Step A using 4-methoxyphenol) as the starting materials. as the starting material.

$^1$H NMR (400 MHz, CDCl$_3$): δ 7.31–7.29 (m, 2H), 7.02–6.76 (m, 9H), 5.09–5.07 (d, 1H,J=5.7 Hz), 4.27–4.04

(m, 2H), 4.02–3.96 (m, 4H), 3.36 (d, 1H, J=5.8 Hz), 2.53 (t, 2H, J=7.41 Hz), 0.90 (t, 3H, J=7.32 Hz).

Step B: Preparation of ethyl α-chloro-4-(4-(2-propyl-4-(4'-methoxyphenoxyphenoxy)butoxy)phenylacetate The title compound was prepared according to the method described in Example 22, Step D, using ethyl 4-(4-(2-propyl-4-(4'-methoxyphenoxy)phenoxy)butoxy)mandelate (as prepared in Step A) as the starting material.

¹H NMR (400 MHz, CDCl3): d. 7.40–7.38 (d, 2H, J=8.78 Hz); 6.91–6.72 (ar, 9H); 5.28 (s, 1H); 4.23–4.17 (m, 2H); 4.04–3.96 (m, 4H); 2.53 (t, 2H, J=7.61 Hz), 0.90 (t, 3H, J=7.36 Hz).

Step C: Preparation of 5-[4-(4-(2-propyl-4-(4'-methoxyphenoxy)phenoxy)butoxy)phenyl]-2,4-thiazolidinedione The title compound was prepared according to the method described in Example 22, Step E, using ethyl α-chloro-4-(4-(2-propyl-4-(4'-methoxy)phenoxy)phenoxy)butoxy)phenylacetate (as prepared in Step B) as the starting material.

¹H NMR (400 MHz, CDCl₃): δ 8.18 (brs, 1H), 7.40–7.38 (d, 2H, J=8.78 Hz); 6.91–6.72 (ar, 9H); 5.32 (s, 1H); 4.04–3.95 (m, 4H); 2.53 (t, 2H, J=7.61 Hz), 1.95 (m, 4H), 1.56 (sext, 2H, 7.5), 0.90 (t, 3H, J=7.36 Hz).

EXAMPLE 50

5-[4-(4-(2-propyl-4-(4'-flourophenoxy)phenoxy)butoxy)phenyl]-2,4-thiazolidinedione

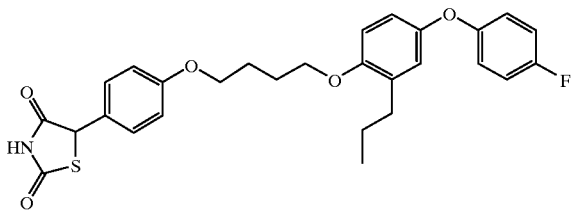

Step A: Preparation of ethyl 4-(4-(2-propyl-4-(4'-flourophenoxy)phenoxy)butoxy)mandelate The title compound was prepared according to the method described in Example 22, Step C, using 2-propy-4-(4'-flourophenoxy)phenol (as prepared in Example 26 using 4-fluorophenol) and ethyl 4-(4-bromobutoxy)-mandelate as the starting material.

¹H NMR (400 MHz, CDCl₃): δ 7.31 (d, 2H), 6.98–6.74 (ar, 9H), 5.10 (d, 1H,J=5.78 Hz), 4.25–4.11 (m, 2H), 4.09–3.97 (m, 4H), 3.36 (d, 1H, J=5.77 Hz), 2.54 (t, 2H, J=7.57 Hz), 0.90 (t, 3H, J=7.37 Hz).

Step B: Preparation of ethyl α-chloro-4-(4-(2-propyl-4-(4'-flourophenoxy)phenoxy)butoxy)phenylacetate The title compound was prepared according to the method described in Example 22, Step D, using ethyl 4-(4-(2-propyl-4-(4'-flourophenoxy)phenoxy)butoxy)mandelate (as prepared in Step A) as the starting material.

¹H NMR (400 MHz, CDCl₃): δ 7.4 (d, 2H), 6.98–6.75 (ar, 9H), 5.28 (s, 1H), 4.25–4.15 (m, 2H), 4.05–3.97 (m, 4H), 2.54 (t, 2H, J=7.33 Hz), 0.90 (t, 3H, J=7.33 Hz).

Step C: Preparation of 5-[4-(4-(2-propyl-4-(4'-flourophenoxy)-phenoxy)-butoxy)phenyl]-2,4-thiazolidinedione The title compound was prepared according to the method described in Example 22, Step E, using ethyl α-chloro-4-(4-(2-propyl-4-(4'-flourophenoxy)phenoxy)butoxy) phenylacetate (as prepared in Step B) as the starting material.

¹H NMR (400 MHz, CDCl₃): δ 8.08 (broad s, 1H), 7.32 (s, 1H,), 7.30 (s, 1H), 6.98–6.74 (ar, 9H), 5.33 (s, 1H), 4.04 (t, 2H, J=5.82 Hz), 3.98 (t, 2H, J=7.68 Hz), 2.54 (t, 2H, J=7.6 Hz), 2.28 (q, 2H, J=6.4 Hz), 1.55(hex, 2H, J=7.4 Hz), 0.90 (t, 3H, J=7.3 Hz)

EXAMPLE 51

5-[3-(4-(2-propyl-4-(4'-methoxyphenoxy)phenoxy)butoxy)phenyl]-2,4-thiazolidinedione

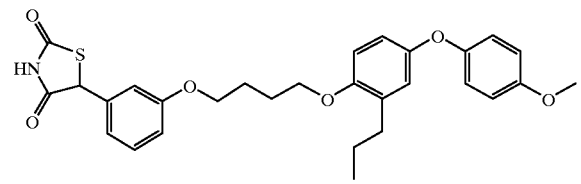

Step A: Preparation of 4-(4-bromobutoxy)-3-propyl(4'-methoxyphenyl)phenyl ether

The title compound was prepared according to the method described in Example 15, Step A, using 2-Propyl-4-(4'-methoxyphenoxy) phenol (as prepared in Example 23, Step A using 4-methoxyphenol) as the starting material.

Step B: Preparation of methyl 3-(4-(2-propyl-4-(4'-methoxyphenoxy)phenoxy)butoxy)phenylacetate The title compound was prepared according to the method described in Example 15, Step B, using methyl 3-hydroxyphenylacetate and 4-(4-bromobutoxy)-3-propylphenyl 4-methoxyphenyl ether as the starting materials.

¹H NMR (400 MHz, CDCl₃): δ 7.24–7.19 (m, 2H), 6.91–6.73 (ar, 9H), 4.02–3.96 (m, 4H), 3.77 (s, 3H), 3.67 (s, 3H), 3.57 (s, 2H), 2.54 (t, 2H, J=7.41 Hz), 0.90 (t, 3H, J=7.33 Hz).

Step B: Preparation of 5-[3-(4-(2-propyl-4-(4'-methoxyphenoxy)phenoxy)butoxy)phenyl]-2,4-thiazolidinedione The title compound was prepared according to the method described in Example 1, Step C, using methyl 3-(4-(2-propyl-4-(4'-methoxyphenoxy)phenoxy)butoxy) phenylacetate as the starting material.

¹H NMR (400 MHz, CDCl₃): δ 8.14 (brs, 1H), 7.3 (m, 1H), 6.98–6.69 (m, 10H), 5.31 (s, 1H), 4.00 (m, 4H), 3.77 (s, 3H), 2.53 (t, 2H, J=7.52 Hz), 2.03 (m, 4H), 1.59 (m, 2H), 0.90 (t, 3H, J=7.32 Hz).

EXAMPLE 52

5-[3-(4-(2-propyl-4-(4'-chlorophenoxy)phenoxy)butoxy)phenyl]-2,4-thiazolidinedione

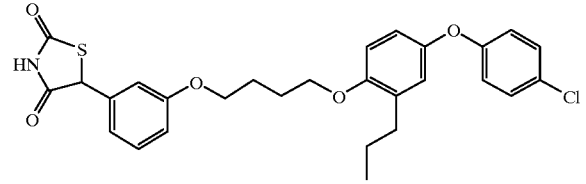

Step A: Preparation of 4-(4-bromobutoxy)-3-propylphenyl 4-chlorophenyl ether

The title compound was prepared according to the method described in Example 15, Step A, using 2-Propyl-4-(4'-chlorophenoxy)phenol (as prepared in Example 23, Step A using 4-chlorophenol) as the starting material Step B: Preparation of methyl 3-(4-(2-propyl-4-(4'-chlorophenoxy)phenoxy)butoxy)phenylacetate The title compound was prepared according to the method described in Example 15, Step B, using 4-(4-bromobutoxy)-3-propylphenyl 4-chlorophenyl ether and methyl 3-hydroxyphenylacetate as the starting materials.

$^1$H NMR (400 MHz, CDCl$_3$): δ 7.23–7.19 (m, 2H), 6.86–6.78 (ar, 9H), 4.04 (m, 4H), 3.68 (s, 3H), 3.58 (s, 2H), 2.55 (t, 2H, J=7.33 Hz), 0.90 (t, 3H, J=7.36 Hz).

Step B: Preparation of 5-[3-(4-(2-propyl-4-(4'-chlorophenoxy)phenoxy)butoxy)phenyl]-2,4-thiazolidinedione The title compound was prepared according to the method described in Example 1, Step C, using methyl 3-(4-(2-propyl-4-(4'-chlorophenoxy)phenoxy)butoxy)phenylacetate as the starting material.

$^1$H NMR(400 MHz, CDCl$_3$): 8.22 (brs, 1H), 7.32–7.20 (m,2H), 6.99–6.77 (m, 9H), 5.31 (s, 1H), 4.00 (m, 4H), 2.54 (t, 2H, J=7.32 Hz), 2.00 (m, 4H), 1.59 (m, 2H), 0.90 (t, 3H, J=7.33 Hz).

EXAMPLE 53

5-[3-(3-(2-propyl-4-(4'-methylsulfonylphenoxy) phenoxypropoxy)phenyl]-2,4-thiazolidinedione

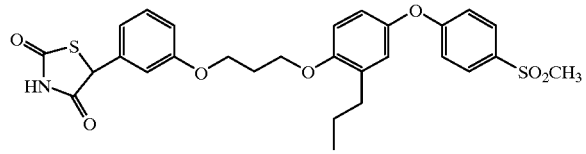

Step A: Preparation of methyl 3-(3-(2-propyl-4-(4'-methylsulfonylphenoxy)phenoxypropoxy)mandelate The title compound was prepared according to the method described in Example 22, Step C using methyl 3-(3-bromopropoxy)mandelate as the starting material.

$^1$H NMR (400 MHz, CDCl$_3$): δ 7.81 (m, 2H); 7.00–6.84 (ar, 9H), 5.13 (d, 1H, J=5.58 Hz), 4.19–4.13 (m, 4H), 3.74 (s, 3H), 3.41 (d, 1H, J=5.62 Hz), 3.02 (s, 3H), 2.56 (t, 3H, J=7.52 Hz), 0.90 (t,3H, J=7.33 Hz).

Step B: Preparation of methyl α-chloro-3-(3-(2-propyl-4-(4'-methylsulfonylphenoxy)phenoxy)propoxy) phenylacetate The title compound was prepared according to the method described in Example 22, Step D using methyl 3-(3-(2-propyl-4-(4'-methylsulfonylphenoxy)phenoxy)propoxy) mandelate (as prepared in Step A) as the starting material.

$^1$H NMR (400 MHz, CDCl$_3$): δ 7.86 (m, 2H), 7.27–6.85 (ar, 9H), 5.30 (s, 1H), 4.20–4.13 (m, 4H), 3.75 (s, 3H), 3.02 (s, 3H), 2.56 (t, 2H, 7.49), 0.90 (t, 3H, J=7.32 Hz).

Step C: Preparation of 5-[3-(3-(2-propyl-4-(4'methylsulfonylphenoxy)phenoxy)propoxy)phenyl]-2,4-thiazolidinedione The title compound was prepared according to the method described in Example 22, Step E using ethyl α-chloro-3-(3-(2-propyl-4-(4'-methylsulfonylphenoxy)phenoxy)propoxy) phenylacetate as the starting material.

$^1$H NMR (400 MHz, CDCl$_3$): δ 8.20 (brs, 1H), 7.84 (m, 2H), 7.30–6.83 (ar, 9H), 5.35 (s, 1H), 4.16 (t, 2H, J=6.71 Hz), 4.06 (t, 2H, J=6.43 Hz), 3.02 (s, 3H), 2.56 (t, 2H, 6.8 Hz), 2.28 (quint, 2H, J=6.02 Hz), 1.55 (m, 2H), 0.90 (t, 3H, J=7.32 Hz).

EXAMPLE 54

5-[3-(4-(2-propyl-4-(4'-methylsulfonylphenoxy) phenoxy)butoxy)phenyl]-2,4-thiazolidinedione

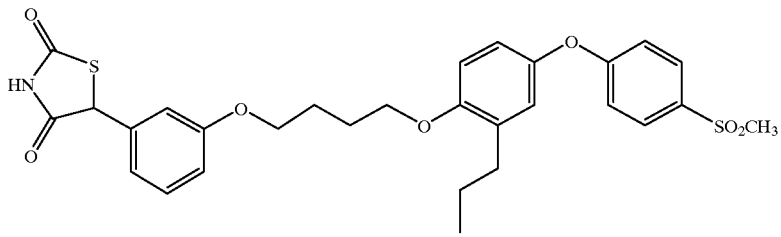

Step A: Preparation of methyl 3-(4-(2-propyl-4-(4'-methylsulfonylphenoxy)phenoxy)butoxy)mandelate The title compound was prepared according to the method described in Example 22, Step C using methyl 3-(4-bromobutoxy)mandelate as the starting material.

$^1$H NMR (400 MHz, CDCl$_3$): δ 7.82 (m, 2H); 7.26–6.83 (ar, 9H), 5.13 (d, 1H, J=5.58 Hz), 4.07–4.02 (m, 4H), 3.74 (s, 3H), 3.41 (d, 1H, J=5.62 Hz), 3.02 (s, 3H), 2.57 (t, 3H, J=7.24 Hz), 2.0 (m, 4H), 0.90 (t,3H, J=7.33 Hz).

Step B: Preparation of methyl α-chloro-3-(3-(2-propyl-4-(4'-methylsulfonylphenoxy)phenoxy)butoxy)phenylacetate The title compound was prepared according to the method described in Example 22, Step D using methyl 3-(4-(2-propyl-4-(4'-methylsulfonylphenoxy)phenoxy)butoxy) mandelate as the starting material.

$^1$H NMR (400 MHz, CDCl$_3$): δ. 7.86 (m, 2H), 7.27–6.85 (ar, 9H), 5.30 (s, 1H), 4.07–4.02 (m, 4H), 3.75 (s, 3H), 3.02 (s, 3H), 2.57 (t, 2H, J=7.24 Hz), 0.90 (t, 3H, J=7.32 Hz).

Step C: Preparation of 5-[3-(4-(2-propyl-4-(4'methylsulfonylphenoxy)phenoxy)butoxy)phenyl]-2,4-thiazolidinedione The title compound was prepared according to the method described in Example 22, Step E using ethyl α-chloro-3-(3-(2-propyl-4-(4'-methylsulfonylphenoxy)phenoxy)butoxy) phenylacetate as the starting material.

$^1$H NMR (400 MHz, CDCl$_3$): δ 8.20 (brs, 1H), 7.84 (m, 2H), 7.30–6.83 (ar, 9H), 5.35 (s, 1H), 4.16 (t, 2H, J=6.71 Hz), 4.06 (t, 2H, J=6.43 Hz), 3.02 (s, 3H), 2.56 (t, 2H, 6.8 Hz), 2.28 (quint, 2H, J=6.02 Hz), 2.0 (m, 4H), 0.90 (t, 3H, J=7.32 Hz).

EXAMPLE 55

5-[4-(3-(2-propyl-5-phenoxy)phenoxypropoxy)phenyl]-2,4-thiazolidinedione

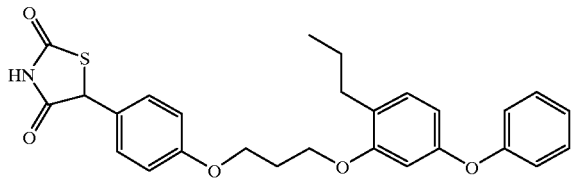

Step A: Preparation of 2-propyl-5-phenoxyphenol

A solution of 1-phenoxy-(3-propenyloxy)benzene(29.0 g) in ortho-dichlorobenzene (200 mL) was refluxed for 24 h. Mixture was cooled to room temperature and was chromatographed to afford two intermediates labelled 1(3.33 g) and 2 (2.81 g). Compound 1 was hydrogenated over Pd/C catalyst (0.8 g) in methanol. The reaction was filtered through Celite and all volatiles were removed to afford the title compound.

$^1$H NMR (400 MHz, CDCl$_3$): δ 7.16–7.01 (m, 6H,); 6.54 (dd, 1H, J=8.2 Hz and J=2.3 Hz); 6.45 (d,1H, J=2.3 Hz); 4.72 (s,1H); 2.56 (t, 2H, J=7.5 Hz); 1.64 (m.2H); 0.98 (t, 3H, J=7.4 Hz).

Step B: Preparation of Methyl 3-(3-(2-propyl-5-phenoxyphenoxy)propoxy)phenylacetate The title compound was prepared according to the method described in Example 1, Step B, using as 2-propyl-5-phenoxyphenol as the starting material.

$^1$H NMR (400 MHz, CDCl$_3$): δ 7.31–6.82 (m, 10H,); 6.55 (d,1H, J=2.3 Hz); 6.52 (dd, 1H, J=8.2 Hz and J=2.3 Hz); 4.13 (t, 2H, J=6.2 Hz); 4.05 (t, 2H, J=6.0 Hz); 3.66 (s, 3H); 3.54 (s, 2H); 2.52 (t, 2H, J=7.4 Hz); 2.23 (quit, 2H, J=6.2 Hz); 1.54(hex, 2H, J=7.4 Hz); 0.9 (t, 3H, J=7.3 Hz).

Step C: Preparation of 5-[4-(3-(2-propyl-5-phenoxyphenoxy)propoxy)phenyl]-2,4-thiazolidinedione The title compound was prepared according to the method described in Example 1, Step C, using methyl 3-(3-(2-propyl-5-phenoxyphenoxy)propoxy)phenylacetate (as prepared in Step B) as the starting material.

$^1$H NMR (400 MHz, CDCl$_3$): δ 7.95 (brs, 1H), 7.31–6.87 (m, 10H,); 6.55 (d, J=2.3 Hz); 6.52 (dd, 1H, J=8.2 Hz and J=2.3 Hz); 5.32 (s, 1H); 4.13 (t, 2H, J=6.2 Hz); 4.05 (t, 2H, J=6.0 Hz); 2.52 (t, 2H, J=7.4 Hz); 2.23 (quit, 2H, J=6.2 Hz); 1.54 (hex, 2H, J=7.4 Hz); 0.9 (t, 3H, J=7.3 Hz).

EXAMPLE 56

5-[4-(3-(2-propyl-3-(phenoxyphenoxy)propoxy)phenyl]-2,4-thiazolidinedione

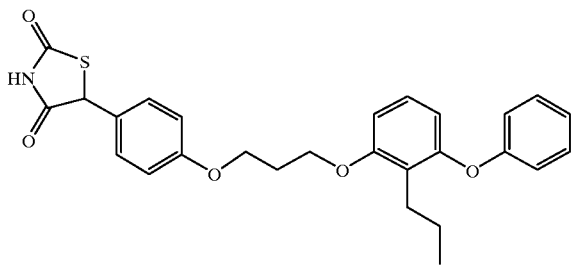

Step A: Preparation of 2-propyl-3-phenoxyphenol

The intermediate 2 (2.81 g) obtained as described in Example 55, Step A, was was hydrogenated over Pd/C catalyst (0.61 g) in methanol. The reaction was filtered through celite and all volatiles were removed to afford the title compound.

$^1$H NMR (400 MHz, CDCl$_3$): δ 7.34–6.95 (m, 6H,); 6.6 (d, 1H, J=8.0 Hz); 6.48 (d,1H, J=8.0 Hz); 4.8 (s,1H); 2.65 (t, 2H, J=7.6 Hz); 1.64 (m.2H); 0.97 (t, 3H, J=7.4 Hz).

Step B: Preparation of Methyl 3-(3-(2-propyl-3-(phenoxyphenoxy)propoxy)phenylacetate The title compound was prepared according to the method described in Example 1, Step B, using as 2-propyl-3-phenoxyphenol the starting material.

$^1$H NMR (400 MHz, CDCl$_3$): δ 7.29–6.85 (m, 10H,); 6.65 (d,1H, J=7.7 Hz); 6.49 (d, 1H, J=8.2 Hz); 4.17–4.13 (m, 4H,); 3.66 (s, 3H); 3.54 (s, 2H); 2.6 (t, 2H, J=7.6 Hz); 2.27 (quit, 2H, J=6.1 Hz); 1.5(hex, 2H, J=7.6 Hz); 0.87 (t, 3H, J=7.3 Hz).

Step C: Preparation of 5-[4-(3-(2-propyl-3-(phenoxyphenoxy)propoxy)phenyl]-2,4-thiazolidinedione The title compound was prepared according to the method described in Example 1, Step C, using methyl 3-(3-(2-propyl-3-phenoxyphenoxy)propoxy)phenylacetate (as prepared in Step B) as the starting material.

$^1$H NMR (400 MHz, CDCl$_3$): δ 8.05 (brs, 1H), 7.32–6.88 (m, 10H,); 6.64 (d, 1H, J=7.4 Hz); 6.49 (d, 1H, J=7.3); 5.32 (s, 1H); 4.2–4.13 (m, 4H); 2.6 (t, 2H, J=7.3 Hz); 2.28 (quit, 2H, J=6.0 Hz); 1.49 (hex, 2H, J=7.5Hz); 0.86 (t, 3H,J=7.3 Hz).

EXAMPLE 57

5-[3-(4-(2-propyl-3-(phenoxyphenoxy)butoxy)phenyl]-2,4-thiazolidinedione

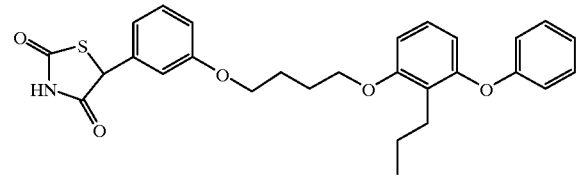

The title compound was prepared according to the method described in Example 22 (Step B-E) using ethyl 3-(4-bromobutoxy)mandelate and 2-propyl-3-phenoxyphenol (Example56, Step A).

$^1$H NMR (400 MHz, CDCl$_3$): δ 7.96 (brs, 1H), 7.36–6.93 (m, 10H,); 6.8 (d, 1H, J=8.2 Hz); 6.53 (d, 1H, J=8.3); 5.35 (s, 1H); 4.08 (m, 4H); 2.66 (t, 2H, J=7.6 Hz); 2.03 (m, 4H); 1.56 (m, 2H); 0.92 (t, 3H, J=7.4 Hz).

EXAMPLE 58

5-[3-(3-(2-(2-propenyl)-4-(phenoxyphenoxy)propoxyphenyl]-2,4-thiazolidinedione

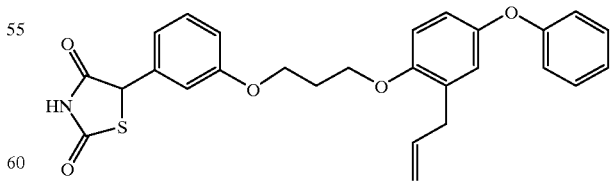

Step A: Preparation of 2-(2-propenyl)-4-phenoxyphenol

A solution of 1-phenoxy-(4-propenyloxy)benzene (11.0 g) in ortho-dichlorobenzene (150 mL) was kept at reflux for 24 h. Mixture was cooled to room teperature and chromatographed over silica gel to afford the title compound (10.3 g).

¹H NMR (400 MHz, CDCl₃): δ 7.4–6.76 (m, 8H,); 6.06–5.96 (m, 1H); 5.21–5.15 (ddt, 2H); 4.86 (s,1H); 3.4 (d, 2H, J=1.4 Hz).

Step B: Preparation of 5-[3-(3-(2-(2-propenyl)-4-(phenoxyphenoxy)propoxyphenyl]-2,4-thiazolidinedione The title compound was prepared according to the method described in Example 22 (Step B-E) using ethyl 3-(3-bromopropoxy)mandalate and 2-(2-propenyl)-4-phenoxyphenol.

¹H NMR (400 MHz, CDCl₃): δ 8.25 (brs, 1H), 7.35–6.83 (m, 12H,); 5.97–5.88 (m, 1H); 5.32 (s, 1H); 5.05–5.0 (m, 4H); 4.17 (dt, 4H); 2.28 (m, 2H).

EXAMPLE 59

5-[3-(3-(1'-fluoropropyl)-4-phenoxyphenoxy)propoxyphenyl]-2,4-thiazolidinedione

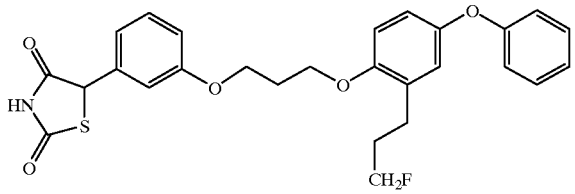

Step A: Preparation of 2-(1'-fluoropropyl)-4-phenoxyphenol

To a solution of 2-(2-propenyl)-4-phenoxyphenol (5.0 g, Example 58-Step A) in tetrahydrofuran (THF, 40 mL) was added at 0° C., a solution of borane-methyl sulfide in THF (1.25 M equiv). The solution was stirred for 3 h during which temperature was allowed to rise to room temerature. Absolute ethanol (10 mL) was then added followed by addition of sodium hydroxide (2.27 g) in water (10 mL). The solution was then cooled to 0° C. and 4.5 mL of 30% hydrogen peroxide solution was carefully added. The reaction mixture was partitioned between water and ether. The ether extracts were washed with water, brine and dried over sodium sulfate. Concentration under reduced pressure followed by chromatography over silica gel afforded the desired intermediate.

¹H NMR (400 MHz, CDCl₃): δ 7.33–6.9 (m, 8H); 4.12 (t, 2H, J=5.2 Hz); 3.68 (t, 2H, J=5.9 Hz); 2.77 (t, 2H, J=6.8 Hz); 1.89 (hex, 2H, J=5.9 Hz).

This intermediate (2.2 g) was dissolved in tetrahydrfuran (30 mL) and treated with diethylaminosulfur trifluoride (DAST)(4.76 mL) at 0° C. The solution was stirred for 4 h, quenched by addition of aqueous NaHCO₃, washed with water, dried(Na₂SO₄), concentrated, and chromatographed over silica gel to provide 2-(1'-fluoropropyl)-4-phenoxyphenol.

¹H NMR (400 MHz, CDCl₃): δ 7.33–6.75 (m, 8H,); 4.69 (s, 1H); 4.45 (dt, 2H, J=47.3 Hz and 5.9 Hz); 2.74 (t, 2H, J=7.3 Hz); 2.05 (m, 2H).

Step B: Preparation of 5-[3-(3-(1'fluoropropyl)-4-(phenoxyphenoxy)propoxyphenyl]-2,4-thiazolidinedione The title compound was prepared according to the method described in Example 22 (Step B'E) using ethyl 3-(3-bromoprpoxy)mandalate and 2-(1'-fluoropropyl)-4-phenoxyphenol.

¹H NMR (400 MHz, CDCl₃): δ 7.94(brs, 1H); 7.4–6.8 (m, 12H,); 5.35 (s, 1H); 4.44 (dt, 2H, J=47.3 Hz and 5.9 Hz); 4.22 (t, 2H, J=6.1 Hz); 4.17 (t, 2H, J=6.1 Hz); 2.73 (t, 2H, J=7.2 Hz); 2.3 (m, 2H); 1.95 (m, 2H).

EXAMPLE 60

5-[3-(3-(2-propyl-4-(4'-ethoxycarbonylphenoxy)phenoxypropoxy)phenyl]-2,4-thiazolidinedione

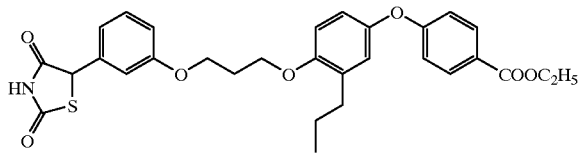

Step A: Preparation of 2-Propyl-4-(4'-ethoxycarbonyl)phenoxyphenol

A solution of 4-allyloxyphenol (10.0 g), 4-fluoroethylbenzoate (12.33 g) and sodium hydride (2.93 g, 60% disperson in mineral oil) in dimethyl sulfoxide (50 mL) was stirred at 150° C. for 24 h. The solution was cooled and the excess was carefully destroyed using water. The reaction mixture was extracted with ethyl acetate, washed with water and dried over sodium sulfate. The organic layer was filtered and evaporated to an oil which was chromatographed over silica gel to afford 4-(4'-ethoxycarbonylphenoxy)phenyl allyl ether.

A solution of 4-(4'-ethoxycarbonylphenoxy)phenyl allyl ether (3.9 g) in 1,2-dichlorobenzene (50 mL) was heated at reflux for 30 h. After cooling to room temperature, mixture was chromatographed over silica gel to afford the intermediate (3.46 g) which was hydrogenated over Pd/C (0.3 g) in ethanol (130 mL). The reaction was filtered through Celite and concentrated in vacuo to afford 2-propyl-4-(4'-ethoxycarbonylphenoxy)phenol.

¹H NMR (400 MHz, CDCl₃): δ 7.99 (d, 2H, J=9.0 Hz), 6.93 (d, 2H, J=9.0 Hz); 6.87 (s, 1H); 6.8 (dd, 2H); 4.36 (q, 2H, J=7.0 Hz); 2.59 (t, 2H, J=7.4 Hz); 1.68–1.60 (m, 2H); 0.98 (t, 3H, J=7.2 Hz)

Step B: Preparation of 5-[3-(3-(2-propyl-4-(4'-ethoxycarbonylphenoxy)phenoxypropoxy)phenyl]-2,4-thiazolidinedione The title compound was prepared according to the method described in Example 22 (Step B'E) using ethyl 3-(3-bromoprpoxy)mandalate and 2-propyl-4-(4'-ethoxycarbonyl)phenoxyphenol.

¹H NMR (400 MHz, CDCl₃): δ 8.0 (d and brs, 3H); 7.4–6.8 (m, 9H,); 5.35 (s, 1H); 4.36 (q, 2H, J=7.0 Hz); 4.22 (t, 2H, J=6.1 Hz); 4.18 (t, 2H, J=6.0 Hz); 2.59 (t, 2H, J=7.4 Hz); 2.32 (hex, 2H, J=6.0 Hz); 1.6 (m, 2H); 1.39 (t, 3H, J=7.3 Hz); 0.93 (t, 3H, J=7.2 Hz).

EXAMPLE 61

5-[4-(3-(4-(1,2-benzisoxazol-3-yl)-2-propylphenoxy)propoxy)phenyl]-2,4-thiazolidinedione

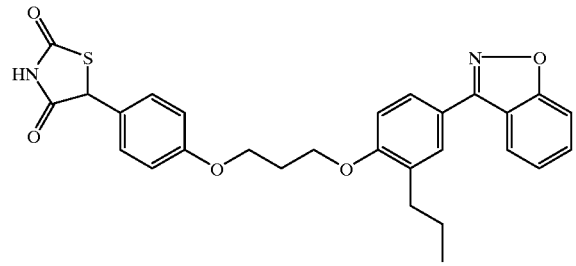

The title compound was prepared according to the method described in Example 22 (Step B'E) using ethyl 4-(3- bromoprpoxy)mandalate and 4-(1,2-benzisoxazol-3-yl)-2-propylphenol (PCT Application WO97/28115)

$^1$H NMR (400 MHz, CDCl$_3$): δ 7.91 (brs, 1H), 7.9–6.9 (m, 11H,); 5.33 (s, 1H); 4.21 (q, 2H, J=6.2 Hz); 4.22 (t, 2H, J=6.1 Hz); 2.66 (t, 2H, J=7.5 Hz); 2.32 (hex, 2H, J=6.0 Hz); 1.64 (m, 2H); 0.95 (t, 3H, J=7.3 Hz).

EXAMPLE 62

5-[3-(4-((1,2-benzisoxazol-3-yl)-2-propylphenoxy)butoxy)phenyl]-2,4-thiazolidinedione

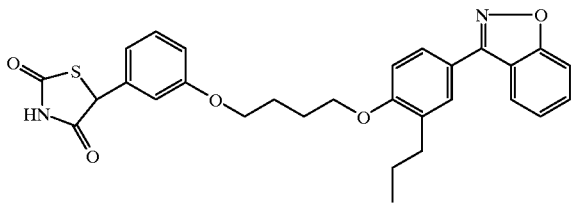

The title compound was prepared according to the method described in Example 22 using ethyl 3-(4-bromobutoxy)mandelate and 4-(1,2-benzisoxazol-3-yl)-2-propylphenol (PCT Application WO97/28115)

$^1$H NMR (400 MHz, CDCl$_3$): δ 8.31 (brs, 1H), 7.9–6.9 (m, 11H,); 5.31 (s, 1H); 4.12 (t, 2H, J=5.2 Hz); 4.06 (t, 2H, J=5.0 Hz); 2.67 (t, 2H, J=7.7 Hz); 2.0 (m, 4H); 1.66 (m, 2H); 0.96 (t, 3H, J=7.3 Hz).

EXAMPLE 63

5-[4-(3-(3-(2-phenylethyl)-7-propyl-benzothiophen-6-yl)oxy)-1-propoxy]phenyl-2,4-thiazolidinedione

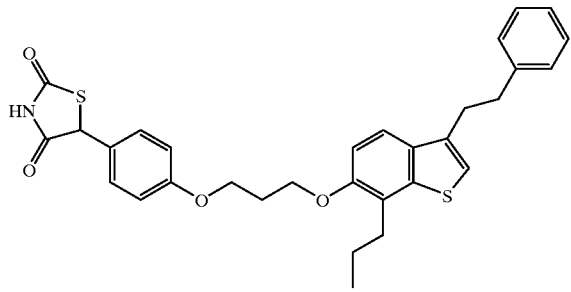

Step A: Preparation of 1-Diazo-4-phenyl-2-butanone.

A solution of hydrocinnamoyl chloride (10.00 grams; 100 mL dry diethyl ether) was carefully added to freshly prepared etherial diazomethane (85.6 grams Diazald; 100 mL dry ethyl ether) at 0° C. The reaction was held at 0° C. until outgassing subsided (15 minutes), then raised to room temperature (15 minutes). Acetic acid (5.0 mL) was added and the reaction partitioned (pH4 pthalate buffer and methyl tert-butyl ether). The organic was washed with water, dried over MgSO$_4$ and filtered to provide, upon evaporation, an oil containing the title compound. The crude product was used with no further purification or delay.

$^1$H NMR (400 MHz, CDCl$_3$): δ 7.32–7.18 (mult, 5H), 5.19 (vbrs, 1H), 3.04–2.92 (mult, 4H).

Step B: Preparation of 1-Bromo-4-phenyl-2-butanone.

A 0° C. solution of the crude product from Step A (12.89 grams; dry dichloromethane; 150 mL) was treated dropwise with 48% HBr (36.0 mL). When outgassing ceased, the solution was warmed to ambient temperature. After 15 minutes, the reaction was partitioned (isopropyl acetate and water), washed twice with water and dried (magnesium sulfate). Filtration and evaporation furnished the title compound as an oil which crystallized on standing, $^1$H NMR (400 MHz, CDCl$_3$): δ 7.30–7.16 (mult, 5H), 3.83 (s, 2H), 2.97–2.91 (mult, 4H).

Step C: Preparation of 1-(3-methoxyphenyl)thio-4-phenyl-2-butanone.

A dry, DMF (225 mL) solution of the Step B product (20.212 grams) was exposed to di-isopropylethyl amine (16.22 mL), then to 3-methoxythiophenol (11.424 grams). Stirring at ambient temperature for 6 hours was followed by partition (isopropyl acetate and pH4 pthalate buffer). The organic was washed twice with water, dried (magnesium sulfate) and filtered. Concentration and silica gel chromatography (5:1 hex/CH$_2$Cl$_2$) completed the isolation of the title compound.

$^1$H NMR (400 MHz, CDCl$_3$): δ 7.26–7.12 (mult, 6H), 6.83 (dd, 2H, J=4.7, 2.2 Hz), 6.73 (dd, 1H, J=8.3, 2.4 Hz), 3.76 (s, 3H), 3.63 (s, 2H), 2.88 (oct, 4H, J=5.8 Hz).

Step D: Preparation of 3-(2-Phenylethyl)-6-methoxybenzothiophene.

The product from Step C (8.495 grams), dissolved in dry CH$_2$Cl$_2$ (85 mL) was added dropwise to a 0° C. CH$_2$Cl$_2$ solution (34 mL) of methanesulfonic acid (17 mL). The reaction was kept at 0° C. for 20 minutes, then briefly warmed to ambient temperature. The reaction was rapidly poured into a vigorously stirred cold mixture of excess 5N NaOH and methyl tert-butyl ether. The organic was dried over magnesium sulfate and filtered. Concentration and chromatography over silica gel (5:1 hex/CH$_2$Cl$_2$) gave the title compound as a clear oil.

$^1$H NMR (400 MHz, CDCl$_3$): δ 7.66 (d, 1H, J=8.8 Hz), 7.37–7.20 (mult, 6H), 7.05 (dd, 1H, J=8.8, 2.4 Hz), 6.91 (t, 1H, J=0.9 Hz), 3.90 (s, 3H), 3.16–3.02 (mult, 4H).

Step E: Preparation of 3-(2-Phenylethyl)-6-hydroxybenzothiophene.

A stirred, –10° C. solution of the product from Step D (5.483 grams; dry methylene chloride; 60 mL) was treated with 1M boron tribromide solution (methylene chloride; 20.81 mL). After 2 hours, the reaction was momentarily warmed to ambient temperature. It was partitioned between isopropyl acetate and aqueous sodium bicarbonate, washed once with water and dried over magnesium sulfate. Filtration and evaporation produced a semi-solid. Chromatography over silica gel (2.5:1 hex/ethyl acetate) resulted in the isolation of the title compound, a pale yellow solid.

$^1$H NMR (400 MHz, CDCl$_3$): δ 7.60 (d, 1H, J=8.8 Hz), 7.35–7.23 (mult, 6H), 6.94 (dd, 1H, J=8.7, 2.3 Hz), 6.88 (s, 1H), 5.40 (s, 1H), 3.13–3.02 (mult, 4H).

Step F: Preparation of 3-(2-Phenylethyl)-6-allyloxybenzothiophene.

A stirred solution of the product from Step E (4.651 grams) in dry DMF (40 mL) was exposed to allyl bromide (1.66 mL) followed by cesium carbonate (6.26 grams). After 2.5 hours at ambient temperature, the reaction was partitioned between isopropyl acetate and pH4 pthalate buffer. The organic was washed twice with water, dried over magnesium sulfate and filtered. Evaporation gave a residue which, when chromatographed over silica gel (3:1 hex/CH$_2$Cl$_2$), gave the title compound, a clear oil.

$^1$H NMR (400 MHz, CDCl$_3$): δ 7.73 (d, 1H, J=8.8 Hz), 7.47–7.34 (mult, 6H), 7.19 (dd, 1H, J=8.8, 2.3 Hz), 6.99 (s, 1H), 6.22 (dquints, 1H, J=4.3 Hz), 5.62 (dquarts, 1H, J=17.3, 1.6 Hz), 5.44 (dquarts, 1H, J=10.5, 1.4 Hz), 4.69 (t, 1H, J=1.5 Hz), 4.67 (t, 1H, J=1.5 Hz), 3.25–3.12 (mult, 4H).

Step G: Preparation of 3-(2-Phenylethyl)-6-hydroxy-7-allyl-benzothiophene.

The product from Step F (4.373 grams), dissolved in 1,2-dichlorobenzene (45 mL) was refluxed under nitrogen for 8.5 hours. The solution was cooled to approx. 50° C. High vacuum was applied and the solvent removed until the residue solidified. The solid was dissolved in $CH_2Cl_2$ (100 mL), recovered, re-evaporated and chromatographed over silica gel ($CH_2Cl_2$). Evaporation of the appropriate fractions gave the title compound as a pale yellow solid.

$^1$H NMR (400 MHz, $CDCl_3$): δ 7.53 (d, 1H, J=8.5 Hz), 7.35–7.20 (mult, 5H), 6.95 (d, 1H, J=8.5 Hz), 6.93 (d, 1H, J=8.4 Hz), 6.06 (apparent dpent, 1H, J=7.1, 3.9 Hz), 5.23 (dquart, 1H, J=15.7, 1.7 Hz), 5.17 (dquart, 1H, J=11.5, 1.8 Hz), 5.09 (s, 1H), 3.67 (dt, 2H, J=6.3, 1.6 Hz), 3.13–3.01 (mult, 4H), 1.27 (t, 3H, J=7.2 Hz).

Step H: Preparation of 3-(2-Phenylethyl)-6-hydroxy-7-propyl-benzothiophene.

The product from Step G (3.062 grams) was dissolved in methyl tert-butyl ether (60 mL) and placed in a hydrogenation bottle. 5% Pd/C catalyst (306 mg) was added and the mixture hydrogenated for 1 hour using a Parr apparatus (14 psi). Filtration through Celite and evaporation gave the title compound as a yellow oil. On standing, a pale yellow solid was produced which required no additional purification.

$^1$H NMR (400 MHz, $CDCl_3$): δ 7.45 (d, 1H, J=8.5 Hz), 7.32–7.20 (mult, 6H), 6.89 (d, 1H, J=8.4 Hz), 5.28 (s, 1H), 3.10–3.01 (mult, 4H), 2.84 (dd, 2H, J=7.7, 1.6 Hz), 1.74 (hex, 2H, J=6.0 Hz), 1.02 (t, 3H, J=7.4).

Step I: Preparation of Methyl 4-[3-(3-(2-phenylethyl)-7-propyl-benzothiophen-6-yloxy)-1-propoxy]phenylacetate.

The title compound was prepared according to the method described in Example 1, Step B, using 3-(2-phenylethyl)-6-hydroxy-7-propylbenzothiophene as the starting material.

$^1$H NMR (400 MHz, $CDCl_3$): δ 7.50–7.42 (m, 4H), 7.31 (d, 2H, J=8.8 Hz), 7.19–7.16 (d, 2H, J=8.3 Hz), 6.92–6.83 (m, 3H), 6.46 (s, 1H), 4.21–4.16 (m, 4H), 3.67 (s, 3H), 3.54 (s, 2H), 2.95 (t, 2H, J=7.4 Hz), 2.29 (quint, 2H, J=6.3 Hz), 1.71 (hex, 2H, J=5.9 Hz), 1.01 (t, 3H, J=7.3 Hz).

Step J: Preparation of 5-[4-(3-(3-(2-phenylethyl)-7-propyl-benzothiophen-6-yloxy)-1-propoxy)]phenyl-2,4-thiazolidinedione The title compound was prepared according to the method described in Example 1, Step C, using methyl [4-(3-(7-propyl-3-(2-phenylethyl)benzothiophen-6-yloxy)-1-propoxy)]phenylacetate from Step I above as the starting material.

$^1$H NMR (400 MHz, $CDCl_3$): δ 9.46 (brs, 1H), 7.59 (d,1H, J=8.6 Hz), 7.38–7.24 (m, 4H), 7.09 (d,1H, J=8.8 Hz), 6.98 (d, 2H, J=8.8 Hz), 6.92–6.83 (m, 3H), 6.46 (s, 1H), 5.30 (s, 1H), 4.26 (bdquart, 4H, $J_{avg}$=5.5 Hz), 3.11 (vbdquint, 4H), 2.91 (bdd, 2H, J=7.4, 1.4 Hz), 2.34 (quint, 2H, J=6.0 Hz), 1.76 (hex, 2H, J=7.5 Hz), 1.03 (t, 3H, J=7.3 Hz).

EXAMPLE 64

5-[3-(4-(3-(2-phenylethyl)-7-propyl-benzothiophen-1,1-dioxide-6-yloxy)-1-butoxy)]phenyl-2,4-thiazolidinedione

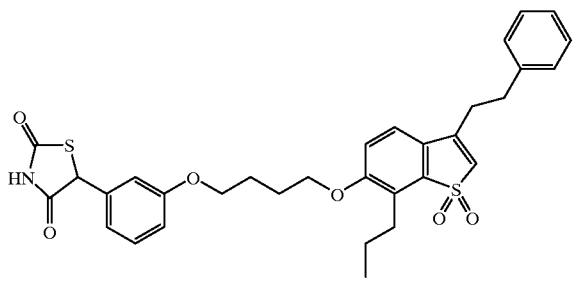

Step A: Preparation of 3-(2-Phenylethyl)-6-hydroxy-7-propyl-benzothiophene-1,1-dioxide.

The product of Example 63, Step H (3.515 grams) in $CH_2Cl_2$ solution (40 mL) was stirred (0° C.) and treated with solid 75% m-chloroperbenzoic acid (5.457 grams) in portions. After 15 minutes the reaction was warmed to ambient temperature and stirring continued for 1 hour. Partition between isopropyl acetate and aqueous sodium bicarbonate was followed by washing of the organic once with aqueous sodium bicarbonate, then water. Drying over magnesium sulfate, filtration and evaporation afforded a solid which was chromatographed over silica gel (5:1 hex/ethyl acetate). The title compound was acquired as a white solid.

$^1$H NMR (400 MHZ, $CDCl_3$): δ 7.35–7.19 (m, 4H), 7.04 (d, 1H, J=8.1 Hz), 6.89 (d, 1H, J=8.2 Hz), 6.63 (vbrs, 1H), 6.29 (t, 1H, J=1.5 Hz), 2.97–2.78 (m, 6H), 1.74 (dsex, 2H, J=7.2, 2.9 Hz), 1.03 (t, 3H, J=7.4 Hz).

Step B: Preparation of Methyl 3-(4-(7-propyl-3-(2-phenylethyl)-benzothiophen-1,1-dioxide-6-yloxy)-1-butoxy)phenylacetate.

The title compound was prepared according to the method described in Example 1, Step B, using 3-(2-phenylethyl)-6-hydroxy-7-propylbenzothiophene-1,1-dioxide (Step A above) as the starting material.

$^1$H NMR (400 MHz, $CDCl_3$): δ 7.50–7.42 (m, 4H), 7.31 (d,2H, J=8.8 Hz), 7.19–7.16 (d,2H, J=8.3 Hz), 6.92–6.83 (m, 3H), 6.46 (s, 1H), 4.21–4.16 (m, 4H), 3.67 (s, 3H), 3.54 (s, 2H), 2.95 (t, 2H, J=7.4 Hz), 2.29 (quint, 2H, J=6.3 Hz), 1.71 (hex, 2H, J=5.9 Hz), 1.01 (t, 3H, J=7.3 Hz).

Step C: Preparation of 5-[3-(4-(3-(2-phenylethyl)-7-propyl-benzothiophen-1,1-dioxide-6-yloxy)-1-butoxy)]phenyl-2,4-thiazolidinedione The title compound was prepared according to the method described in Example 1, Step C, using methyl 3-((4-(7-propyl-3-(2-phenylethyl)-benzothiophen-1,1-dioxide-6-yl) oxy)-1-butoxy)phenylacetate (Step B above) as the starting material.

$^1$H NMR (400 MHz, $CDCl_3$): δ 8.42 (brs, 1H), 7.32–7.19 (m, 6H), 7.12 (d, 1H, J=8.3 Hz), 6.98 (d, 1H, J=8.1 Hz), 6.91–6.85 (m, 4H), 6.30 (s, 1H), 5.30 (s, 1H), 4.04 (brquart, 4H, J=6.3 Hz), 2.94–2.88 (m, 4H), 2.02–1.98 (m, 4H), 1.69 (hex, 2H, J=5.2 Hz), 0.99 (t, 3H, J=7.3 Hz).

EXAMPLE 65

5-[4-(3-(7-propyl-3-(2-phenylethyl)-benzothiophen-1,1-dioxide-6-yloxy)-1-propoxy)]phenyl-2,4-thiazolidinedione

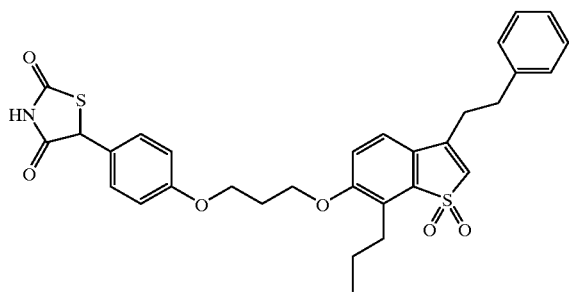

Step A: Preparation of Methyl 4-(3-(7-propyl-3-(2-phenylethyl)-benzothiophen-1,1-dioxide-6-yloxy)-1-propoxy)phenylacetate The title compound was prepared according to the method described in Example 1, Step B, using 3-(2-phenylethyl)-6-hydroxy-7-propylbenzothiophene-1,1-dioxide (Example 64, Step A) as the starting material.

$^1$H NMR (400 MHz, CDCl$_3$): δ 7.50–7.42 (m, 4H), 7.31 (d,2H, J=8.8 Hz), 7.19–7.16 (d,2H, J=8.3 Hz), 6.92–6.83 (m, 3H), 6.46 (s, 1H), 4.21–4.16 (m, 4H), 3.67 (s, 3H), 3.54 (s, 2H), 2.95 (t, 2H, J=7.4 Hz), 2.29 (quint, 2H, J=6.3 Hz), 1.71 (hex, 2H, J=5.9 Hz), 1.01 (t, 3H, J=7.3 Hz).

Step B: Preparation of 5-[4-(3-(3-(2-phenylethyl)-7-propyl-benzothiophen-1,1-dioxide-6-yloxy)-1-propoxy)]phenyl-2,4-thiazolidinedione The title compound was prepared via the method delineated in Example 1, Step C, using methyl 4-(3-(3-(2-phenylethyl)-7-propyl-benzothiophen-1,1-dioxide-6-yloxy)-1-propoxy)phenylacetate (Step A above) as the starting material.

$^1$H NMR (400 MHz, CDCl$_3$): δ 8.87 (brs, 1H), 7.32–7.24 (m, 6H), 7.21 (t, 2H, J=7.1 Hz), 7.12 (d, 1H, J=8.1 Hz), 6.90 (d, 2H, J=8.7 Hz), 6.89 (d, 1H, J=8.2 Hz), 6.30 (s, 1H), 5.31 (s, 1H), 4.16 (quart, 4H, J=5.9 Hz), 2.95–2.87 (m, 4H), 2.81 (t, 2H, J=7.7 Hz), 2.29 (quint, 2H, J=6.0 Hz), 1.67 (hex, 2H, J=7.7 Hz), 0.98 (t, 3H, J=7.4 Hz).

EXAMPLE 66

5-[3-(4-(3-(2-phenylethyl)-7-propyl-benzothiophen-1-oxide-6-yloxy)-1-butoxy)]phenyl-2,4-thiazolidinedione

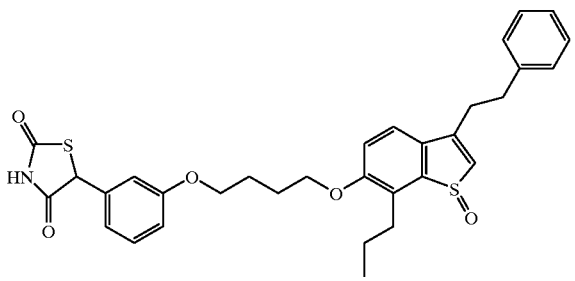

Step A: Preparation of 3-(2-Phenylethyl)-6-hydroxy-7-propyl-benzothiophene-1-oxide.

The product of Example 63, Step H (2.017 grams) in CH$_2$Cl$_2$ solution (40 mL) was stirred (0° C.) and treated with solid 75% m-chloroperbenzoic acid (1.567 grams) in portions. The reaction was warmed to ambient temperature after 15 minutes and stirred for 1.5 hours. Partition of the reaction between isopropyl acetate and aqueous sodium bicarbonate was followed by washing of the organic with aqueous sodium bicarbonate, then water. Drying over magnesium sulfate, filtration and evaporation afforded a solid which was chromatographed over silica gel (2 step gradient; 5:1 hex/ethyl acetate; 5:2 hex/ethyl acetate; 5:2:0.35 hex/ethyl acetate/methanol). The title compound was acquired as a white solid.

$^1$H NMR (400 MHZ, CDCl$_3$): δ 8.53 (brs, 1H), 7.33–7.18 (mult, 5H), 7.01 (d, 1H, J=8.2 Hz), 6.88 (d, 1H, J=8.2 Hz), 6.50 (s, 1H), 2.99–2.77 (mult, 4H), 1.67 (hex, 2H, J=7.6 Hz), 0.95 (t, 3H, J=6.7 Hz).

Step B: Preparation of Methyl 3-(4-(3-(2-phenylethyl)-7-propyl-benzothiophen-1-oxide-6-yloxy)-1-butoxy)phenylacetate The title compound was prepared by adherence to the method specified in Example 1, Step B, using 3-(2-phenylethyl)-6-hydroxy-7-propyl-benzothiophene-1-oxide (Step A above) as the starting material.

$^1$H NMR (400 MHz, CDCl$_3$): δ 7.50–7.42 (m, 4H), 7.31 (d,2H, J=8.8 Hz), 7.19–7.16 (d,2H, J=8.3 Hz), 6.92–6.83 (m, 3H), 6.46 (s, 1H), 4.21–4.16 (m, 4H), 3.67 (s, 3H), 3.54 (s, 2H), 2.95 (t, 2H, J=7.4 Hz), 2.29 (quint, 2H, J=6.3 Hz), 1.71 (hex, 2H, J=5.9 Hz), 1.01 (t, 3H, J=7.3 Hz).

Step B: Preparation of 5-[3-(4-(3-(2-phenylethyl)-7-propyl-benzothiophen-1-oxide-6-yloxy)-1-butoxy)]phenyl-2,4-thiazolidinedione The title compound was prepared according to the method described in Example 1, Step C, using methyl 3-(4-(3-(2-phenylethyl)-7-propyl-benzothiophen-1-oxide-6-yloxy)-1-butoxy)phenylacetate (Step B above) as the starting material.

$^1$H NMR (400 MHz, CDCl$_3$, diastereomeric pair): δ 9.62–9.53 (vbrs, 1H), 7.32–7.17 (m, 6H), 6.96–6.86 (m, 4H), 6.60 (s, 0.5H), 6.59 (s, 0.5H), 5.26 (s, 0.5H), 5.25 (s, 0.5H), 4.09–4.03 (m, 4H), 3.01–2.84 (m, 6H), 2.05–2.00 (m, 4H), 1.70 (bhex, 2H, J=8.5 Hz), 0.98 (t, 1.5H, J=7.4 Hz), 0.95 (t, 1.5H, J=7.3 Hz).

EXAMPLE 67

5-[4-(3-(3-(2,2-dimethylpropyl)-7-propyl-benzofuran-6-yloxy)-1-propoxy)]phenyl 2,4-thiazolidinedione

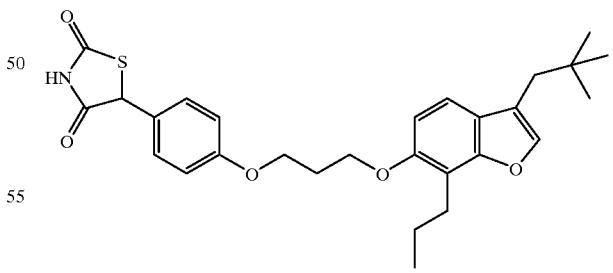

Step A: Preparation of 1-diazo-4,4-dimethyl-2-pentanone.

A solution of tert-butyl acetyl chloride (1.136 grams) in dry ethyl ether (10 mL) was slowly added to a 0° C. diethyl ether (20 mL) solution of freshly generated diazomethane (from 20 grams Diazald). After stirring for 30 minutes, the reaction was warmed to ambient temperature for another 30 minutes. Acetic acid (2 mL) was added and the reaction partitioned between methyl tert-butyl ether and water. The organic was washed once with water, dried over magnesium sulfate and filtered. Concentration afforded an oil containing the title compound which was immediately used with no further purification.

$^1$H NMR (400 MHZ, CDCl$_3$): δ 5.18 (brs, 1H), 2.15 (brs, 2H), 1.01 (s, 9H).

Step B: Preparation of 1-Bromo-4,4-dimethyl-2-pentanone.

To a stirred, −10° solution of the crude product from Step A (1.233 grams) in methylene chloride (12 mL) was added 48% HBr dropwise (1.14 mL). After gas evolution ceased, the reaction was stirred for 15 minutes at room temperature. The reaction was partitioned between isopropyl acetate and water. The organic was washed once with water, dried over magnesium sulfate and filtered. Evaporation afforded an oil containing the title compound which was used without further processing.

$^1$H NMR (400 MHZ, CDCl$_3$): δ 3.85 (s, 2H), 2.50 (s, 2H), 1.01 (s, 9H).

Step C: Preparation of 1-(3-methoxyphenoxy)-4,4-dimethyl-2-pentanone.

A stirred solution of the product from Step B (1.626 grams) in dry DMF (18 mL) was combined with 3-methoxyphenol (1.256 grams) and cesium carbonate (3.292 grams). The mixture was stirred for 2.5 hours. The reaction was partitioned between isopropyl acetate and pH4 pthalate buffer. The organic was washed twice with water, dried over magnesium sulfate and filtered. Concentration furnished an oil from which the title compound was isolated by chromatography over silica gel (4:1 hex/ethyl acetate).

$^1$H NMR (400 MHZ, CDCl$_3$): δ 7.18 (ddd, 1H, J=7.7, 6.9, 0.7 Hz), 4.47 (s, 2H), 3.78 (s, 3H), 2.44 (s, 2H), 1.05 (s, 9 Hz).

Step D: Preparation of 3-(2,2-dimethylpropyl)-6-methoxybenzofuran.

The product from Step C (1.408 grams), dissolved in dry methylene chloride (15 mL), was added to phosphorous oxychloride (30 mL). The reaction was stirred 2 hours at 40° C. The solution was twice diluted with xylenes (30 mL) and concentrated under high vacuum. The non-volatiles were partitioned between isopropyl acetate and aqueous sodium bicarbonate. The organic was re-washed with aqueous bicarbonate, dried over magnesium sulfate and filtered. Removal of solvents afforded a residue which was chromatographed over silica gel (3:1 hex/CH$_2$Cl$_2$), yielding the title compound.

$^1$H NMR (400 MHZ, CDCl$_3$): δ 7.40 (d, 1H, J=8.6 Hz), 7.31 (s, 1H), 7.00 (d, 1H, J=2.2 Hz), 6.88 (dd, 1H, J=8.6, 2.4 Hz), 3.85 (s, 3H), 2.52 (s, 2H), 0.98 (s, 9H).

Step E: Preparation of 3-(2,2-dimethylpropyl)-6-hydroxybenzofuran.

To a −10° C. solution of the product of Step D (2.379 grams) in dry methylene chloride (35 mL) was added 1M boron tribromide solution (CH$_2$Cl$_2$; 3.70 mL). Warming to ambient temperature was followed by stirring for 1 hour. The reaction was partitioned between isopropyl acetate and aqueous sodium bicarbonate. The organic was washed twice with water and dried over magnesium sulfate. Filtration and removal of volatiles provided a residue which was chromatographed over silica gel (5:1 hex/ethyl acetate), giving the title compound.

$^1$H NMR (400 MHZ, CDCl$_3$): δ 7.34 (d, 1H, J=8.4 Hz), 7.28 (s, 1H), 6.93 (d, 1H, J=2.2 Hz), 6.76 (dd, 1H, J=8.4, 2.2 Hz), 4.98 (s, 1H), 2.49 (s, 2H), 0.95 (s, 9H).

Step F: Preparation of 3-(2,2-dimethylpropyl)-6-allyloxybenzofuran.

A stirred solution of the product from Step E (2.880 grams) in dry DMF (30 mL) was treated with allyl bromide (1.282 mL) followed by cesium carbonate (4.828 grams). After 2 hours, the mixture was partitioned between isopropyl acetate and pH4 pthalate buffer. The organic was washed twice with water, dried over magnesium sulfate and filtered. Concentration gave the title compound in such purity that further processing was not required.

$^1$H NMR (400 MHZ, CDCl$_3$): δ 7.37 (d, 1H, J=8.6 Hz), 7.28 (s, 1H), 6.99 (d, 1H, J=2.2 Hz), 6.87 (dd, 1H, J=8.6, 2.2 Hz), 6.07 (mult, 1H), 5.43 (dquart, 1H, J=17.3, 1.6 Hz), 5.29 (dquart, 1H, J=10.5, 1.6 Hz), 4.56 (t, 1H, J=1.5 Hz), 4.55 (t, 1H, J=1.5 Hz), 2.49 (s, 2H), 0.95 (s, 9H).

Step G: Preparation of 3-(2,2-dimethylpropyl)-6-hydroxy-7-allyl benzofuran.

A solution prepared from 1,2-dichlorobenzene (65 mL) and the product of Step F (3.226 grams) was refluxed for 8 hours. The reaction, cooled to approx. 50° C., was subjected to high vacuum, removing the solvent by distillation. The remaining solid was digested in refluxing cyclohexane, cooled to ambient and filtered. The mother liquor was evaporated and chromatographed over silica gel (2.5:1 hex/ethyl acetate), producing more solid which was added to the previous, providing all the available title compound.

$^1$H NMR (400 MHZ, CDCl$_3$): δ 7.32 (s, 1H), 7.26 (d, 1H, J=8.3 Hz), 6.80 (d, 1H, J=8.4 Hz), 6.09 (tquart, 1H, J=13.3, 1.0 Hz), 5.26 (quart, 1H, J=1.7 Hz), 5.20 (hex, 1H, J=2.5 Hz), 5.16 (quart, 1H, J=1.5 Hz), 3.72 (t, 1H, J=1.5 Hz), 3.70 (t, 1H, J=1.5 Hz), 2.51 (s, 2H), 0.98 (s, 9H).

Step H: Preparation of 3-(2,2-dimethylpropyl)-6-hydroxy-7-propyl benzofuran.

A solution of the product from Step G (1.912 grams) in methyl tert-butyl ether (20 mL) was combined with 5% Pd/C catalyst (200 mg) in a hydrogenation bottle. The mixture was hydrogenated using a Parr apparatus at 14 psi for 1 hour. The catalyst was removed by filtration through Celite and the filtrate evaporated. The resultant solid was employed without further purification.

$^1$H NMR (400 MHZ, CDCl$_3$): δ 7.28 (s, 1H), 7.17 (d, 1H, J=8.3 Hz), 6.72 (d, 1H, J=8.4 Hz), 4.82 (s, 1H), 2.83 (t, 2H, J=7.7 Hz), 2.48 (s, 2H), 1.70 (hex, 2H, J=9.2 Hz), 0.99 (t, 3H, J=7.5 Hz), 0.95 (s, 9H).

Step I: Preparation of Methyl 4-(3-(3-(2,2-dimethylpropyl)-7-propyl-benzofuran-6-yloxy)-1-propoxy)phenylacetate.

The title compound was prepared according to the method described in Example 1, Step B, using 3-(2,2-dimethyl-1-propyl)-6-hydroxy-7-propyl benzofuran (Step H above) as the starting material.

$^1$H NMR (400 MHz, CDCl$_3$): δ 7.50–7.42 (m, 4H), 7.31 (d, 2H, J=8.8 Hz), 7.19–7.16 (d, 2H, J=8.3 Hz), 6.92–6.83 (m, 3H), 6.46 (s, 1H), 4.21–4.16 (m, 4H), 3.67 (s, 3H), 3.54 (s, 2H), 2.95 (t, 2H, J=7.4 Hz), 2.29 (quint, 2H, J=6.3 Hz), 1.71 (hex, 2H, J=5.9 Hz), 1.01 (t, 3H, J=7.3 Hz).

Step J: Preparation of 5-[4-(3-(3-(2,2-dimethylpropyl)-7-propyl-benzofuran-6-yloxy)-1-propoxy)]phenyl-2,4-thiazolidinedione The title compound was prepared according to the method described in Example 1, Step C, using methyl 4-(3-(3-(2,2-dimethyl-1-propyl)-7-propyl-benzofuran-6-yloxy)-1-propoxy)phenylacetate as the starting material.

$^1$H NMR (400 MHz, CDCl$_3$): δ 8.43 (brs, 1H), 7.32–7.23 (m, 5H), 6.92 (d,2H, J=8.8 Hz), 6.84 (d, 1H, J=8.6 Hz), 5.32 (s, 1H), 4.19 (apparent quart, 4H, J$_{avg}$=6.0 Hz), 2.82 (dd, 2H, J=7.6, 1.5 Hz), 2.27 (quint, 2H, J=6.1 Hz), 1.64 (hex, 2H, J=7.3 Hz), 0.94 (s, 9H), 0.92 (t, 3H, J=7.4 Hz).

EXAMPLE 68

5-[3-(4-(3-(2,2-dimethylpropyl)-7-propyl-benzofuran-6-yloxy)-1-butoxy)]phenyl-2,4-thiazolidinedione

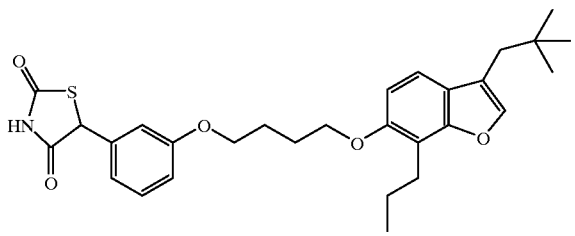

Step A: Preparation of Methyl 3-(4-(3-(2,2-dimethylpropyl)-7-propyl-benzofuran-6-yloxy)-1-butoxy)phenylacetate.

The title compound was prepared according to the method described in Example 1, Step B, using 3-(2,2-dimethyl-1-propyl)-6-hydroxy-7-propyl benzofuran (Example 67, Step H) as the starting material.

$^1$H NMR (400 MHz, CDCl$_3$): δ 7.50–7.42 (m, 4H), 7.31 (d,2H, J=8.8 Hz), 7.19–7.16 (d,2H, J=8.3 Hz), 6.92–6.83 (m, 3H), 6.46 (s, 1H), 4.21–4.16 (m, 4H), 3.67 (s, 3H), 3.54 (s, 2H), 2.95 (t, 2H, J=7.4 Hz), 2.29 (quint, 2H, J=6.3 Hz), 1.71 (hex, 2H, J=5.9 Hz), 1.01 (t, 3H, J=7.3 Hz).

Step B: Preparation of 5-[3-(4-(3-(2,2-dimethylpropyl)-7-propyl-benzofuran-6-yloxy)-1-butoxy)]phenyl-2,4-thiazolidinedione The title compound was prepared according to the method described in Example 1, Step C, using methyl 3-(4-(7-propyl-3-(2,2-dimethyl-1-propyl)benzofuran-6-yloxy)-1-butoxy)phenylacetate (Step A above) as the starting material.

$^1$H NMR (400 MHz, CDCl$_3$): δ 9.41 (brs, 1H), 7.31–7.24 (m, 3H), 6.90 (dd, 1H, J=8.3, 1.8 Hz), 6.85 (d, 1H, J=8.6 Hz), 5.27 (s, 1H), 4.08–4.04 (m, 4H), 2.87 (dd, 2H, J=7.5, 1.4 Hz), 2.50 (s, 2H), 2.00 (m, 4H), 1.69 (hex, 2H, J=7.5 Hz), 0.97 (s, 9H), 0.95 (t, 3H, J=7.4 Hz),

EXAMPLE 69

5-[3-(4-(3-(2-phenylethyl)-7-propyl-benzofuran-6-yloxy)-1-butoxy)]phenyl-2,4-thiazolidinedione

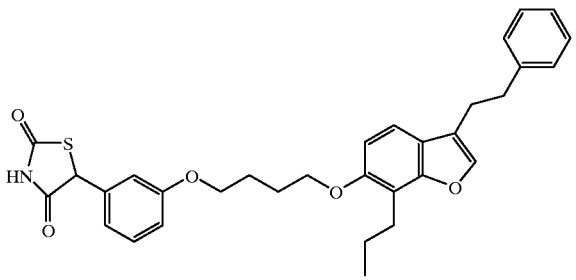

Step A: Preparation of 1-(3-methoxyphenoxyl)-4-phenyl-2-butanone.

A dry, DMF (80 mL) solution of the product of Example 63, Step B (5.519 grams) was exposed to 3-methoxyphenol (3.608 grams) followed by cesium carbonate (9.481 grams). After stirring at ambient temperature for 2 hours the reaction was partitioned between isopropyl acetate and pH4 pthalate buffer. The organic was washed twice with water, dried (magnesium sulfate) and filtered. Concentration and silica gel chromatography (5:1 hex/ethyl acetate) completed the isolation of the title compound, a yellow solid.

$^1$H NMR (400 MHz, CDCl$_3$): δ 7.29–7.14 (mult, 6H), 6.54 (dd, 1H, J=8.3, 2.3 Hz), 6.42 (t, 1H, J=2.4 Hz), 6.39 (dd, 1H, J=8.1, 2.5 Hz), 4.49 (s, 2H), 3.76 (s, 3H), 2.93 (s, 2H), overlapping a dt, 1H), 2.70 (dt, 1H, J=7.9, 10.5 Hz).

Step B: Preparation of 3-(2-Phenylethyl)-6-methoxy-benzofuran.

The product from Step A (2.368 grams), dissolved in dry CH$_2$Cl$_2$ (25 mL) was added dropwise to a -10° C. CH$_2$Cl$_2$ solution (10 mL) of methanesulfonic acid (5.68 mL). The reaction was warmed to ambient temperature and stirred for 30 minutes. The reaction was rapidly poured into a vigorously stirred cold mixture of excess 5N NaOH and methyl tert-butyl ether. The organic was dried over magnesium sulfate and filtered. Concentration and chromatography over silica gel (step gradient; 4:1 hex/CH$_2$Cl$_2$ to 1:1 hex/CH$_2$Cl$_2$) gave the title compound as a clear oil.

$^1$H NMR (400 MHz, CDCl$_3$): δ 7.36 (d, 1H, J=8.5 Hz), 7.31–7.19 (mult, 6H), 7.00 (d, 1H, J=2.2 Hz), 6.87 (dd, 1H, J=8.5, 2.2 Hz), 3.84 (s, 3H), 3.02–2.91 (mult, 4H).

Step C: Preparation of 3-(2-Phenylethyl)-6-hydroxy-benzofuran.

A stirred, -10° C. solution of the product from Step B (2.066 grams; dry methylene chloride; 20 mL) was treated with 1M boron tribromide solution (methylene chloride; 8.40 mL). After 15 minutes, the reaction was warmed to ambient temperature and stirred another 15 minutes. It was partitioned between isopropyl acetate and pH7 phosphate buffer, then washed twice more with pH7 buffer and dried over magnesium sulfate. Filtration and evaporation produced an oil which was chromatographed over silica gel (step gradient; CH$_2$Cl$_2$ to 40:1 CH$_2$Cl$_2$/ethyl acetate). The title compound was isolated as a pale yellow solid.

$^1$H NMR (400 MHz, CDCl$_3$): δ 7.32 (d, 1H, J=8.4 Hz), 7.30–7.19 (mult, 6H), 6.93 (d, 1H, J=2.2 Hz), 6.76 (dd, 1H, J=8.4, 2.2 Hz), 4.88 (vbrs, 1H), 3.01–2.90 (mult, 4H).

Step D: Preparation of 3-(2-Phenylethyl)-6-allyloxy-benzofuran.

A stirred solution of the product from Step C (1.128 grams) in dry DMF (15 mL) was exposed to allyl bromide (0.43 mL) followed by cesium carbonate (1.620 grams). After stirring overnight at ambient temperature, the reaction was partitioned between isopropyl acetate and pH4 pthalate buffer. The organic was washed twice with water, dried over magnesium sulfate and filtered. Evaporation gave the title compound, which did not require further purification.

$^1$H NMR (400 MHz, CDCl$_3$): δ 7.36 (d, 1H, J=8.6 Hz), 7.30–7.18 (multi, 6H), 7.00 (d, 1H, J=2.2 Hz), 6.89 (dd, 1H, J=8.6, 2.3 Hz), 6.13–6.03 (multi, 1H), 5.43 (dquarts, 1H, J=17.3, 1.6 Hz), 5.30 (dquarts, 1H, J=10.5, 1.4 Hz), 4.57 (t, 1H, J=1.5 Hz), 4.56 (t, 1H, J=1.5 Hz), 3.01–2.91 (multi, 4H).

Step E: Preparation of 3-(2-Phenylethyl)-6-hydroxy-7-allyl-benzofuran.

The product from Step D (1.245 grams), dissolved in 1,2-dichlorobenzene (20 mL) was refluxed under nitrogen for 11 hours. The solution was cooled to approx. 50° C. High vacuum was applied and the solvent removed until the residue solidified. The solid was dissolved in CH$_2$Cl$_2$ (100 mL), recovered, re-evaporated and chromatographed over silica gel (5:1 hex/ethyl acetate). Evaporation of the appropriate fractions gave the title compound as a pale yellow solid.

$^1$H NMR (400 MHz, CDCl$_3$): δ 7.35–7.19 (mult, 7H), 6.82 (d, 1H, J=8.2 Hz), 6.12 (multi, 1H), 5.25–5.14 (overlapping dquarts, 2H; downfield J's=17.2, 1.7 Hz; upfield J's=10.1, 1.6 Hz), 3.73 (t, 1H, J=1.6 Hz), 3.70 (t, 1H, J=1.6 Hz), 3.06–2.92 (multi, 4H).

Step F: Preparation of 3-(2-Phenylethyl)-6-hydroxy-7-propyl-benzofuran.

The product from Step E (1.116 grams) was dissolved in methyl tert-butyl ether (12 mL) and placed in a hydrogenation bottle. 5% Pd/C catalyst (110 mg) was added and the mixture hydrogenated for 0.5 hour using a Parr apparatus (14 psi). Filtration through Celite and evaporation gave the title compound as a yellow oil. On standing, a pale yellow solid formed which required no additional purification.

$^1$H NMR (400 MHz, CDCl$_3$): δ 7.36–7.22 (multi, 7H), 6.78 (d, 1H, J=8.3 Hz), 5.17 (s, 1H), 3.06–2.95 (multi, 4H), 2.91 (t, 2H, J=7.6 Hz), 1.79 (hex, 2H, J=6.0 Hz), 1.04 (t, 3H, J=7.3 Hz).

Step G: Preparation of Methyl 3-(4-(3-(2-phenylethyl)-7-propyl-benzofuran-6-yloxy)-1-butoxy)phenylacetate.

The title compound was prepared according to the method described in Example 1, Step B, using 3-(2-phenylethyl)-6-hydroxy-7-propyl benzofuran (Step F above) as the starting material.

$^1$H NMR (400 MHz, CDCl$_3$): δ 7.50–7.42 (m, 4H), 7.31 (d,2H, J=8.8 Hz), 7.19–7.16 (d,2H, J=8.3 Hz), 6.92–6.83 (m, 3H), 6.46 (s, 1H), 4.21–4.16 (m, 4H), 3.67 (s, 3H), 3.54 (s, 2H), 2.95 (t, 2H, J=7.4 Hz), 2.29 (quint, 2H, J=6.3 Hz), 1.71 (hex, 2H, J=5.9 Hz), 1.01 (t, 3H, J=7.3 Hz).

Step H: Preparation of 5-[3-(4-(3-(2-phenylethyl)-7-propyl-benzofiuran-6-yloxy)-1-butoxy)]phenyl-2,4-thiazolidinedione The title compound was prepared according to the method described in Example 1, Step C, using methyl 3-(4-(3-(2-phenylethyl)-7-propyl-benzofuran-6-yloxy)-1-butoxy) phenylacetate (Step G above) as the starting material.

$^1$H NMR (400 MHz, CDCl$_3$): δ 8.67 (brs, 1H), 7.32–7.18 (m, 4H), 6.90 (dd, 1H, J=8.3, 2.5 Hz), 6.85 (d, 1H, J=8.5 Hz), 5.29 (s, 1H), 4.14–4.04 (m, 4H), 2.96 (m, 4H), 2.85 (t, 2H, J=7.6 Hz), 2.00 (bm, 4H), 1.67 (hex, 2H, J=5.6 Hz), 0.94 (t, 3H, J=7.4 Hz).

EXAMPLE 70

5-[3-(4-(3-(2-phenylethyl)-7-propyl-benzothiophen-6-yloxy)-1-butoxy)]phenyl-2,4-thiazolidinedione

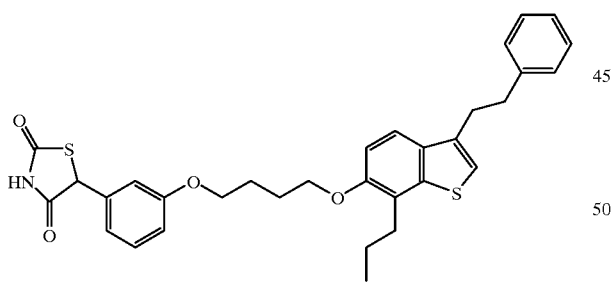

Step A: Preparation of Methyl 3-(4-(3-(2-phenylethyl)-7-propyl-benzothiophen-6-yloxy)-1-butoxy)phenylacetate The title compound was obtained by utilizing the method described in Example 1, Step B and using 3-(2-phenylethyl)-6-hydroxy-7-propylbenzothiophene (Example 63; Step H) as the starting material.

$^1$H NMR (400 MHz, CDCl$_3$): δ 7.57 (d, 1H, J=8.7 Hz), 7.34 (t, 2H, J=7.3 Hz), 7.28–7.24 (multi, 4H), 7.06 (d, 1H, J=8.7 Hz), 6.92–6.84 (multi, 4H), 4.14 (brt, 2H, J=5.2 Hz), 4.08 (brt, 2H, J=5.5 Hz), 3.71 (s, 3H), 3.62 (s, 2H), 3.13–3.06 (multi, 4H), 2.91 (dd, 2H, J=9.2, 7.6 Hz), 2.05 (brpent, 4H, J=2.7 Hz), 1.77 (hex, 2H, J=7.5 Hz), 1.04 (t, 3H, J=7.4 Hz).

Step B: Preparation of 5-[3-(4-(3-(2-phenylethyl)-7-propyl-benzothiophen-6-yloxy)-1-butoxy)]phenyl-2,4-thiazolidinedione The title compound was prepared using the method described in Example 1, Step C and employing methyl 3-(4-(3-(2-phenylethyl)-7-propyl-benzothiophen-6-yloxy)-1-butoxy)phenylacetate (Step A above) as the starting material.

$^1$H NMR (400 MHz, CDCl$_3$): δ 9.41 (brs, 1H), 7.56 (d, 1H, J=8.8 Hz), 7.35–7.20 (multi, 6H), 7.05 (d, 1H, J=8.8 Hz), 6.99–6.85 (multi, 4H), 5.26 (brs, 1H), 4.12 (brs, 2H), 4.07 (brs, 2H), 3.08 (brquart, 4H), 2.90 (brt, 2H, J=7.5 Hz), 2.04 (brs, 4H), 1.76 (brhex, 2H, J=7.6 Hz), 1.02 (t, 3H, J=7.3 Hz).

EXAMPLE 71

5-[4-(3-(3-(2-phenylethyl)-7-propyl-benzothiophen-1-oxide-6-yloxy)-1-propoxy)]phenyl-2,4-thiazolidinedione

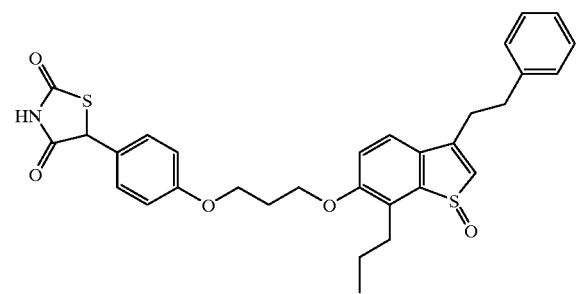

The title compound was prepared by the method described in Example 66, Step A using 5-[3-(4-(3-(2-phenylethyl)-7-propyl-benzothiophen-6-yloxy)-1-butoxy)] phenyl-2,4-thiazolidinedione as the starting material.

$^1$H NMR (400 MHz, CDCl$_3$, diastereomeric pair): δ 8.83 (brs, 1H), 7.36–7.32 (multi, 4H), 7.28–7.20 (multi, 4H), 6.99–6.93 (multi, 3H), 6.64 (d, 1H, J=1.4 Hz), 5.34 (s, 1H), 4.21 (brt, 4H, J=5.9 Hz), 3.07–2.92 (multi, 4H), 2.87 (bit, 2H, J=7.6 Hz), 2.33 (pent, 2H, J=5.8 Hz), 1.70 (brhex, 2H, J=7.8 Hz), 1.01 (dt, 3H, J=7.3, 1.7 Hz).

EXAMPLE 72

5-[4-(3-(2-propyl-4-(4'-fluorophenoxy)phenoxy) propoxy)phenyl]-2,4-thiazolidinedione

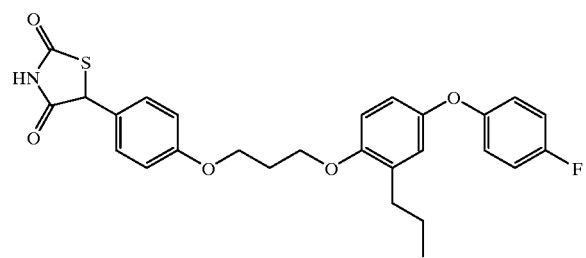

Step A: Preparation of 5-[4-(3-(2-propyl-4-(4'-fluorophenoxy)phenoxy)propoxy)phenyl]-2,4-thiazolidinedione This compound was prepared using the procedure described in Example 22, Step C, using 2-propyl-4-(4'-fluorophenoxy)phenol (as prepared in Example 23, Step A using 4-flourophenol); followed by the procedure described in Example 23, Step D.

$^1$H NMR (400 MHz, CDCl$_3$): δ 7.98 (broad s, 1H), 7.32 (d, 2H, J=8.66 Hz), 6.9 (m, 6H), 6.76 (m, 3H), 5.37 (s, 1H), 4.17 (t, 2H, J=4.14 Hz), 4.09 (t, 2H, J=5.94 Hz), 2.52 (q, 2H, 7.5 Hz), 2.26 (t, 2H, J=6.02 Hz), 1.54 (m, 2H, 7.5 Hz), 0.88 (t, 3H, J=7.32 Hz).

EXAMPLE 73

5-[4-(3-(2-propyl-4-(4'-tolylsulfonamidophenoxy)phenoxy)propoxy)phenyl]-2,4-thiazolidinedione

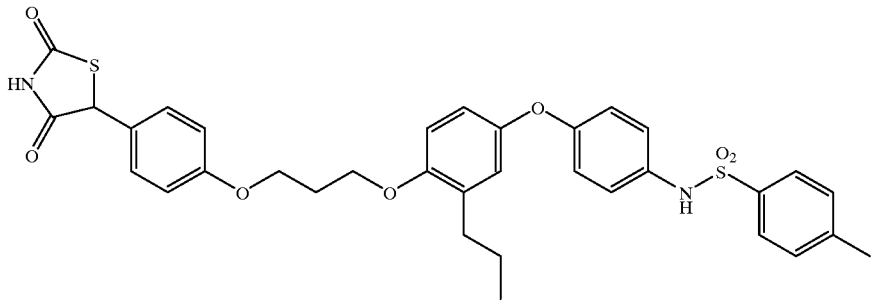

Step A: Preparation of 2-propyl-4-(4'-tolylsulfonamidophenoxy)phenol

A solution of 4-allyloxyphenol (as prepared in Example 22, Step A, first paragraph) (5.0 g, 33.3 mmol), 4-fluoro-1-nitrobenzene (5.17 g, 36.6 mmol), potassium carbonate 6.9 g, 49.9 mmol) and dimethylacetamide (20 mL) was heated to reflux over night. The reaction mixture was partitioned between ethyl acetate and water. The organic layer was dried (sodium sulfate) and concentrated. The residue was then chromatographed on silica gel using methylene chloride and hexane (20% to 50%) to yield the desired product as a yellow oil (7.3 g).

The yellow oil (7.3 g) was taken up in dichlorobenzene (30 mL) and refluxed over night. The reaction solution was concentrated to a black oil and chromatographed on silica gel using 10% acetone/hexane to yield an orange oil (4.9 g).

The orange oil (1 g, 3.68 mmol) was dissolved in DMF (5 mL) containing imidazole (626 mg, 9.2 mmol). Added to this t-butyldimethylchlorosilane (468 mg, 4.42 mmol) and the reaction was stirred for 4 hours. The reaction solution was then partitioned between ethyl acetate and water. The organic layer was separated, dried (sodium sulfate) and concentrated to give a yellow oil (~1.5 g). This oil was then dissolved in ethyl acetate (10 mL) and 10% palladium on carbon (250 mg) was added and the reaction mixture was stirred under a hydrogen atmosphere for 45 minutes. The reaction mixture was then filtered through celite and the filtrate concentrated to give an orange oil (1.42 g).

The orange oil (700 mg, 1.96 mmol) was taken up in methylene chloride (5 mL) and pyridine (0.4 mL, 4.9 mmol). To this solution was added tosyl chloride (448 mg, 2.35 mmol) and nn-dimethylaminopyridine (10 mg), and the reaction was stirred overnight. The reaction was then partitioned between ethyl acetate and water. The organic layer was then seperated, dried (sodium sulfate) and concentrated to give an orange oil (800 mg). This oil was then taken up in THF (5 mL) and cooled to 0° C. To this solution was added t-butylamonium fluoride and the reaction was stirred for 2 hours. The reaction was partitioned between ethyl acetate and water. The organic layer was then separated, dried (sodium sulfate) and concentrated to give an orange oil (440 mg).

$^1$H NMR (400 MHz, CDCl$_3$): δ 7.37 (d, 2H); 6.92 (d, 2H); 6.85 (m, 3H); 6.79 (bs, 2H); 4.71 (bs, 1H); 3.04 (s, 3H); 2.57 (t, 2H); 1.65 (m, 2H); 0.97 (t, 3H).

Step B: Preparation of Ethyl 4-(3-(2-propyl-4-(4'-tolylsulfonamido-phenoxy)phenoxy)propoxy)mandelate The title compound was prepared according to the method described in Example 22, Step C using 2-propyl-4-(4'-tolylsulfonamido-phenoxy)phenol (19.0 g, 62.0 mmol) and ethyl 4-(3-bromopropoxy)mandelate (19.5 g, 58.9 mmol) (as prepared in Example 22, Step B) as the starting materials.

Step C: Preparation of Ethyl α-chloro-4-(3-(2-propyl-4-(4'-tolylsulfonamido phenoxy)phenoxy)propoxy)phenylacetate The title compound was prepared according to the method described in Example 22, Step D, using ethyl 4-(3-(2-propyl-4-(4'-tolylsulfonamido phenoxy)phenoxy)propoxy) mandelate (16.8 g, 30.18 mmol) as the starting material.

$^1$H NMR (400 MHz, CDCl$_3$): δ 7.37 (d, 2H); 7.23 (m, 6H); 6.91 (d, 2H); 6.82 (m, 3H); 6.73 (bs, 2H); 5.27 (bs, 1H); 4.73 (bs, 1H); 4.2 (m, 2H); 3.93 (t, 2H); 3.84 (t, 2H); 2.85 (s, 3H); 2.57 (t, 2H); 1.93 (m, 2H); 1.63 (m, 2H); 1.05 (t, 3H); 0.95 (t, 3H).

Step D: Preparation of 5-[4-(3-(2-propyl-4-(4'-tolylsulfonamidophenoxy)phenoxy)propoxy)phenyl]-2,4-thiazolidinedione The title compound was prepared according to the method described in Example 1, Step C (second paragraph), using ethyl α-chloro-4-(3-(2-propyl-4-(4'-tolylsulfonamidophenoxy)phenoxy)propoxy) phenylacetate as the starting material.

$^1$H NMR (400 MHz, CDCl$_3$): δ 8.06 (bs, 1H); 7.29 (d, 2H); 7.23 (m, 6H); 6.89 (m, 2H); 6.85 (m, 3H); 6.72 (bs, 2H); 5.3 (s, 1H); 4.67 (bs, 1H); 4.01 (t, 2H); 3.84 (t, 2H); 2.88 (s, 3H); 2.57 (t, 2H); 1.98 (m, 2H); 1.63 (m, 2H); 0.97 (t, 3H).

EXAMPLE 74

5-[4-(3-(2-propyl-4-pyrazinyloxyphenoxy)propoxy)phenyl]-2,4-thiazolidinedione

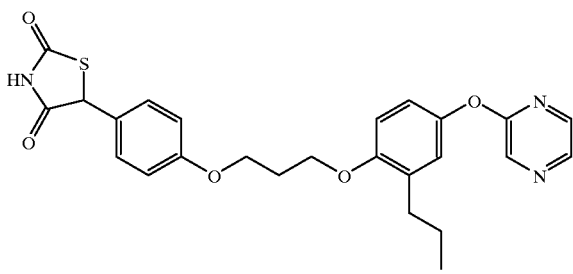

Step A: Preparation of 2-propyl-4-pyrazinyloxyphenol

The title compound was prepared according to the method described in Example 73, Step A substituting chloropyrazine for 4-fluoronitrobenzene as the starting material.

$^1$H NMR (400 MHz, CDCl$_3$): δ 8.36 (s, 1H); 8.21 (s, 1H); 8.1 (d, 1H); 6.90 (d, 1H); 6.82 (m, 1H); 6.74 (d, 1H); 5.67 (bs, 1H); 2.55 (t, 2H); 1.59 (m, 2H); 0.95 (t, 3H).

Step B: Preparation of Ethyl 4-(3-(2-propyl-4-pyrazinyloxyphenoxy)propoxy)mandelate The title compound was prepared according to the method described in Example 22, Step C using 2-propyl-4-pyrazinyloxyphenol (19.0 g, 62.0 mmol) and ethyl 4-(3-bromopropoxy)mandelate (19.5 g, 58.9 mnol) (as prepared in Example 22, Step C) as the starting materials.

Step C: Preparation of Ethyl α-chloro-4-(3-(2-propyl-4-pyrazinyloxyphenoxy)propoxy) phenylacetate The title compound was prepared according to the method described in Example 22, Step D, using ethyl 4-(3-(2-propyl-4-pyrazinyloxyphenoxy)propoxy)mandelate (16.8 g, 30.18 mmol) as the starting material.

Step D: Preparation of 5-[4-(3-(2-propyl-4-pyrazinyloxyphenoxy)propoxy)phenyl]-2,4-thiazolidinedione The title compound was prepared according to the method described in Example 1, Step C (second paragraph), using ethyl α-chloro-4-(3-(2-propyl-4-pyrazinyloxyphenoxy) propoxy) phenylacetate as the starting material.

$^1$H NMR (400 MHz, CDCl$_3$): δ 8.35 (s, 1H); 8.20 (s, 1H); 8.07 (d, 1H); 7.95 (bs, 1H); 7.32 (d, 2H); 6.93 (m, 3H); 6.85 (m, 2H); 5.32 (s, 1H); 4.17 (m, 4H); 2.55 (t, 2H); 2.26 (m, 2H); 1.57 (m, 2H); 0.90 (t, 3H).

EXAMPLE 75

5-[3-(3-(2-cyclopropylmethyl-4-phenoxy)propoxy)phenyl]-2,4-thiazolidinedione

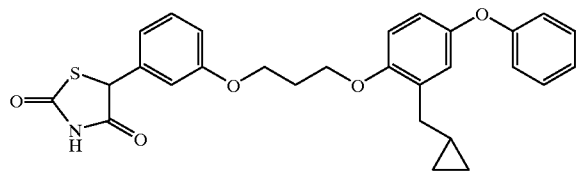

Step A: Preparation of 2-cyclopropymethyl-4-phenoxyphenol

To a solution of 2-allyloxy-4-phenoxyphenol (PCT Application WO97/28115) (1.0 g, 4.45 mmol) in ethyl ether cooled to 0° C. was added the diazomethane (20 mL of a 0.70M soln. in Et$_2$ O) under nitrogen. After 5 min of stirring, palladium acetate (cat., 2 mg) was added. After 10 min, an additional ammount of diazomethane (6 mL of a 0.70M soln. in Et$_2$ O). The reaction was stirred for 30 min at ambient temperature. The reaction mixture was filtered through a pad of celite, and the ether was evaporated in vacuo. The residue was purified on a silica gel flash chromatography column eluted with 10% EtOAc:hexane. Evaporation of the purified fractions and solvent removal in vacuo afforded the title compound.

$^1$H NMR (400 MHz, CDCl$_3$): δ 7.32–6.77 (ar, 8H), 4.82 (s, 1H), 2.53 (d, 2H, J=6.65 Hz), 0.55 (m, 2H).

Step B: Preparation of 5-[3-(3-(2-cyclopropylmethyl-4-phenoxy)propoxy)phenyl]-2,4-thiazolidinedione Using methyl 3-(3-bromopropoxy) mandelate and 2-cyclopropymethyl-4-phenoxyphenol (as prepared in Step A) as the starting materials for Example 22, Step B; the title compound was prepared according to the methods described in Example 22, Steps B through D.

$^1$H NMR (400 MHz, CDCl$_3$): δ 7.35–6.83 (ar, 12H), 5.33 (s, 1H), 4.16 (m, 4H), 2.52 (d, 2H, J=6.87 Hz), 2.27 (quint, 2H, J=6.04 Hz), 0.47 (m, 2H), 0.12 (m, 2H).

What is claimed is:

1. A method of treating, controlling or preventing one or more diseases, disorders, or conditions selected from the group consisting of diabetes mellitus, hyperglycemia, obesity, hyperlipidemia, hypertriglyceridemia, hypercholesterolemia, atherosclerosis, vascular restenosis, irritable bowel syndrome, pancreatitis, abdominal obesity, adipose cell tumors, adipose cell carcinomas, Syndrome X, polycystic ovarian syndrome, and other disorders where insulin resistance is a component, said method comprising the administration of an effective amount of a compound having Formula I, defined below, and an effective amount of a second compound selected from the group consisting of insulin sensitizers, PPARγ agonists, glitazones, troglitazone, pioglitazone, englitazone, MCC-555, BRL49653, biguanides, metformin, phenformin, insulin, insulin mimetics, sulfonylureas, tolbutamide, glipizide, α-glucosidase inhibitors, acarbose, cholesterol lowering agents, HMG-CoA reductase inhibitors, lovastatin, simvastatin, pravastatin, fluvastatin, atorvastatin, rivastatin, other statins, sequestrants, cholestyramine, colestipol, dialkylaminoalkyl derivatives of a cross-linked dextran, nicotinyl alcohol, nicotinic acid, a nicotinic acid salt, PPARα agonists, fenofibric acid derivatives, gemfibrozil, clofibrate, fenofibrate, benzafibrate, inhibitors of cholesterol absorption, beta-sitosterol, acyl CoA:cholesterol acyltransferase inhibitors, melinamide, probucol, PPARδ agonists, antiobesity compounds, fenfluramine, dexfenfluramine, phentiramine, sulbitramine, orlistat, neuropeptide Y5 inhibitors, β$_3$ adrenergic receptor agonists, and ileal bile acid transporter inhibitors, wherein the compound of Formula I is defined as follows:

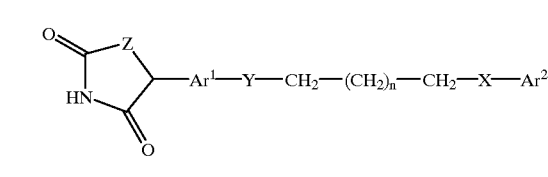

I wherein
Ar$^1$ is (1) arylene or
(2) heteroarylene,
  wherein arylene and heteroarylene are optionally substituted with from 1 to 4 groups selected from R$^a$;
Ar$^2$ is (1) ortho-substituted aryl or (2) ortho-substituted heteroaryl,
wherein said ortho substituent is selected from R; and aryl and heteroaryl are optionally further substituted with from 1–4 groups independently selected from $R^a$;

X and Y are independently O, S, N—$R^b$, or $CH_2$;

Z is O or S;

n is 0 to 3;

R is (1) $C_{3-10}$alkyl optionally substituted with 1–4 groups selected from halo and $C_{3-6}$cycloalkyl,
(2) $C_{3-10}$alkenyl, or
(3) $C_{3-8}$cycloalkyl;

$R^a$ is (1) $C_{1-15}$ alkanoyl,
(2) $C_{1-15}$ alkyl,
(3) $C_{2-15}$ alkenyl,
(4) $C_{2-15}$ alkynyl,
(5) halo,
(6) $OR^b$,
(7) aryl, or
(8) heteroaryl,
wherein said alkyl, alkenyl, alkynyl, and alkanoyl are optionally substituted with from 1–5 groups selected from $R^c$, and said aryl and heteroaryl optionally substituted with 1 to 5 groups selected from $R^d$;

$R^b$ is (1) hydrogen,
(2) $C_{1-10}$alkyl,
(3) $C_{2-10}$alkenyl,
(4) $C_{2-10}$alkynyl,
(5) aryl,
(6) heteroaryl,
(7) aryl $C_{1-15}$ alkyl,
(8) heteroaryl $C_{1-15}$ alkyl,
(9) $C_{1-15}$ alkanoyl,
(10) $C_{3-8}$cycloalkyl,
wherein alkyl, alkenyl, alkynyl are optionally substituted with one to four substituents independently selected from $R^c$, and cycloalkyl, aryl and heteroaryl are optionally substituted with one to four substituents independently selected from $R^d$; or $R^c$ is (1) halo,
(2) aryl,
(3) heteroaryl,
(4) CN,
(5) $NO_2$,
(6) $OR^f$;
(7) $S(O)_m R^f$, m=0, 1 or 2, provided that $R^f$ is not H when m is 1 or 2;
(8) $NR^f R^f$,
(9) $NR^f COR^f$,
(10) $NR^f CO_2 R^f$,
(11) $NR^f CON(R^f)_2$,
(12) $NR^f SO_2 R^f$, provided that $R^f$ is not H,
(13) $COR^f$,
(14) $CO_2 R^f$,
(15) $CON(R^f)_2$,
(16) $SO_2 N(R^f)_2$,
(17) $OCON(R^f)_2$, or
(18) $C_{3-8}$cycloalkyl,
wherein said cycloalkyl, aryl and heteroaryl are optionally substituted with 1 to 3 groups of halo or $C_{1-6}$ alkyl;

$R^d$ is (1) a group selected from $R^c$,
(2) $C_{1-10}$ alkyl,
(3) $C_{2-10}$ alkenyl,
(4) $C_{2-10}$ alkynyl,
(5) aryl $C_{1-10}$ alkyl, or
(6) heteroaryl $C_{1-10}$ alkyl,
wherein alkyl, alkenyl, alkynyl, aryl, heteroaryl are optionally substituted with a group independently selected from $R^e$;

$R^e$ is (1) halogen,
(2) amino,
(3) carboxy,
(4) $C_{1-4}$alkyl,
(5) $C_{1-4}$alkoxy,
(6) hydroxy,
(7) aryl,
(8) aryl $C_{1-4}$alkyl, or
(9) aryloxy;

$R^f$ is (1) hydrogen,
(2) $C_{1-10}$alkyl,
(3) $C_{2-10}$alkenyl,
(4) $C_{2-10}$alkynyl,
(5) aryl,
(6) heteroaryl,
(7) aryl $C_{1-15}$ alkyl,
(8) heteroaryl $C_{1-15}$ alkyl,
(9) $C_{1-15}$ alkanoyl,
(10) $C_{3-8}$cycloalkyl;
wherein alkyl, alkenyl, alkynyl, aryl, heteroaryl, alkanoyl and cycloalkyl are optionally substituted with one to four groups selected from $R^e$;

or a pharmaceutically acceptable salt thereof.

2. A method for the treatment, control, or prevention of hypercholesterolemia, including raising HDL levels, which comprises administering to a mammal in need of such treatment a therapeutically effective amount of a compound of formula I, as defined in claim 1, and a cholesterol biosynthesis inhibitor.

3. The method as recited in claim 2 wherein the cholesterol biosynthesis inhibitor is an HMG-CoA reductase inhibitor.

4. The method as recited in claim 3, wherein the HMG-CoA reductase inhibitor is a statin.

5. The method as recited in claim 4, wherein the statin is selected from the group consisting of lovastatin, simvastatin, pravastatin, fluvastatin, atorvastatin and rivastatin.

6. A method of treating, controlling or preventing one or more diseases, disorders, or conditions selected from the group consisting of diabetes mellitus, hyperglycemia, obesity, hyperlipidemia, hypertriglyceridemia, hypercholesterolemia, atherosclerosis, vascular restenosis, irritable bowel syndrome, pancreatitis, abdominal obesity, adipose cell tumors, adipose cell carcinomas, Syndrome X, polycystic ovarian syndrome, and other disorders where insulin resistance is a component, said method comprising the administration of an effective amount of a compound having Formula I, defined as follows:

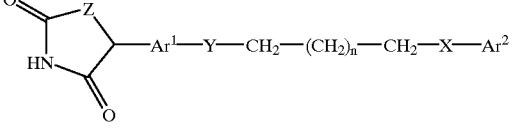

I wherein
$Ar^1$ is (1) arylene or
(2) heteroarylene,
wherein arylene and heteroarylene are optionally substituted with from 1 to 4 groups selected from $R^a$;

$Ar^2$ is (1) ortho-substituted aryl or
(2) ortho-substituted heteroaryl,
wherein said ortho substituent is selected from R; and aryl and heteroaryl are optionally further substituted with from 1–4 groups independently selected from $R^a$;

X and Y are independently O, S, N—$R^b$, or $CH_2$;

Z is O or S;

n is 0 to 3;

R is (1) $C_{3-10}$alkyl optionally substituted with 1–4 groups selected from halo and $C_{3-6}$cycloalkyl,
(2) $C_{3-10}$alkenyl, or
(3) $C_{3-8}$cycloalkyl;

$R^a$ is (1) $C_{1-15}$ alkanoyl,
(2) $C_{1-15}$ alkyl,
(3) $C_{2-15}$ alkenyl,
(4) $C_{2-15}$ alkynyl,
(5) halo,
(6) $OR^b$,
(7) aryl, or
(8) heteroaryl,
wherein said alkyl, alkenyl, alkynyl, and alkanoyl are optionally substituted with from 1–5 groups selected from $R^c$, and said aryl and heteroaryl optionally substituted with 1 to 5 groups selected from $R^d$;

$R^b$ is (1) hydrogen,
(2) $C_{1-10}$alkyl,
(3) $C_{2-10}$alkenyl,
(4) $C_{2-10}$alkynyl,
(5) aryl,
(6) heteroaryl,
(7) aryl $C_{1-15}$ alkyl,
(8) heteroaryl $C_{1-15}$ alkyl,
(9) $C_{1-15}$ alkanoyl,
(10) $C_{3-8}$cycloalkyl,
wherein alkyl, alkenyl, alkynyl are optionally substituted with one to four substituents independently selected from $R^c$, and cycloalkyl, aryl and heteroaryl are optionally substituted with one to four substituents independently selected from $R^d$; or $R^c$ is (1) halo,
(2) aryl,
(3) heteroaryl,
(4) CN,
(5) $NO_2$,
(6) $OR^f$,
(7) $S(O)_m R^f$, m=0, 1 or 2, provided that $R^f$ is not H when m is 1 or 2;
(8) $NR^f R^f$,
(9) $NR^f COR^f$,
(10) $NR^f CO_2 R^f$,
(11) $NR^f CON(R^f)_2$,
(12) $NR^f SO_2 R^f$, provided that $R^f$ is not H,
(13) $COR^f$,
(14) $CO_2 R^f$,
(15) $CON(R^f)_2$,
(16) $SO_2 N(R^f)_2$,
(17) $OCON(R^f)_2$, or
(18) $C_{3-8}$cycloalkyl,
wherein said cycloalkyl, aryl and heteroaryl are optionally substituted with 1 to 3 groups of halo or $C_{1-6}$ alkyl;

$R^d$ is (1) a group selected from $R^c$,
(2) $C_{1-10}$ alkyl,
(3) $C_{2-10}$ alkenyl,
(4) $C_{2-10}$ alkynyl,
(5) aryl $C_{1-10}$alkyl, or
(6) heteroaryl $C_{1-10}$ alkyl,
wherein alkyl, alkenyl, alkynyl, aryl, heteroaryl are optionally substituted with a group independently selected from $R^e$;

$R^e$ is (1) halogen,
(2) amino,
(3) carboxy,
(4) $C_{1-4}$alkyl,
(5) $C_{1-4}$alkoxy,
(6) hydroxy,
(7) aryl,
(8) aryl $C_{1-4}$alkyl, or
(9) aryloxy;

$R^f$ is (1) hydrogen,
(2) $C_{1-10}$alkyl,
(3) $C_{2-10}$alkenyl,
(4) $C_{2-10}$alkynyl,
(5) aryl,
(6) heteroaryl,
(7) aryl $C_{1-5}$ alkyl,
(8) heteroaryl $C_{1-5}$ alkyl,
(9) $C_{1-15}$ alkanoyl,
(10) $C_{3-8}$cycloalkyl;
wherein alkyl, alkenyl, alkynyl, aryl, heteroaryl, alkanoyl and cycloalkyl are optionally substituted with one to four groups selected from $R^e$;

or a pharmaceutically acceptable salt thereof.

7. A pharmaceutical composition comprising (1) a compound of Formula I, as defined below; (2) a second compound selected from the group consisting of an insulin sensitizer, a PPARγ agonist, a glitazone, troglitazone, pioglitazone, englitazone, MCC-555, BRL49653, a biguanide, metformin, phenformin, insulin, an insulin mimetic, a sulfonylurea, tolbutamide, glipizide, α-glucosidase inhibitor, acarbose, a cholesterol lowering agent, an HMG-CoA reductase inhibitor, lovastatin, simvastatin, pravastatin, fluvastatin, atorvastatin, rivastatin, other statins, a sequestrant, cholestyramine, colestipol, a dialkylaminoalkyl derivative of a cross-linked dextran, nicotinyl alcohol, nicotinic acid, a nicotinic acid salt, PPARα agonist, fenofibric acid derivative, gemfibrozil, clofibrate, fenofibrate, benzafibrate, an inhibitor of cholesterol absorption, beta-sitosterol, acyl CoA:cholesterol acyltransferase inhibitor, melinamide, probucol, PPARδ agonist, anti-obesity compound, fenfluramine, dexfenfluramine, phentiramine, sulbitramine, orlistat, neuropeptide Y5 inhibitor, β3 adrenergic receptor agonist, and an ileal bile acid transporter inhibitor; and (3) a pharmaceutically acceptable carrier, wherein the compound of Formula I is as follows:

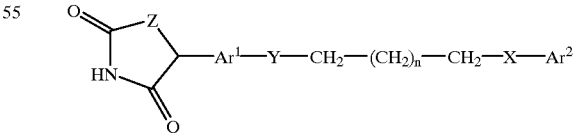

I wherein
$Ar^1$ is (1) arylene or
(2) heteroarylene,
wherein arylene and heteroarylene are optionally substituted with from 1 to 4 groups selected from $R^a$;
$Ar^2$ is (1) ortho-substituted aryl or (2) ortho-substituted heteroaryl,
wherein said ortho substituent is selected from R; and aryl and heteroaryl are optionally further substituted with from 1–4 groups independently selected from $R^a$;

X and Y are independently O, S, N—$R^b$, or $CH_2$;

Z is O or S;

n is 0 to 3;

R is (1) $C_{3-10}$alkyl optionally substituted with 1–4 groups selected from halo and $C_{3-6}$cycloalkyl,
(2) $C_{3-10}$alkenyl, or
(3) $C_{3-8}$cycloalkyl;

$R^a$ is (1) $C_{1-15}$ alkanoyl,
(2) $C_{1-15}$ alkyl,
(3) $C_{2-15}$ alkenyl,
(4) $C_{2-15}$ alkynyl,
(5) halo,
(6) $OR^b$,
(7) aryl, or
(8) heteroaryl,
wherein said alkyl, alkenyl, alkynyl, and alkanoyl are optionally substituted with from 1–5 groups selected from $R^c$, and said aryl and heteroaryl optionally substituted with 1 to 5 groups selected from $R^d$;

$R^b$ is (1) hydrogen,
(2) $C_{1-10}$alkyl,
(3) $C_{2-10}$alkenyl,
(4) $C_{2-10}$alkynyl,
(5) aryl,
(6) heteroaryl,
(7) aryl $C_{1-15}$ alkyl,
(8) heteroaryl $C_{1-15}$ alkyl,
(9) $C_{1-15}$ alkanoyl,
(10) $C_{3-8}$cycloalkyl,
wherein alkyl, alkenyl, alkynyl are optionally substituted with one to four substituents independently selected from $R^c$, and cycloalkyl, aryl and heteroaryl are optionally substituted with one to four substituents independently selected from $R^d$; or $R^c$ is (1) halo,
(2) aryl,
(3) heteroaryl,
(4) CN,
(5) $NO_2$,
(6) $OR^f$,
(7) $S(O)_m R^f$, m=0, 1 or 2, provided that $R^f$ is not H when m is 1 or 2;
(8) $NR^f R^f$,
(9) $NR^f COR^f$,
(10) $NR^f CO_2 R^f$,
(11) $NR^f CON(R^f)_2$,
(12) $NR^f SO_2 R^f$, provided that $R^f$ is not H,
(13) $COR^f$,
(14) $CO_2 R^f$,
(15) $CON(R^f)_2$,
(16) $SO_2 N(R^f)_2$,
(17) $OCON(R^f)_2$, or
(18) $C_{3-8}$cycloalkyl,
wherein said cycloalkyl, aryl and heteroaryl are optionally substituted with 1 to 3 groups of halo or $C_{1-6}$ alkyl;

$R^d$ is (1) a group selected from $R^c$,
(2) $C_{1-10}$ alkyl,
(3) $C_{2-10}$ alkenyl,
(4) $C_{2-10}$ alkynyl,
(5) aryl $C_{1-10}$alkyl, or
(6) heteroaryl $C_{1-10}$ alkyl,
wherein alkyl, alkenyl, alkynyl, aryl, heteroaryl are optionally substituted with a group independently selected from $R^e$;

$R^e$ is (1) halogen,
(2) amino,
(3) carboxy,
(4) $C_{1-4}$alkyl,
(5) $C_{1-4}$alkoxy,
(6) hydroxy,
(7) aryl,
(8) aryl $C_{1-4}$alkyl, or
(9) aryloxy;

$R^f$ is (1) hydrogen,
(2) $C_{1-10}$alkyl,
(3) $C_{2-10}$alkenyl,
(4) $C_{2-10}$alkynyl,
(5) aryl,
(6) heteroaryl,
(7) aryl $C_{1-15}$ alkyl,
(8) heteroaryl $C_{1-15}$ alkyl,
(9) $C_{1-15}$ alkanoyl,
(10) $C_{3-8}$cycloalkyl;
wherein alkyl, alkenyl, alkynyl, aryl, heteroaryl, alkanoyl and cycloalkyl are optionally substituted with one to four groups selected from $R^e$;

or a pharmaceutically acceptable salt thereof.

* * * * *